(12) United States Patent
Chambers et al.

(10) Patent No.: US 11,735,304 B2
(45) Date of Patent: Aug. 22, 2023

(54) ROBOTIC DISPENSARY SYSTEM AND METHODS

(71) Applicant: R/X Automation Solutions, LLC, Longmont, CO (US)

(72) Inventors: Tim Chambers, Longmont, CO (US); Mike Martin, Hot Springs, AR (US); Mathew Card, Broomfield, CO (US); James Wynd, Westminster, CO (US); Cody Small, Loveland, CO (US)

(73) Assignee: MCKESSON CORPORATION, Irving, TX (US)

( * ) Notice: Subject to any disclaimer, the term of this patent is extended or adjusted under 35 U.S.C. 154(b) by 538 days.

(21) Appl. No.: 15/716,377

(22) Filed: Sep. 26, 2017

(65) Prior Publication Data

US 2018/0082757 A1    Mar. 22, 2018

(51) Int. Cl.
*G16H 20/13* (2018.01)
*G16H 40/67* (2018.01)
(Continued)

(52) U.S. Cl.
CPC .............. *G16H 20/13* (2018.01); *G07F 9/006* (2013.01); *G07F 11/165* (2013.01); *G07F 11/42* (2013.01);
(Continued)

(58) Field of Classification Search
CPC ......... B65G 43/08; G07F 11/42; G07F 11/44; G07F 11/165; G07F 17/0092; G16H 20/13; G16H 40/67
See application file for complete search history.

(56) References Cited

U.S. PATENT DOCUMENTS

| | | |
|---|---|---|
| 2,109,988 A | 3/1938 | Dalton |
| 2,111,529 A | 3/1938 | Dalton |

(Continued)

FOREIGN PATENT DOCUMENTS

| | | |
|---|---|---|
| CA | 2129137 | 6/1994 |
| CA | 2560056 | 6/2009 |
| CA | 2646568 | 7/2013 |

OTHER PUBLICATIONS

"Innovation Releases Latest Version of PharmASSIST Symphony Workflow System", Jul. 25, 2012, Press Release (Year: 2012).*

(Continued)

*Primary Examiner* — Thomas M Wittenschlaeger
*Assistant Examiner* — David G Shutty
(74) *Attorney, Agent, or Firm* — Ballard Spahr LLP

(57) ABSTRACT

Embodiments of the inventive technology may relate to a robotic pill dispensing system, whether puck-based or puck-free, configured to avoid delay during the filling of orders and achieve high, perhaps even maximal, order fill rates and associated processing efficiency. Additional embodiments of the inventive technology may relate to, inter alia, a bottle placement site that is different from a bottle pick-up site, a device configured to apply lodged pill clearance forces to counted pill reserve containers; counted pill reserve containers that are large enough to contain pills required by substantially all orders to be handled by a robotic dispensary; a method of dynamically repositioning medication-dedicated pill counters to increase processing speed and a system configured to facilitate the same; a robotic dispensary configured to allow manual operation when a robot is off-line; and a robotic dispensary configured to cover open, filled vials during transport thereof to prevent pill spillage.

20 Claims, 33 Drawing Sheets

(51) Int. Cl.
*G07F 17/00* (2006.01)
*G07F 11/44* (2006.01)
*G07F 11/42* (2006.01)
*G07F 9/00* (2006.01)
*G07F 11/16* (2006.01)
*G16H 40/40* (2018.01)

(52) U.S. Cl.
CPC .......... *G07F 11/44* (2013.01); *G07F 17/0092* (2013.01); *G16H 40/67* (2018.01); *G16H 40/40* (2018.01)

(56) References Cited

U.S. PATENT DOCUMENTS

| | | | |
|---|---|---|---|
| 3,305,067 | A | 2/1967 | Mayer |
| 3,730,388 | A | 5/1973 | Bender |
| 3,837,139 | A | 9/1974 | Roseberg |
| 3,918,475 | A | 11/1975 | Truselle |
| 3,949,792 | A | 4/1976 | Ramoneda Sibidi |
| 4,013,192 | A | 3/1977 | Dillon |
| 4,018,358 | A | 4/1977 | Johnson et al. |
| 4,460,106 | A | 7/1984 | Mouding, Jr. et al. |
| 4,781,696 | A | 11/1988 | Moulding, Jr. et al. |
| 4,785,952 | A | 11/1988 | Obadia |
| 5,183,999 | A * | 2/1993 | Hakenewerth ...... G07F 11/1653 235/379 |
| 5,209,044 | A | 5/1993 | D'Addario |
| 5,337,919 | A | 8/1994 | Spaulding |
| 5,460,294 | A | 10/1995 | Williams |
| 5,480,062 | A | 1/1996 | Rogers et al. |
| 5,559,919 | A | 9/1996 | Solberg |
| 5,587,572 | A | 12/1996 | Kirby |
| 5,720,154 | A | 2/1998 | Lasher et al. |
| 5,810,198 | A | 9/1998 | Townsend et al. |
| 5,884,806 | A | 3/1999 | Boyer et al. |
| 5,905,653 | A | 5/1999 | Higham et al. |
| 5,963,453 | A | 10/1999 | East |
| 6,006,946 | A | 12/1999 | Williams et al. |
| 6,036,812 | A | 3/2000 | Williams et al. |
| 6,053,302 | A | 4/2000 | Leu |
| 6,112,502 | A | 9/2000 | Frederick et al. |
| 6,131,765 | A | 10/2000 | Barry et al. |
| 6,176,392 | B1 | 1/2001 | William et al. |
| 6,253,953 | B1 | 7/2001 | Ishizuka |
| 6,256,967 | B1 * | 7/2001 | Hebron ............... G07F 17/0042 53/437 |
| 6,317,648 | B1 | 11/2001 | Sleep et al. |
| 6,377,648 | B1 | 4/2002 | Culbert |
| 6,421,584 | B1 | 7/2002 | Norberg et al. |
| RE37,829 | E | 9/2002 | Charhut et al. |
| 6,497,342 | B2 | 12/2002 | Zhang et al. |
| 6,504,387 | B1 | 1/2003 | Shail |
| 6,561,377 | B1 | 5/2003 | Pearson et al. |
| 6,594,549 | B2 | 7/2003 | Siegel |
| 6,597,969 | B2 | 7/2003 | Greenwald et al. |
| 6,640,159 | B2 | 10/2003 | Holmes et al. |
| 6,644,504 | B2 | 11/2003 | Yuyama et al. |
| 6,659,304 | B2 | 12/2003 | Gelster et al. |
| 6,681,149 | B2 * | 1/2004 | William ............... B65B 5/103 700/235 |
| 6,681,550 | B1 | 1/2004 | Aylward |
| 6,684,914 | B2 | 2/2004 | Gershman et al. |
| 6,788,997 | B1 | 9/2004 | Frederick |
| 6,899,144 | B1 | 5/2005 | Gelster et al. |
| 6,899,148 | B1 | 5/2005 | Gelster et al. |
| 6,975,922 | B2 | 12/2005 | Duncan et al. |
| 6,983,579 | B2 | 1/2006 | Rice et al. |
| 6,996,455 | B2 | 2/2006 | Eggenberger et al. |
| 6,997,341 | B2 | 2/2006 | Pearson et al. |
| 7,006,893 | B2 | 2/2006 | Hart et al. |
| 7,016,766 | B2 | 3/2006 | William et al. |
| 7,122,005 | B2 | 10/2006 | Shusterman |
| 7,124,791 | B2 | 10/2006 | Gelster et al. |
| 7,139,639 | B2 | 11/2006 | Broussard et al. |
| 7,175,381 | B2 | 2/2007 | Guerra |
| 7,182,105 | B1 * | 2/2007 | Feehan ............... G07F 11/165 141/2 |
| 7,185,477 | B2 | 3/2007 | Rice et al. |
| 7,210,598 | B2 | 5/2007 | Gerold et al. |
| 7,228,198 | B2 | 6/2007 | Vollm et al. |
| 7,258,521 | B2 | 8/2007 | Guerra et al. |
| 7,263,411 | B2 | 8/2007 | Shows et al. |
| 7,289,879 | B2 | 10/2007 | William et al. |
| 7,395,214 | B2 | 7/2008 | Shillingburg |
| RE40,453 | E | 8/2008 | Lasher et al. |
| 7,412,814 | B2 | 8/2008 | Rice et al. |
| 7,430,838 | B2 | 10/2008 | Rice et al. |
| 7,469,820 | B2 | 12/2008 | Rosenbluhm |
| 7,555,362 | B2 | 6/2009 | Broussard et al. |
| 7,565,784 | B2 | 7/2009 | Williams et al. |
| 7,624,894 | B2 | 12/2009 | Gerold et al. |
| 7,631,670 | B2 | 12/2009 | Gelster et al. |
| 7,668,618 | B2 | 2/2010 | Szesko et al. |
| 7,747,345 | B2 | 6/2010 | Ohmura et al. |
| 7,837,107 | B1 | 11/2010 | Leu et al. |
| 7,853,355 | B1 * | 12/2010 | Willemse ............ G07F 11/32 700/242 |
| 7,912,582 | B1 * | 3/2011 | Holtje ............... G07F 17/0092 700/242 |
| 7,991,507 | B2 | 8/2011 | Liff et al. |
| 8,025,085 | B2 | 9/2011 | Skaggs et al. |
| 8,060,248 | B1 * | 11/2011 | Boyer ............... B65B 57/20 700/235 |
| 8,109,066 | B2 | 2/2012 | Leu et al. |
| 8,275,481 | B2 | 9/2012 | Rice et al. |
| 8,434,641 | B2 | 5/2013 | Coughlin et al. |
| 8,423,180 | B1 | 6/2013 | Frederick et al. |
| 8,607,776 | B2 | 12/2013 | Henkel et al. |
| 8,678,231 | B2 * | 3/2014 | Yuyama ............. G07F 17/0092 221/217 |
| 8,694,162 | B2 | 4/2014 | Jaynes |
| 8,983,655 | B2 | 3/2015 | Braun et al. |
| 9,072,652 | B1 | 7/2015 | Balasubramanian et al. |
| 9,073,684 | B2 | 7/2015 | Bailey |
| 9,372,961 | B1 | 6/2016 | Guthrie et al. |
| 9,457,967 | B1 * | 10/2016 | Mahar ............ G05B 19/41815 |
| 9,489,492 | B2 | 11/2016 | Rosenbaum |
| 9,506,903 | B2 | 11/2016 | Guthrie et al. |
| 9,536,369 | B2 | 1/2017 | Wagner |
| 9,592,925 | B2 | 3/2017 | Leu et al. |
| 9,682,016 | B1 | 6/2017 | Balasubramanian et al. |
| 9,697,335 | B2 | 7/2017 | Joplin |
| 9,845,201 | B1 * | 12/2017 | Trinh ............... G07F 17/0092 |
| 9,846,566 | B1 * | 12/2017 | Kapadia ............ G07F 17/0092 |
| 9,914,594 | B1 * | 3/2018 | Mahar ............... B65G 43/00 |
| 9,922,171 | B2 | 3/2018 | Mahar et al. |
| 10,062,455 | B2 | 8/2018 | Mahar et al. |
| 10,303,854 | B2 * | 5/2019 | Joplin ............... G16H 20/10 |
| 10,427,819 | B2 * | 10/2019 | Chudy ............... B65B 5/103 |
| 2001/0002448 | A1 | 5/2001 | Wilson et al. |
| 2001/0019065 | A1 | 9/2001 | William et al. |
| 2002/0032582 | A1 | 3/2002 | Feeney et al. |
| 2002/0070227 | A1 | 6/2002 | Ferruccio |
| 2003/0085235 | A1 | 5/2003 | William et al. |
| 2003/0111484 | A1 | 6/2003 | Pearson |
| 2003/0216831 | A1 * | 11/2003 | Hart ............... G16H 15/00 700/235 |
| 2004/0034447 | A1 | 2/2004 | Vollm |
| 2004/0045977 | A1 | 3/2004 | William et al. |
| 2004/0249498 | A1 | 12/2004 | William et al. |
| 2006/0006190 | A1 | 1/2006 | Janet |
| 2006/0025884 | A1 | 2/2006 | Henkel |
| 2006/0071011 | A1 | 4/2006 | Varvarelis |
| 2006/0105835 | A1 | 5/2006 | Callahan |
| 2006/0124656 | A1 | 6/2006 | Popovich |
| 2006/0161293 | A1 | 7/2006 | William et al. |
| 2006/0259195 | A1 * | 11/2006 | Eliuk ............... B01F 33/8442 700/245 |
| 2007/0042906 | A1 | 2/2007 | Pitts |
| 2007/0186514 | A1 | 8/2007 | Vollm et al. |
| 2007/0205211 | A1 | 9/2007 | Vollm et al. |
| 2007/0208457 | A1 | 9/2007 | Vollm et al. |
| 2007/0271001 | A1 | 11/2007 | Ratnakar |

(56) References Cited

U.S. PATENT DOCUMENTS

| | | | |
|---|---|---|---|
| 2008/0198896 A1 | 8/2008 | Nair | |
| 2008/0283543 A1* | 11/2008 | Karwacki, Jr. | G07F 17/0092 221/7 |
| 2009/0039098 A1* | 2/2009 | Karwacki, Jr. | G07F 17/0092 221/200 |
| 2009/0165644 A1 | 7/2009 | Campbell | |
| 2011/0054668 A1* | 3/2011 | Holmes | G07F 17/0092 221/210 |
| 2011/0202171 A1 | 8/2011 | Rosenbaum | |
| 2011/0305545 A1* | 12/2011 | Davis | B25J 15/00 414/800 |
| 2012/0177473 A1* | 7/2012 | Smith | G07F 17/0092 414/744.3 |
| 2013/0310969 A1* | 11/2013 | Terzini | G06Q 10/087 700/235 |
| 2014/0041750 A1 | 2/2014 | Davis et al. | |
| 2014/0138398 A1* | 5/2014 | Daniels | G07F 11/44 221/202 |
| 2014/0350950 A1* | 11/2014 | Jaskela | G16H 20/13 705/2 |
| 2014/0371901 A1 | 12/2014 | Rosenbaum | |
| 2015/0066204 A1* | 3/2015 | Patel | G16H 20/13 700/232 |
| 2016/0122045 A1 | 5/2016 | Kames et al. | |
| 2016/0129585 A1 | 5/2016 | Davis et al. | |
| 2017/0024541 A1* | 1/2017 | Joplin | G16H 20/17 |
| 2017/0065488 A1 | 3/2017 | Thach et al. | |
| 2017/0107005 A1* | 4/2017 | Joplin | G07F 17/0092 |
| 2017/0116815 A1 | 4/2017 | Wagner | |
| 2017/0121113 A1 | 5/2017 | Wagner et al. | |
| 2017/0351839 A1* | 12/2017 | Hellenbrand | B65G 1/08 |
| 2019/0382203 A1* | 12/2019 | Middelberg | G07F 9/001 |

OTHER PUBLICATIONS

R/X Automation Solutions, Mail Order Central Fill & Specialty Pharmacy Products and Systems. Dated Feb. 9, 2017. 50 pages.

Swisslog, "Box Station, PillBox & PhialBox: Automated Drug Management Systems" (C) 2003.

www.epill.com/md2.html, internet listing of MD.2 Monitored Automatic Medication Dispenser. Wayback Machine capture from Aug. 17, 2000. 2 pages.

www.epill.com/medtime.html, internet listing of Med-Time Electronic "Pill" Dispenser. Wayback Machine capture from Aug. 17, 2000. 2 pages.

Ishizuka et al., Computerized dispensing system: reducing the time of dispensing medicines. Int. J. Biomed. Comput. May-Jun. 1991; 28(1-2):137-46. 1 page.

Thompson, Cheryl A., Technology Helps Patients With Emergency Room Prescriptions. Am. J. Health Syst. Pharm. 2003;60(24). 4 pages.

http://rxshowcase.com/pharmacy_automation_companies.htm, Pharmacy Automation Companies and Pharmacy Robotics Providers. Wayback Machine capture from Feb. 16, 2004. 13 pages.

ScriptPro (R), Pharmacy Automation. "SP 200 (R) with Automated Control Center, Robotic Prescription Dispensing System". Aug. 2003. 2 pages.

Baker, M. H., Swiftpack Swiftcheck Plus 1 Seed Counter Operating Instructions, Technical Data Sheet—0577, Issue 3, Sparc Systems, Ltd., Mar. 30, 2000. 23 pages.

* cited by examiner

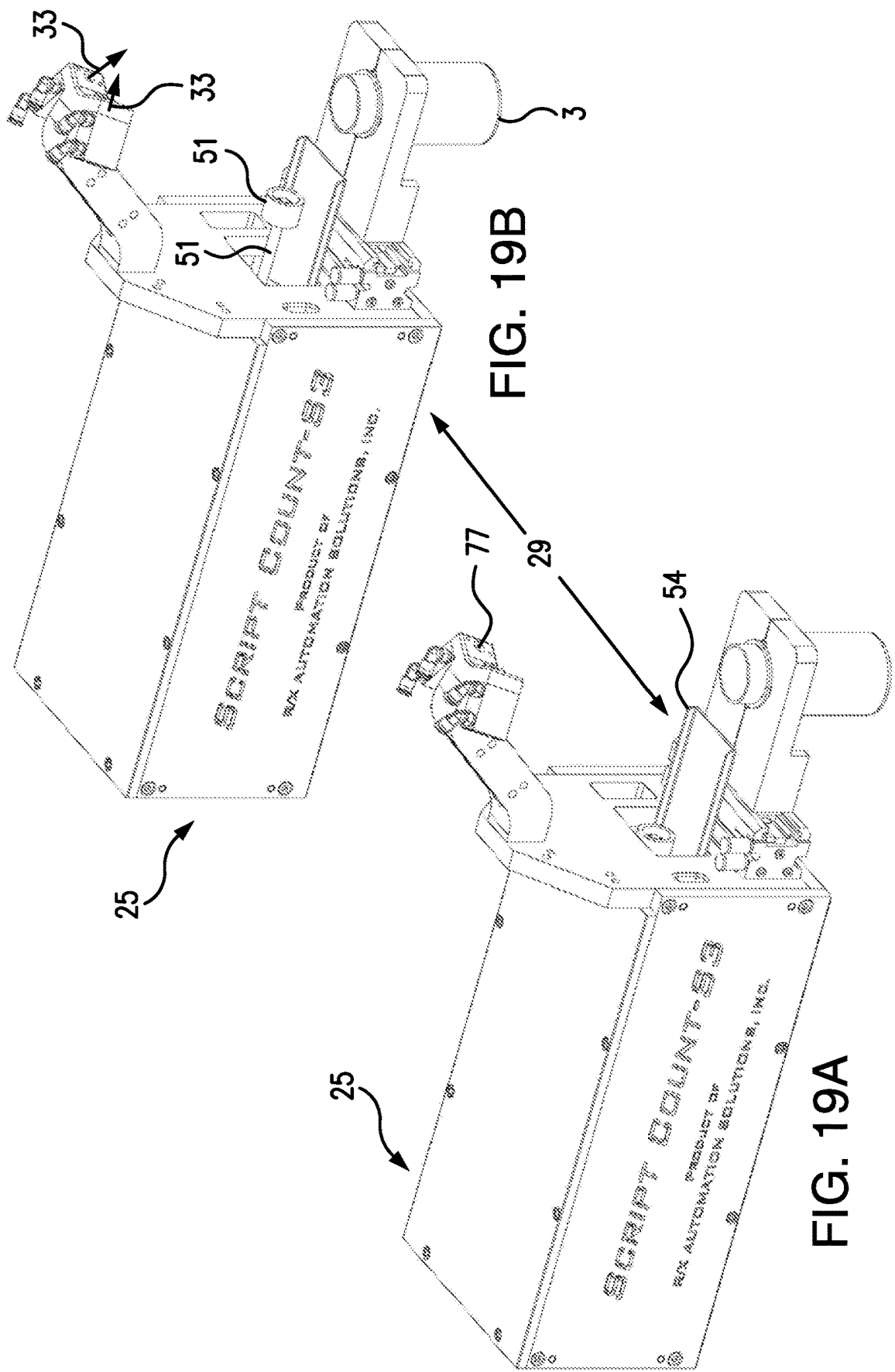

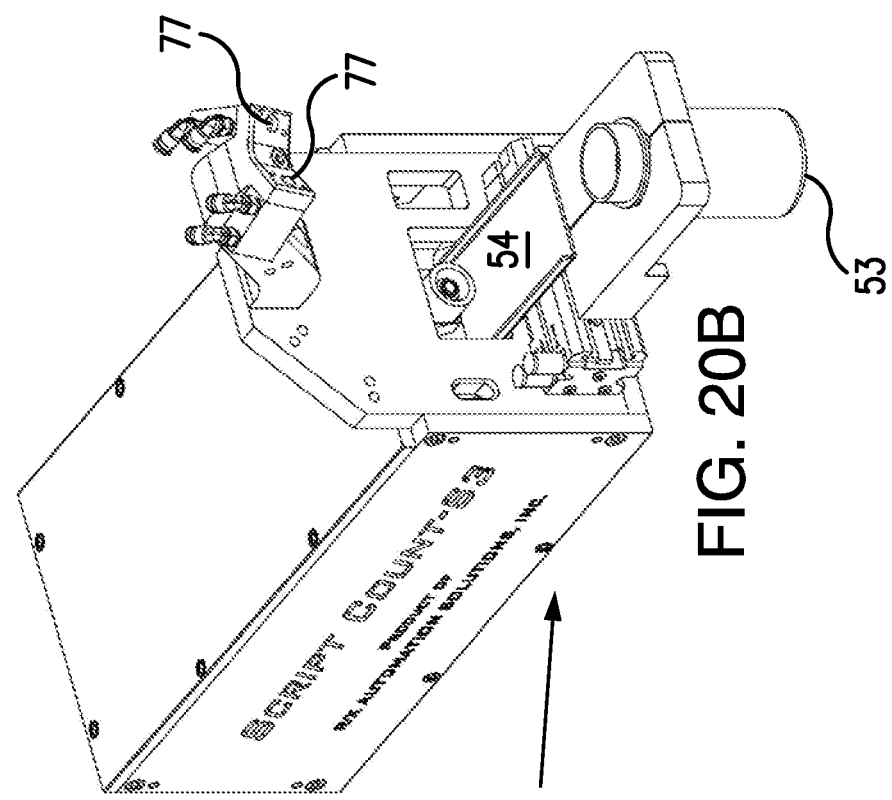
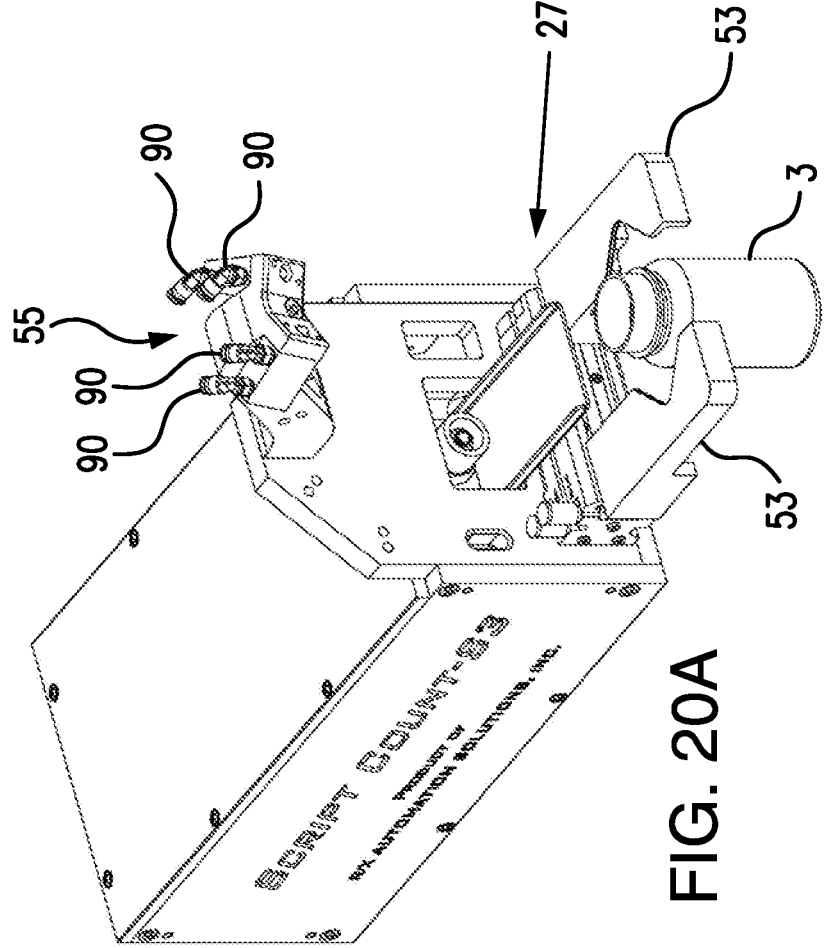
FIG. 20A
FIG. 20B

ROBOTIC DISPENSARY SYSTEM AND METHODS

Embodiments of the inventive technology may find application in automated pharmacies 1, e.g., mail order central fill pharmacies that dispense pills into bottles 3. Each such dispensing operation (including various processes such as but not limited to, e.g., labeling, conveyance, and filling of a bottle) may be according to an order, e.g., a prescription (for an individual, for a certain number of pills of a certain medication). Embodiments of the inventive technology are not necessarily limited to pill dispensing systems 25 such as automated pharmacies 1, as indeed they may find application in automated filling of bottles (a broad term that includes, e.g., vials, containers of any sort, etc.) with ordered amounts of discrete items such as but not limited to pills (e.g., tablets, capsules, caplets, caps, gelcaps, pellets, oral solids, etc.) that must be placed in a specific bottle, in any environment (e.g., pharmaceutical or nutraceutical, where pills are supplements instead of medication, fulfillment of orders for any small items in a certain number of a certain kind, etc.)

Efforts to automate pharmacies and to meet, in automated manner, their goal of fulfilling pill dispensing orders in accordance with prescriptions for individuals (typically human, but also animal such as dog or cat) in a manner that reduces costs as compared with purely manual order fulfillment have been known for quite some time. Such automation may afford advantages not only with respect to cost savings, but also: increased control, enhanced security, improved accuracy of order fulfillment, increased speed of order fulfillment (order or bottle fill rate or speed), more efficient space utilization and/or reduced risk of human error, as but a few examples. Major steps in the automated pharmacy process may include, but not be limited to: labeling of bottles 3; orientation of bottles on a conveyor 4; filling of empty bottles (each with all pills required by an order); conveyance of bottles; capping of bottles, and perhaps even packaging of filled bottles. Embodiments of the inventive technology as disclosed herein may focus only on certain parts of the entire order fulfillment process; indeed, virtually any aspect of the process can be a system. Some embodiments may find application in automated, fully automated, semi-automated, and even primarily manual pharmacies (or generally order fulfillment facilities).

Automated pharmacies 1 may serve as mail order pharmacies, or central fill pharmacies, as but two examples. An automated pharmacy acting as a mail order automated pharmacy may receive orders for medications (e.g., prescription orders), and is configured to fulfill such orders and ship out/mail such individual orders to the individuals (e.g., patients) associated with such orders. An automated pharmacy acting as a central fill pharmacy may receive from, e.g., a company, an insurance company or a drugstore, many patient specific orders (also for different medications), but shipment may be to the ordering entity (e.g., the company, insurance company or drugstore), and may occur in bulk, e.g., via a single truck in a single delivery. Central fill pharmacy applications may achieve economies of size and/or relocation of labor to an automated pharmacy, and the related labor savings associated with having an automated pharmacy handle a plurality of orders instead of filling them in-house.

Embodiments of the inventive technology may feature a system where bottle orienters 2 place bottles held in a vail hopper onto a conveyor 4, which conveys such bottles to a bottle labeling station(s) 5 (e.g., unilabelers) that label a bottle, and, in puck-based systems, marry a puck 6 to a bottle 3 (so that each is associated with each other), and release such puck and married (as shown in FIGS. 28A and B), labeled bottle onto the conveyor, perhaps in an intentionally organized manner (in puck-free systems, no such "marrying" is performed, and only a bottle is released). Note that some systems may be bottle-only (i.e., where no pucks are used to support bottles during conveyance). That conveyor 4 moves empty (and later, filled) bottles, and any associated pucks, along a bottle conveyance path 7 (portions of the conveyor that do not move a bottle, e.g., in those embodiments where, between the bottle pick-up and placement sites 8, 10 (the general area between bottle pick-up and placement sites), the conveyor moves no bottles, or only pucks, are not considered part of such path). The conveyor may be any of a variety of different conveyor types (e.g., slat/apron, roller, wheel, drag/chain/tow, bucket, belt conveyor, etc.).

In puck based systems, each bottle may rest in the "bottle-associated" puck (the puck associated with, e.g., "married to," and supporting that bottle) during at least part of its conveyance along the bottle conveyance path. The puck may be moved along a puck conveyance path that is, in certain embodiments, different from the bottle conveyance path 7 because in such embodiments, the bottle may be removed from the puck at a (empty) bottle pick-up site 8, then robotically repositioned to a (filled) bottle fill site 9, then repositioned to a bottle placement site 10 that is different (e.g., slightly downflow) on the conveyor 4 from the bottle pick-up site 8. Also, there may be parts of the conveyor, e.g., in some embodiments, before the labeler 5, where only a puck is conveyed (before a bottle is placed into a puck for eventual conveyance to a dispensary 11); particular embodiments also convey only a puck between a bottle pick-up site 8 and a bottle placement site 10. In certain puck-based systems, e.g., before a labeler in those embodiments where the labeler also marries the bottle to a puck, part of the conveyor may convey only bottles.

The term conveyor 4 as used herein can refer not only to the entire conveying system, but also to simply the part that directly moves the bottles 3 (e.g., belt, slats, rollers, etc). The labeling station's release of the bottle (and puck, married to form a bottle and puck combination in puck-based systems) onto a conveyor may be in accordance with a release algorithm that may assure that each bottle is on a conveyor recirculation loop 12 when the dispensary 11 (e.g., HVD (high volume dispensary, such as flex bed 13), robotic dispensary 14 such as LVD 15 (low volume dispensary), or mid-range dispensary) is ready to process it, so that there will be no delay attributed to a preference to divert from the recirculation loop a certain bottle (and puck in puck-based systems) that is not on it. Note that the inventive technology also covers the case where system componentry other than a recirculation loop releases the bottles so that they arrive at a bottle pick-up site in an intended order.

Labeling may be in accordance with an order (for a particular individual for a certain number of pills of a certain medication, itself typically associated with a prescription). Accordingly, each bottle, whether released from a labeler or not, may at some point become associated with an order. The conveyor on which the bottle (or possibly puck combination) is released may lead to or be part of a conveyor recirculation loop; bottles may be conveyed around such loop until each is intentionally diverted to a pill dispensary 11 (a type of pill dispensing system 25), whether high volume dispensary, low volume dispensary, mid-range dispensary, low/mid-range dispensary, other volume dispensary, or volume inspecific dispensary.

Reference is at times made herein to order clusters, whether system wide order clusters, or dispensary (either non-robotic or robotic) order clusters. An order cluster may refer to a set of orders as the pharmacy first is made aware of them (e.g., an unorganized list of prescriptions for medications for individuals), and to that same set after it has been reorganized with respect to volume (e.g., highest to lowest volume), and that same set after it has been reorganized in the order in which it is to be processed (e.g., for maximum efficiency). At times, a dispensary order is not identified until a system-wide order is organized with respect to volume.

A system-wide order cluster 19 is an entire order cluster to be handled by the entire system, which may include not only one or more robotic dispensary(ies), but also one or more HVD's. The term dispensary order cluster (as opposed to system-wide order cluster) typically refers to the cluster of orders, e.g., a portion of a system-wide order cluster, that are handled by a single dispensary (e.g., by a single robotic LVD or a single HVD, as but two examples). So where there are more than one dispensary configured to handle a system-wide order cluster (e.g., 5 non-robotic flex beds and two robotic dispensaries (e.g., LVD's) as shown in FIG. 1), dispensaries that are of the same type may together handle a single dispensary order (e.g., the 5 non-robotic flex beds may together handle a single non-robotic dispensary order cluster, and the two robotic dispensaries may together handle a robotic dispensary order cluster).

A high volume dispensary (HVD) may, as but one example, be an arrangement referred to as a flex bed 13. It may involve a single tier of counters arranged in side-by-side array (linear or otherwise); under each counter may be a single lane of empty bottles that are filled when each is successively placed under the counted pill outlet associated with a particular counter. Valuable facility real estate may be conserved using counters that are narrower in width and taller, particularly given the preference for using single tier HVD's (for reasons that relate to ergonomics), thereby allowing for an increased or even maximized horizontal packing density. Note that in certain designs, a 20 counter, single bed HVD may achieve 1500 order fills per hour for 20 (or fewer, or more) medications; a multi-bed system may, in certain arrangements, be able to handle orders for approximately 300 different medications (as but one example), at higher order fill rates, thereby increasing order processing efficiency.

The robotic dispensary technology disclosed herein is broadly applicable, and indeed a single robotic dispensary may be used to handle all orders of a system-wide order cluster (particularly in facilities where there are no flex-beds or other HVD's, or other robotic dispensaries); in such application, a dispensary order cluster (handled by such dispensary) could be the same as a system wide order cluster. Note that a system-wide order cluster may be all orders made (requested) by a single larger entity (e.g., an insurance company). But where such set of orders are particularly large or where an automated pharmacy handles orders from individuals, one after another, with no clear imposition of boundaries to define clusters, a system-wide order cluster may merely be a certain number (e.g., 1000) anticipated orders to be handled substantially sequentially, or anticipated orders to be handled in a certain period of time (e.g., in ½ hour, in an 8 hour "shift," as but a few examples). FIG. 24 shows a system wide order cluster 19 (and the non-robotic and robotic dispensary order clusters that make up a part of it) arranged by decreasing volume.

Each dispensary type (e.g., non-robotic and robotic) may fulfill an certain order (of a dispensary order cluster 20 or 21) associated with a particular bottle generally by dispensing the number of pills of the medication for that order into the bottle. The reason for use of a LVD (instead of handling all orders with the HVD) may relate to the ability to use, for that LVD, less expensive counters 22 and/or a multi-tier array of counters (see, e.g., FIGS. 7 and 9) that occupies less of the valuable real estate in a facility (e.g., because it may have a smaller footprint as compared to other options (e.g., a HVD)). Other reasons may include, but are not limited to, working with a facility's existing dispensary during an update to reduce long term costs, and/or allowing automated pharmacies 1 to meet their desire to use counters that have a count accuracy that meets industry expectations (e.g., at least 99.90%, or at least 99.95%) or that may be preferred to competing counters for other reasons. The LVD, in accordance with embodiments of the inventive technology, may allow for the use of counters with superior count accuracy and fast count speeds to meet the dispensing needs for medications, e.g., those ordered at lower frequency.

As discussed further below, the position of a counter 22 (e.g., which counter space of a counter array frame it is in) in a robotic dispensary (e.g., an LVD) for a particular robotic dispensary order cluster 21 may be different from that counter's position during a different (e.g., subsequent) robotic dispensary order cluster. Indeed, a counter may be moved from one counter space in a counter array frame to a different space in that frame before a second (sequentially after an earlier first) order cluster is processed in order to increase order fill speed of that second order cluster (e.g., the order/hour rate, at which a robotic dispensary fills or meets orders by serially taking vails, one by one, from a conveyor, filling them with the ordered number of pills of the required, ordered medication, and returning them to the conveyor). Such increase in fill speed may result from intentional repositioning of counter(s) for medication that have higher order volume requirements for that cluster (higher ordered medication frequency) closer to the (empty) bottle pick-up and (filled) bottle placement sites 8, 10 than counter(s) for medication that have lower order volume requirements), thereby reducing overall robot end effector travel time during fulfillment of that order cluster as compared to what it would be without such repositioning.

In certain embodiments of the inventive technology disclosed herein, bottles are, at some point, associated with an order for a particular medication (e.g., 20, 100 mg. capsules of medication x), where the term medication may include not only the type of medication but the strength of pill (e.g., 100 mg. capsule of medication x). The label placed onto the bottle may include information regarding patient, patient date of birth, amount (number of pills) to be taken, frequency, refills, route, date of prescription, prescribing physician, etc. and other required/relevant information.

Note, incidentally, that where it is indicated herein that a bottle is conveyed, diverted, obstructed, etc., then: in a puck-free system, the bottle is directly conveyed, diverted and obstructed (perhaps through direct contact therewith), but in a puck-based system, it may be the puck (carrying its bottle) that sits on the conveyor and is directly conveyed, or is or directly contacted by a diverting mechanism or by the obstructer. In such puck-based systems, however, the bottle is still said to be conveyed, diverted or obstructed (of course, such is the case in puck-free systems. Relatedly, except where otherwise indicated, all aspects/embodiments of the inventive technology disclosed herein may find application in either puck-based or puck-free systems. Puck-free systems eliminate the puck; it is a bottle alone that may be conveyed. All disclosure indicated herein, particularly the figures, that show aspects of the inventive technology in a puck-based systems are also intended as disclosure of aspects of the inventive technology in puck-free systems (simply, the puck and puck-related componentry (e.g., a puck-in position sensor) can be ignored). Typically, an entire system (possibly with HVD and LVD dispensaries), would be puck-free or puck-based, although systems where one type of dispensary is puck-based and another type dispensary is puck-free is also within the ambit of the inventive technology.

In certain embodiments, the bottle may be diverted to a HVD (high volume dispensary such as a flex bed(s)) on the one hand, or a LVD (low volume dispensary) on the other, if indeed a system has both such dispensaries, depending on the order frequency (volume) for that medication in a system-wide order cluster 19. At times, as with central fill applications, a system wide order cluster (and the order clusters, both non-robotic 20 and robotic 21, of such system wide cluster, that are handled by dispensary(ies), such as a non-robotic dispensary(ies) and/or robotic dispensary(ies)) are for a particular customer (e.g., XYZ Insurance may have a system-wide order cluster, expressed in terms of frequency/volume, as follows: 1276 orders for medication A, 1240 orders for medication B, 1201 orders for medication C, 1106 orders for medication D, etc.) Frequency/volume may refer to the number of orders per single order cluster (system or dispensary) of a single medication. Again, a system-wide order cluster could be handled by an automated pharmacy with either one or more robotic dispensary and/or one or more non-robotic dispensary. In the example of FIG. 24, the system wide order cluster is handled by a pharmacy with at least one non-robotic dispensary (it/they would handle non-robotic dispensary order cluster 20), and at least one robotic dispensary (it/they would handle robotic dispensary order cluster 21).

As mentioned, the system may include one or more than one dispensary (e.g, at least one high volume dispensary and/or at least one low volume dispensary); each dispensary handles a dispensary order cluster 20 or 21 (or part thereof), which, again, may be a portion of that entire, larger system-wide order cluster. In certain embodiments where there is, in addition to a low volume dispensary(ies), a high volume dispensary(ies), e.g., flex beds, that are designed to process orders for medications of a higher frequency, the system may be designed to have a HVD('s) to handle all orders of a system wide order cluster at or above a certain chosen, ordered medication demarcation frequency (e.g., above 700 orders), and a LVD('s) to handle all orders of such cluster below that frequency (FIG. 24 shows a graph that may be helpful in determining such demarcating frequency). However, at times, an automated pharmacy 1 might only have a robotic dispensary(ies); in such case, all orders, regardless of frequency, may be handled by the robotic dispensary(ies), except perhaps some of the lowest volume medications if, e.g., the dispensaries are not large enough to dispense orders for all medications.

FIG. 24 shows, inter alia, the non-robotic dispensary order cluster 20 to be filled by the one or more high volume dispensary, the robotic dispensary order cluster 21 to be filled by the one or more low volume dispensary, and the lowest volume medications to be filled in some other way (right of robotic dispensary order cluster 21), all in order of highest to lowest volume. Where the non-robotic dispensary order cluster is to be handled by more than one non-robotic dispensary, or the robotic dispensary order cluster is to be handled by more than one robotic dispensary, orders of such cluster can be split among the different equal types of dispensary in any of several ways. For example, where two robotic dispensaries are to handle a robotic dispensary order cluster, and the number of medications each dispensary alone can fill is no greater than the total number of orders in the robotic dispensary cluster, each robotic dispensary may handle the same number and type of medications (although indeed other medication allocation may be used); where the number of medications of a dispensary order cluster is greater than the total number of medications that either of the robotic dispensaries can handle, then it may be necessary that the medication allocation among the two dispensaries is different. It is also of note that the exact delineation of the order clusters (i.e., the frequency chosen to demarcate non-robotic and robotic order clusters) may be made in order that, e.g., the cluster does not involve more medications than a single dispensary can fill. Regardless, the allocation of medications of a system-wide order cluster 19 among different clusters 20, 21 and/or, within each cluster (20 and/or 21), among different of the same type of dispensaries that may exist (i.e., robotic and non-robotic) in a single pharmacy, may be made to increase, perhaps even optimize, efficiency and speed of processing of the entire system-wide order cluster.

Note that, in certain applications in automated pharmacies 1 with more than one dispensary, medications may be allocated among those dispensaries so that the different dispensaries of that automated pharmacy system all complete their dispensing for a system-wide order cluster at substantially the same time; such may achieve fastest processing. In pharmacies with HVD's and LVD's, depending on the demarcating frequency chosen (e.g., the order frequency splitting the non-robotic dispensary order cluster from the robotic dispensary order cluster as shown in, e.g., FIG. 24), it may be necessary to move some counters (each dedicated to a specific medication) from, e.g., the HVD to the LVD and/or the LVD to the HVD at times. One example in which such may be advantageous is where a certain medication falls on one side of the demarcating frequency (a HVD side) for one system-wide order cluster but on the other side (e.g., a LVD side) for a subsequent system-wide order cluster). In this way, operational decisions can be made to reduce or minimize the total time required by several different dispensaries, whether made up of LVD('s) and HVD('s) or not, to handle a system-wide order cluster 19. However, often counters 22 are dedicated to a particular type of dispensary (e.g., only Script Count-S3™ Counters are used for a robotic LVD, while only Script Count-S4™ Counters are used for HVD's, as may be seen in certain embodiments), and such switching might not be possible. Note that the demarcation frequency between non-robotic and robotic order cluster may be chosen to avoid the need to move counters from one type of dispensary to another.

Use of all dispensaries 11 in an automated pharmacy 1 to process a single system-wide order cluster 19 may result in the most efficient processing (e.g., highest overall order per hour fill rate). Where there are two or more of the same dispensary with the same formulary (e.g., where two LVD's have the same medication-dedicated counter allocation/distribution), the robotic dispensary cluster (e.g., the portion of the system-wide order cluster that is to be handled by all of that type of dispensary, such as the portion below a certain ordered medication frequency to be handled by LVD's alone) may be split evenly between such dispensaries, with each dispensary still handling a portion of the dispensary order cluster that is substantially the same, although this is not a requirement. Note that, while both HVD and LVD dispensaries are not required in every application, certain applications do involve the use of both. Either or both of such dispensaries may be robotic, although in particular embodiments, the LVD is a robotic dispensary while the HVD is not.

Note that any of the inventive technologies disclosed herein, even though perhaps described in the context of a LVD, may find application to any dispensary 11 (e.g., high volume, low volume, medium (mid-range) volume, low/mid range volume, high/mid range volume, or volume inspecific), that involves the use of a robot for its dispensing operation (i.e., a robotic dispensary). Some aspects of the inventive technology disclosed herein might even find application in dispensaries that are not robotic.

As with any dispensary 11, each counter may be associated with, and dedicated to, a particular medication. A counter excludes componentry that may be removably attached thereto at its outlet or merely placed against its outlet, such as a counted pill reserve container (e.g., a counted pill reserve tube); such componentry is considered external of the counter, even where such are attached to (typically removably), contacting or positioned up against the counter. The external hopper, however, because of its commonplace use in connection with most if not all applications of the counter, is considered part of the counter in those designs where a hopper is dedicated to a counter, even though it is typically removably attached to the main counter housing 24.

The document entitled "Mail Order Central Fill and Specialty Pharmacy Products and Systems" (RX Automation Solutions)—provided with and as part of the initial filing—is hereby specifically incorporated herein by reference.

SUMMARY OF THE INVENTIVE TECHNOLOGY

The inventive technology may, in its various embodiments, relate to a robotic dispensary configured to reduce/eliminate robotic wait time during bottle filling and/or during a robotic bottle reposition cycle via intentional/calculated bottle queuing, diversion of empty bottles to a bottle pick-up site 8 at appropriate times, and sufficiently large counted pill reserve containers, and/or counting of pills in a way that does not require robotic idling during a counted pill dispensing event. Additional aspects of the inventive technology such as a cover over filled bottles during robotic transport thereof, side-by-side bottle pick-up and placement sites 8, 10; robotic agitation of counted pill reserve containers during a counted pill dispensing event; counted pill reserve containers that move in response to regulated agitation forces intended to clear any lodged pills; allowance for manual repositioning of counters based on frequency of orders that involve a particular medication; provision of manual operation as backup in the event of robot unavailability (where a robot is offline for whatever reason); and/or customization of the time a robot must hold a bottle stationary during a dispensing event to fill that bottle, may, individually and in any combination, contribute not only to, e.g., order fulfillment speed, but also possibly processing accuracy, operational confidence and reliability, and/or elimination of the need for costly Pharmacist Verification 2.

The inventive technology, in certain of its various aspects and embodiments, may provide a robotic dispensary that achieves one or more of the following: increase in speed or pill order fulfillment, including bottle filling; reduction in dispensary and/or automated pharmacy operation costs; improvement in count accuracy; reduction in errors associated with incorrect medication; reduction in labor costs associated with a pharmacy; confidence in ability to fill orders; around the clock pharmacy operation; increase in safety of individuals for whom medication is prescribed, and/or reduction, even elimination at times, of robot idle time in a single robotic dispensary order cluster 21. Of course, other goals and advantages of certain of the many embodiments disclosed herein may appear below in the description.

BRIEF DESCRIPTION OF THE FIGURES

FIGS. 19A and 19B show a perspective view of an end effector (of the robot) as may appear in certain embodiments of the inventive technology, with a rod in retracted mode (FIG. 19A) and a rod in extended (triggering) mode (FIG. 19B) to push on and open a reserve container door (not shown). Both figures also show a bottle grasped by a gripper, a bottle opening cover in retracted position, and a device configured to apply lodged pill clearance forces to a reserve container (a lodged pill clearance force applier).

FIGS. 20A and 20B show a perspective view of an end effector (of the robot) as may appear in certain embodiments of the inventive technology, with an extendable rod (to open reserve container door) in retracted mode. FIG. 20A shows the gripper in open mode while FIG. 20B shows a gripper fully closed in order to hold a bottle of a small neck size (note that because of the small bottle size, this gripper configuration appears identical to that of a fully closed gripper, as seen where no bottle is present; other larger bottle sizes may be grasped by a gripper that is in an intermediate position between fully closed and fully open). Both figures show a bottle opening cover in retracted position, and a device configured to apply lodged pill clearance forces to a reserve container.

FIG. 20A shows the bottle opening cover in deactivated position while FIG. 20B shows a cover in activated position to fully cover a bottle opening. Both figures show a device configured to apply lodged pill clearance forces to a reserve container.

FIG. 24 also shows anticipated volume of a non-robotic dispensary order cluster 20 and of a robotic dispensary order cluster 21.

FIG. 25 (and FIG. 26) shows 18 sets, but only 11 sectors. Indeed, because sectors are often delineated based on average times of the sets of counters, where sets with substantially equal (to the tenth of a second) times are deemed in the same sector, such times are also of the 11 sectors shown. Note how three sets of counters make up a particular sector (see Sector 10) in this example. Because what is shown is only half of the dispensary, a mirror image of what is shown is also present in the embodiments as they present during operation. So 6 sets of counters actually make up Sector 10.

FIG. 28B shows a RFID tag 58 on the bottom of the puck.

DESCRIPTION OF THE VARIOUS EMBODIMENTS OF THE INVENTIVE TECHNOLOGY

Figure 1:
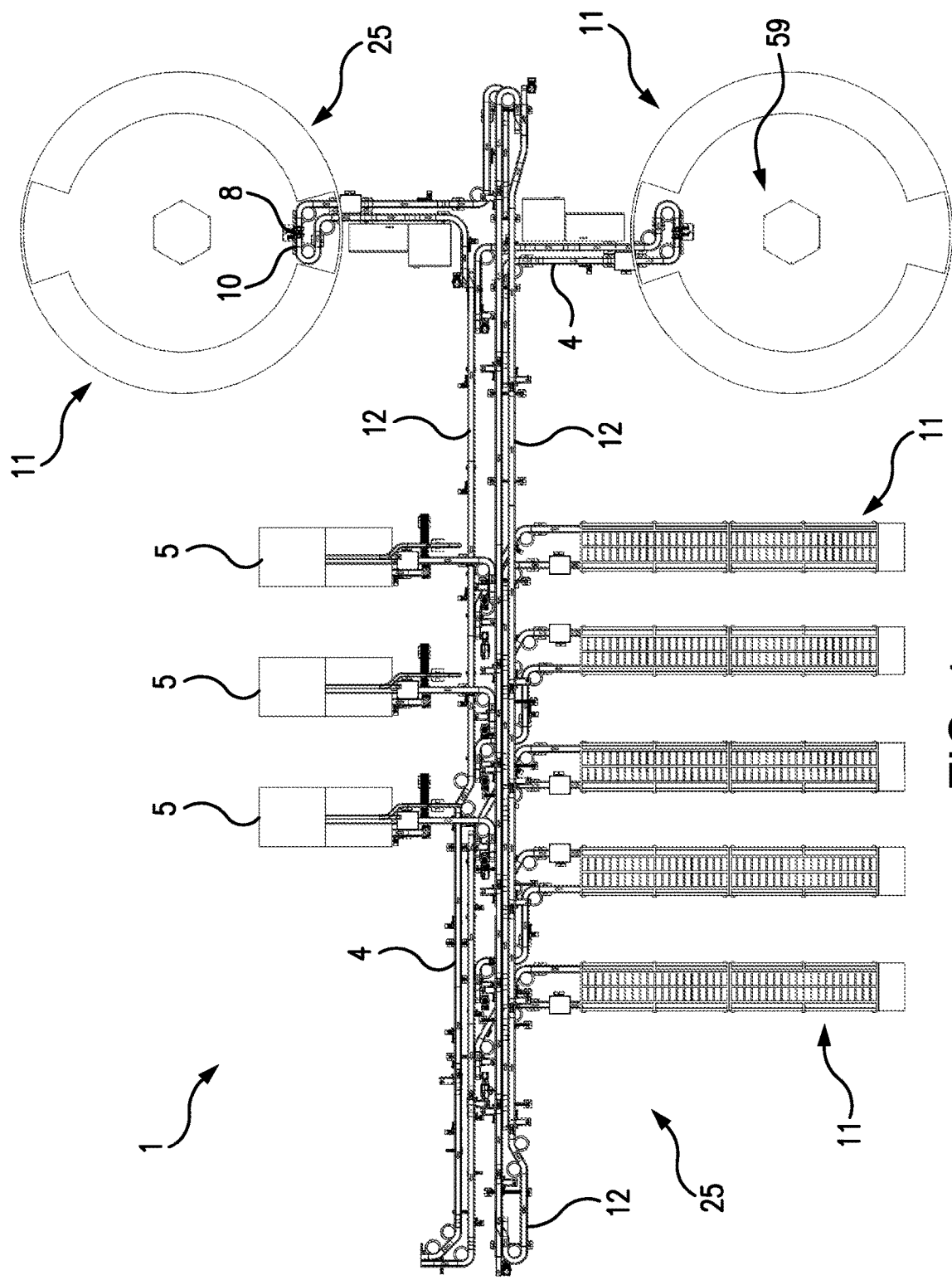
FIG. 1 shows a plan view of an embodiment of the pill dispensing system 25 (here, components of an automated pharmacy that may be used as a mail order or central fill pharmacy) as may appear in certain embodiments of the inventive technology.
Figure 2:
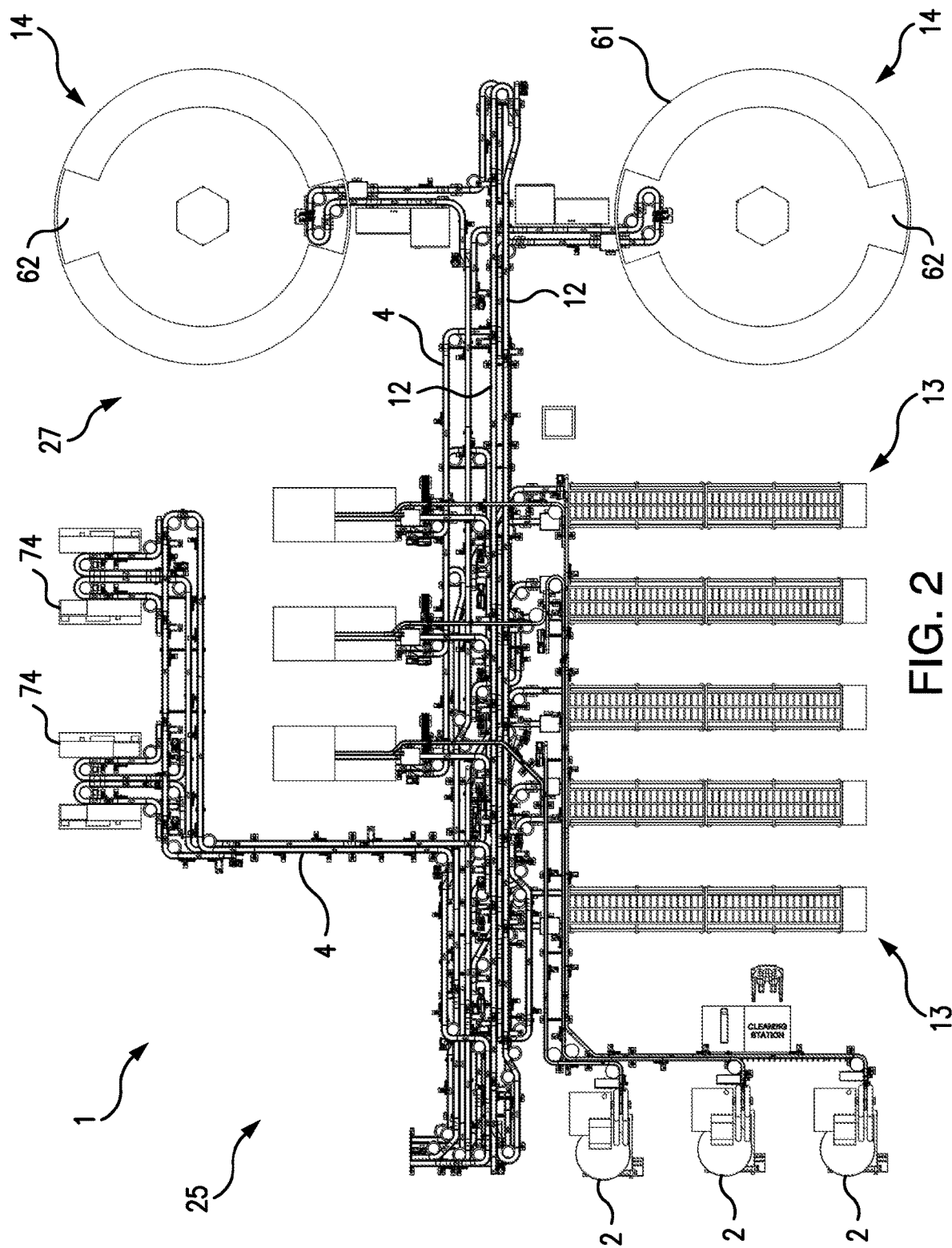
FIG. 2 shows a plan view of an embodiment of the pill dispensing system 25 (here, components of an automated pharmacy that may be used as a mail order or central fill pharmacy) as may appear in certain embodiments of the inventive technology.
Figure 3:
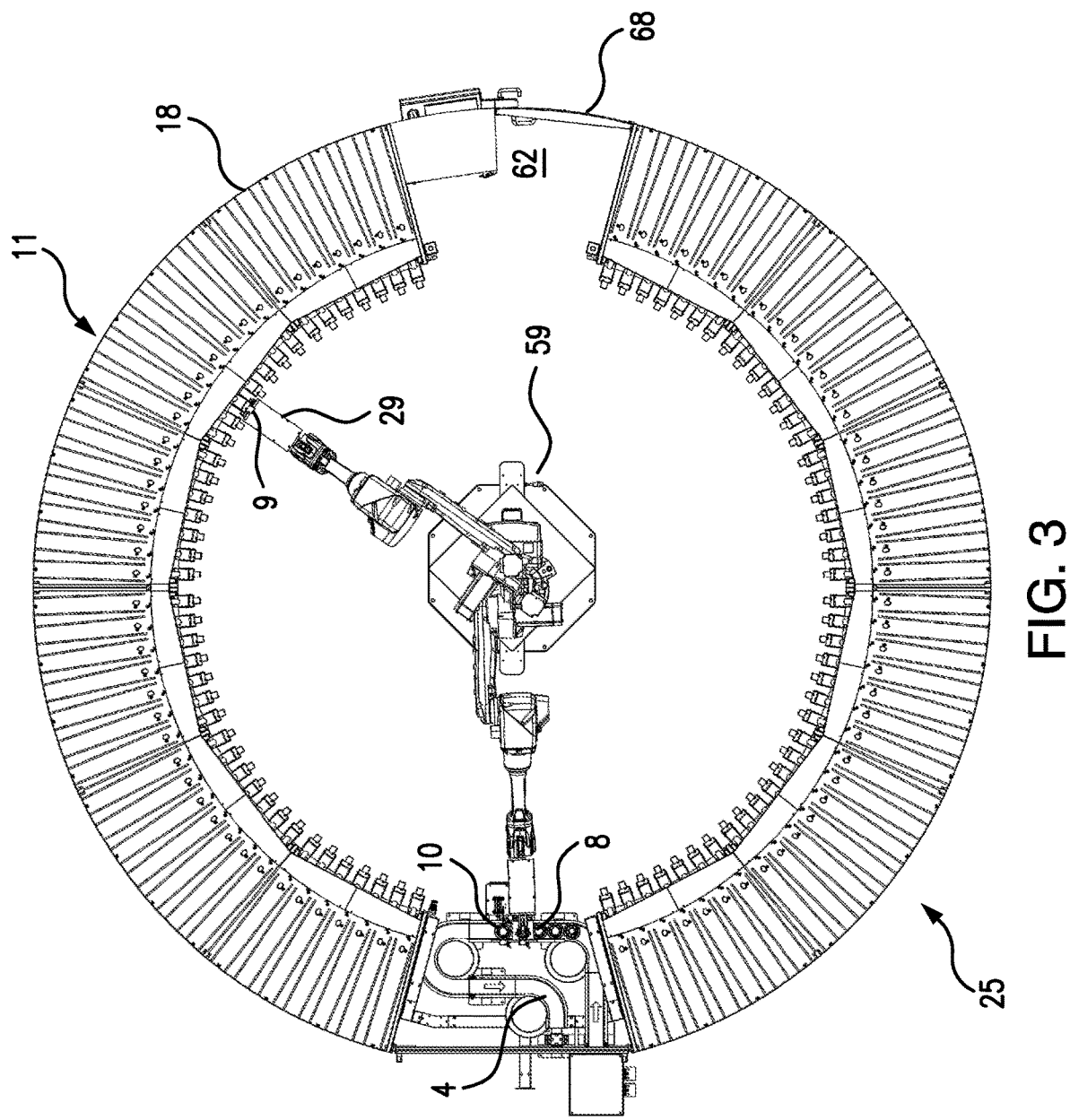
FIG. 3 shows a plan view of an embodiment of the robotic pill dispensing system 27 (more particularly, here a robotic pill dispensary such as a LVD) as may appear in certain embodiments of the inventive technology. It shows, for clarity, two positions of the robot arm—one placing the robot end effector at the bottle pick-up site 8, and another placing the end effector (and a bottle it holds) at a bottle fill site 9 that is in front of (and below) a counter.

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments are not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The robotic dispensary 14 (e.g., LVD 15) may have a different arrangement from a non-robotic dispensary (such as a HVD), and may even use different counters 22 (e.g., counters without an internal hopper, with a lower total height and/or with a larger left-right width) as compared with those counters used for the HVD (or more generally non-robotic dispensary), in order to increase vertical packing density. That different arrangement may be multi-tiered, and may even be one that partially surrounds a central region 59, perhaps along at least portions of a circle 61, other curve (e.g., oval or ellipse), or generally, a shape (e.g., a closed shape such as an octagon, rectangle or a square, or just two straight or curved sides facing each other). In certain embodiments, the counters may even be arranged as a wall (straight or curved) facing a certain side where the robot 31 would preferably (in such embodiments), be located. Regardless of the exact arrangement, certain configurations may use a structural support frame 18 for counters 22 that arranges and supports such counters in a configuration that roughly resembles a coliseum of sorts, with "stands" that could even be vertically disposed, perhaps with vertical "strips" that are free of counters, e.g., where an entryway 62 (for human access to a centrally positioned robot) is positioned, and separately where robotic access to conveyed bottles 63 is provided. The robotic dispensary 14, instead of having counters 22 arranged so as to at least partially surround a central region 59 (with a robot established to access the general area in front of counters), may, as mentioned, even be, e.g., single wall, whether curved, straight and/or several straight sections (when viewed from above), with a robot positioned so as to be able to reach substantially in front of the lower portion of each counter so arranged. Note also that 15 of the figures, while referred to herein at times as a LVD, may also serve as a low/mid-range volume dispensary, a mid-range volume dispensary, or even, in certain applications, as a mid-range/high volume or high volume dispensary.

The LVD 15, or more generally, a robotic dispensary 14 (again a type of pill dispensing system 25), in certain embodiments, may feature the following steps/functions: a conveyor may move an empty (and any puck that may support it in puck-based systems) to an (empty) bottle pick-up site 8; such bottle (and any puck), are typically associated with a particular order (of a robotic dispensary order cluster 21). That bottle 3 is to be filled with a certain number of pills of a particular medication in accordance with an order (such is a "bottle-associated order"). A robot 31 (e.g., a pick and place robot, whether 6 axis or otherwise) may be established so as to pick up an individual, empty bottle from a bottle pick-up site 8 (leaving its puck in place, in puck-based systems) and move that empty bottle 3 to a bottle fill site 9 that is below (perhaps not immediately below) the counter 22 that is dedicated to the particular medication for the order associated with that bottle. In particular embodiments, such bottle fill site 9 is immediately below a lower end 39 of a counted pill reserve container 32 that is substantially below and in front of the counter; such a bottle fill site 9 is below the counter. Note that an item or site is deemed below a component (e.g., a counter) even where it is also in front of, behind, and/or to the side of (or directly below, of course) that component (e.g., counter), as long as at least a majority portion of that item or site is lower than the lowest portion of that component. Similarly, an item or site can be in front of a component (e.g., a counter) even though it is also below or above (or, of course, neither above nor below) that component.

That bottle pick-up may be the first step of a bottle reposition cycle. Typically before that first step, a robot end effector 29 has been established in a bottle pick-up site 8. To start the cycle, the end effector 29 picks up (e.g., grasps) a bottle, e.g., with a gripper 53. After such pick-up, the bottle is then transported via robot, while it is held by the end effector, to a bottle fill site 9 that is associated with a particular counter 22. Extending from that counter is a reserve container 32 in which is reserved and "waiting" a pre-counted, correct number of counted pills for a correct medication. There then may be a pause in robotic transport of the bottle, at the bottle fill site, during a dispensing of pills into the bottle (during a dispensing event, e.g., as pill slide). The filled bottle is then robotically transported to a filled bottle placement site 10 to place the filled bottle there, into position to be moved by the conveyor (and into its awaiting, associated (empty) puck in puck-based systems). The final step in such cycle is robotic transport of the end effector 29 to the bottle pick-up site 8 (such motion is deemed a part of the bottle reposition cycle even though it does not involve repositioning of a bottle). Such cycle is then repeated again, starting with pick-up of the next empty bottle awaiting robotic transport for eventual filling with a prescribed number of pills from a different counter (and often even a different medication).

Such cycle may be specific to and associated with a particular bottle 3 because that bottle is associated with an order for a particular number of pills of a certain medication, and the counter 22 (or counters) for that medication and with which such pills have been intentionally counted is located in a particular counter space 17. That counter is also associated with the bottle (it is a bottle-associated counter 64). For similar reasons, that counter has established in its proximity (e.g., somewhere below it and in front of it), a bottle-associated bottle fill site 65 that is substantially at the end of a bottle-associated counted pill reserve container 66 (which reserves the correct number of pills of the correct medication for a certain bottle, as described in more detail below). Note that even where more than one counter 22 for a particular medication is established in the robotic dispensary 14, and even though one bottle may have an order that is identical to the order for a different bottle, each bottle may have associated with it: a bottle associated, bottle reposition cycle; a bottle-associated pill counter 64; a bottle-associated counted pill reserve container 66; and a bottle-associated bottle fill site 65, inter alia. The robot 31 of a single dispensary processes (e.g., moves and positions for filling) one bottle at a time; after a cycle for a bottle is complete, the cycle for the next bottle is performed (bottle handling and processing may be termed "serial" and "cyclical.") To fulfill the order associated with the "next in queue" bottle, the robot will move that bottle through a bottle reposition cycle associated with that bottle; during such cycle the robot will move the bottle to a different counter that has extending from it a reserve container 32 in which the correct number of pills of the medication for that order are waiting. This is, of course, the result of an intentional scheme to assure that each next cycle involves bottle transport to a reserve container 32 that already has the correct number of pills of the correct medication already counted, and waiting and ready to be dispensed. Of course, this increases order fill speeds (because no robot idling is forced on the system in order to wait for pills to be counted). With proper planning, typically via computer/PLC, the robot can move continuously, non-stop, through a dispensary order cluster 19. Note that a dispensed medication may be considered a correct medication where it is of the correct manufacturer, correct drug, and correct strength.

After the empty bottle is moved by the robot 31 to the bottle fill cite, the bottle is filled according to the order associated therewith (note that even where even, e.g., ½ or ⅔ of the bottle's internal volume is occupied by pills, it is still said to be filled or full, if indeed the order's pill requirement results in such partial filling). The filled bottle may then be moved by the robot to a bottle placement site 10, where the bottle is released by the robot end effector 29 (and into its awaiting, bottle-associated puck in puck-based systems). The robot may then reposition its end effector 29 (e.g., a gripper 53 of the end effector) to the bottle pick-up site 8, ready to pick-up the next empty bottle, associated with a different order, from such site, thereby initiating a new bottle-associated, bottle reposition cycle. Note that where one prescription requires the filling of two or more bottles, each such filling is considered a different order.

Note that filled, fill or full as used herein with respect to a bottle refers to the containment of all pills required by an order in a bottle; the entire allowable/possible internal or containment volume of a bottle is not necessarily occupied by the pills required by an order for that bottle to be filled (a pill "filled" only halfway is still filled or full if all pills of the order associated with that bottle only occupy half of its internal volume, and several more pills could be fit in that bottle), although it certainly may be. Throughout the process, the bottle and/or puck (in which the bottle may rest during transport on the conveyor in puck-based systems) may be tracked (e.g., via optical scanning, RFID, or other known or foreseeable technique), and measures to assure the security of the process and order fulfillment generally may be implemented, whether manually or in automated manner. Note that in bottle-only (puck-free) systems, some identifier, such as but not limited to 2D bar code on the bottle, may be used to track the bottle and coordinate certain bottle related events. In puck-based systems, each the puck and bottle may have identifiers (e.g., bar code and/or RFID) that are associated so as to uniquely marry a puck to a bottle for a dispensary order).

For a single robotic dispensary order cluster 21, each of the counters 22 in the robotic dispensary 14 may have associated therewith a counted pill reserve container, each of which may be external of, and extend downwardly from the counter with which it is associated (for that dispensary order cluster). Note that a counter and attached components (e.g., a counted pill reserve container) are together also a type of pill dispensing system 25 (as is a dispensary, as is a conveyor 4 and dispensary, as is a robot 31 and array of counters, as is an end effector 29 and robot, as is a reserve container 32 and certain componentry, etc.). Particularly in those embodiments where the robotic dispensary presents counters arranged in multi-tiered manner, the reserve containers 32 may also angle away from the counter such that, from a right or left side perspective, the reserve containers, whether straight or otherwise, appear neither vertical nor horizontal (i.e., they are off-vertical and off-horizontal). Where a line drawn between the two ends (inlet end/upper end 38 and outlet end/lower end 39) of a reserve container 32 is neither horizontal nor vertical, then such is an off-vertical and off-horizontal reserve container, regardless of the shape of the container between such ends. Note that the containers may all have substantially the same shape (they need not however); they may each have a longitudinal axis 67 (e.g., where they are straight tubular in shape).

Again, reserve containers 32 need not be straight, but certainly may be. They can have a variety of different shapes (in cross-section and along the length), although in one embodiment they are substantially straight, and tubular. They can be made of a variety of different materials (e.g., plastic, resin, nylon, polyurethane, polyethylene, steel, glass, fiberglass, etc.); embodiments where containers are transparent may provide the advantage of allowing visual inspection of contents. A configuration where the reserve container 32 angles away from the counter 22 (e.g., inwardly towards a central region 59 defined by the robotic dispensary's counter array, or generally towards a robot) may help to allow "stacking" of counters (even where a frame 18 is used to support each counter) in a vertically dense manner because there may be no part of the reserve container 32 that exists immediately below a counter with which it is associated, and no such blockage to vertical stacking that such would impose. Indeed, a design where the lower end 39 of the reserve containers 32 (where a door 52 may exist) is at a height that falls between the top and bottom of the counters of the tier below, but is in front of such lower tier counter (i.e., a vertically overlapping design) may help to achieve a vertically dense space utilization, and related cost-savings.

Regardless of the exact array configuration, the bottle fill sites 9 for each bottle reposition cycle (each such site is also associated with a specific counter 22 during a single bottle reposition cycle) are substantially below lower ends 39 of the counted pill reserve containers. At such lower ends, there may be established some sort of door 52 that can be opened to dispense counted pills (perhaps referred to as "pre-counted" pills) in accordance with an "instant order" (a term used merely for clarity of description, referring to the order that is being fulfilled in a specific cycle by a specific counter), and closed (via door closure) so that the reserve container 32 can then be filled with the correct number of pills in accordance with the "next order" that is to be filled at that same bottle fill site (which would be for the same medication in a single dispensary order cluster 21). In certain embodiments, an extendable rod 51 may extend from an end effector 29 at the appropriate time to apply a force that opens the door; release of that force may cause door closure (the door may be biased in, e.g., the closed direction, whether via spring, elastic, pressurized fluid, etc.)

Note that the next order to be filled at that same bottle site (i.e., associated with that "instant order") would typically not be the immediately subsequent order filled by the robotic dispensary 14, as orders to be filled by other counters 22 instead would be subsequently processed so that the counter associated with that prior order (referred to above as "instant order") can have time to count pills and deposit them in that counter's reserve container 32 (so that they are awaiting an empty bottle when it is placed under that counter's associated bottle fill site 9). The bottle for the next order for that same counter would typically be positioned for pick-up in the bottle pick-up site 8 (e.g., by a first bottle obstructer) only after all the pills required for the next order handled by that counter are counted and waiting in that same counter's reserve container; during such counting, other orders, using other counters, are serially filled (repeatedly, one-at-a-time). The system is coordinated so that repeated bottle filling, and the repeated bottle repositioning by the robot, is performed continuously, without any delay or need for the delay in any system component, particularly the robot 31 (indeed, processing of a dispensary order cluster 21 is preferably seamless, as may be the transition from one order cluster to a subsequent one). Delay includes but is not limited to slowed robotic motion speed, stoppage in motion, delay in onset of motion, etc.; various embodiments seek to avoid delay in filling all orders of a dispensary cluster, more than 99% of such orders, more than 95% of such orders, or more than 90% of such orders. In certain embodiments, bottle queuing before (upflow of) the bottle pick-up site 8, as coordinated by, e.g., a computer/PLC (e.g., to selectively divert bottles individually, one at a time, from a recirculation loop 12), is organized (e.g., first handle one order, then a different order, then a different order, etc.) so that when an empty bottle is waiting to be picked up at a bottle pick-up site 8, it can be immediately picked up and taken to a bottle fill site under a reserve container 32 with the correct number of pills of the correct medication, all without idling (a type of delay) in robotic movement. Bottle fillings may be queued so that, with respect to preferably all counters, after a dispensing event, enough time is allowed so that all pills are pre-counted and in the reserve container when the robot next places a bottle below such reserve container (as indicated elsewhere herein, a sufficiently large reserve container may also be important in meeting the goal of reducing, minimizing, or eliminating delay). This results in reduced (e.g., no or acceptably small amounts of) robot idle time during any single dispensary order cluster. Such robot idle time does not include stationary robot time that is only as long as a pill dispensing event, e.g., a "pill-slide" (such is not delay).

Again, in preferred embodiments, bottle queuing (where bottles (and their respective pucks 6 in puck-based systems) appear in singulated manner) on the conveyor leading to the bottle pick-up site 8 may be arranged so an empty bottle is not moved to a bottle fill site 9 unless the reserve container 32 associated therewith contains, upon arrival of the bottle at that fill site, the entire number of pills required by the order associated with that bottle. Of course, an intentional selection of the order in which bottles are to be filled may be important in meeting such a goal. What may also help to achieve this in certain applications is a start of pill counting by any one counter 22, during a dispensary order cluster 21, that occurs immediately after a counted pill reserve container 32 associated with that counter is emptied; however, in certain applications, reduced, no, or minimal robot idle time may still be achieved where counting by a counter not started immediately after every dispensing event. Often during operation of the LVD 15, several counters, perhaps even most, will be simultaneously counting; such automated counting may even take place while other counters (that are not counting) are manually repositioned. Of course, there may be robot idle time (and in fact the entire robotic dispensary may be offline) between successive dispensary (and system-wide) order clusters 19, although, as indicated, this is not necessary at all.

Counted pill reserve container doors 52 may be biased, e.g., biased in the closed direction, although this is not a requirement. Each door may be controlled to open and or close in any of many ways: some sort of proximity sensor 42 that signals opening/close the door when the robot end effector 29 moves within/without a certain distance from the door or the reserve container; computerized (e.g., PLC) control to open/close the door based on expected/actual time of arrival/departure of the end effector 29 at the fill site; contact sensing; optical or other recognition; mechanical triggering when the bottle or end effector 29 (or part thereof) contacts the door or a certain part to cause door opening; physically forcing of door open with a part on the robot end effector 29 (e.g., with an extendable rod 51); communication so opening and closing occurs when the robot end effector 29 is stationary and positioned at a bottle fill site 9; opening based on information/feedback regarding end effector 29 position; or any other known way of effecting an opening and closing at acceptable times. Indeed, such sensors, communication, mechanical triggering, physical force application, proximity sensors, other sensors, microprocessor control, PLC control, etc. may be used to properly time, control and/or verify the occurrence of many system operations. Note that positional feedback/information regarding a robot 31, its arm 28 or its end effector 29 may also be used to trigger actions, events or occurrences.

While speed goals would typically improve by opening the door 52 as soon as possible (e.g., immediately after a bottle is positioned at a bottle fill site 9), door closure need not be performed immediately upon departure of the bottle (and end effector 29 that may grasp it) from the bottle fill site to achieve desired speeds, although indeed that may at times be needed to achieve speed goals, because door closure is typically a requirement before counting can initiate. Of course, pill discharge from the counter 22 (out of a counted pill outlet 72 of a counter) to fill a reserve container 32 with the number of pills required by an order should not start until the door(s) at the outlet of such containers is/are closed. An appropriately selected and configured proximity sensor 42 may be used to verify that such doors have been closed after a dispensing event.

Note that a structural (e.g., steel) frame 18 may be used to support the counters 22 securely in their arrangement in the robotic dispensary 14. Typically such frame is without any movable shelves for counter support, and such counters, while capable of being taken out of their position in the robotic dispensary array for repair, or reposition to a different counter space 17 in the array, are not positioned on any such moving shelves.

A single robotic dispensary may be configured to fill any number of orders per hour, although certain embodiments in particular may achieve at least approx. 480 orders/hour, e.g., approx. 500 orders/hour (as but two examples), at maximum processing. A single LVD 15 may also be configured to fill orders for any number of medications, although 252 is the number of different medications one LVD embodiment in particular can handle (at least 252 counters 22, at least one for each SKU (stock keeping unit, e.g., the left 9 digits of a NDC) or medication). When two such LVD's are used for a single recirculation loop 12, the total LVD formulary capacity can be increased (e.g., 504, as but one example). Together, such two LVD's, each averaging a bottle fill once every 7 seconds (in certain embodiments), can average a bottle fill once every 3.5 seconds (approx.), filling over 1000 orders (e.g., prescriptions) per hour. Of course, these are merely examples of the many different rates and speeds achievable. More particularly as to medications that can be handled, note that in one exemplary application, a pharmacy with both HVD's and LVD's may handle 804 total drugs (e.g., with the HVD's (e.g., flex beds 13) handling 300 different NDC's and two LVD's handling 504 different NDC's).

Note that a single automated pharmacy 1 can feature one or a plurality of recirculation loops 12; off of each such loop may be one or a plurality of HVD's and/or one or a plurality of LVD's 15. In one setup, a two LVD, 5 HVD (each a 20 counter flexbed) system can fill approx. 3200 orders per hour. In one setup, an LVD, which can average a 7 second cycle per fill (in certain embodiments), may have 252 S3's. A FlexBed, which in certain embodiments can average 25 sec. per fill per pill counter, may have 20 S4's that can count at the same time. Of course, these are merely exemplary, and there are a multitude of other combinations that can be used to achieve other speeds and/or meet a pharmacy's dispensing requirements. It may be that an ideal configuration, whether to achieve a fastest fill rate or otherwise, may include one or more dispensary (e.g., HVD and/or LVD) that includes fewer than a full capacity number of counters 22. Indeed, variation among the particulars for the dispensaries used (e.g., variations in the number of counters for each, robot speed, etc.), in addition to other system particulars (e.g., conveyor speed), can also achieve different system-wide order-per-hour speeds and/or meet particular facility or customer needs.

The robot 31 of the robotic dispensary 14 may, but need not, be a 6-axis robot. It may have a base, robotic arm 28 and end effector 29 (e.g., including a gripper 53 such as two prongs that can move together and apart (and also possibly roll) to grasp and release a bottle) at the end of the arm, among having other features typical of, e.g., pick-and-place robots. It may be established on the floor in a central region 59 that may be defined by the robotic dispensary, although this is not an absolute requirement, as an overhead robot, or even one whose base is outside of any space defined by the counters' configuration could possibly be used, as long as its end effector 29 can access locations of the bottle reposition cycle required by the various orders to be filled by the dispensary.

Any issue or problem during the handling, conveyance and filling of the bottle, may trigger the conveyor 4 to divert that bottle (and any puck) to an exception station 74 where, e.g., a pharmacist may determine the nature of the error and how to rectify it.

Security may be an important part of the automated order fulfillment process, and typically is very important when orders are for pharmaceutical drugs/medications. Whether it be to assure that the proper medication for a particular order is dispensed into the bottle associated with that order, to assure acceptably minimal or no-cross-contamination, or for other reasons (e.g., to prevent theft/tampering of medication), automated pharmacies 1 may require certain steps to provide and even enhance security. Such steps may include but are not limited to Pharmacist Verification 1 (PV1) and possibly even Pharmacist Verification 2 (PV2). PV1 may focus on assuring that the correct medication is placed into an external hopper 23 for a counter 22 that is dedicated to that medication (counter-to-medication dedication helps to prevent cross-contamination (i.e., a filled bottle for a certain intended medication that has unacceptably high traces of a second medication)); PV2 may focus on assuring that the correct medication is placed into a bottle (i.e., the medication of the order that the bottle is associated with). Certain embodiments of the inventive technology, in eliminating manual (i.e., human-achieved) reposition of the bottle to the correct bottle fill site 9 for dispensing of counted pills from the counter into the bottle, may eliminate the need for PV2. Indeed, the robot, and the "robotic bottle reposition cycle operation" that it enables, in eliminating the unavoidable risk of human error associated with manual operation, may allow the elimination of the PV2 security check. Note that it may be that what also is important in eliminating PV2 is the performance of some sort of performance/quality assurance step during or before the processing of an order (e.g., electronically assuring, via, e.g., RFID of, e.g., SKU's, or otherwise, that the medication of the order associated with a bottle matches with the medication of the counter whose associated bottle fill site 9 the bottle is repositioned to for filling).

As mentioned, a high bottle fill/hour (equal to order fill/hour) rate can be important in meeting processing goals, reducing costs, meeting client demands and/or minimizing equipment needs. While many factors may contribute to such rate, e.g., simultaneously counting by counters 22 as often as possible (or at least in a way that does not result in idle robot time), relatively fast conveyor speed, reduced bottle transport distances for bottle reposition cycles, intelligent, computer controlled bottle queuing, high bottle labeling speed and/or filled bottle packaging speed, in addition to possibly multiple counters for a certain medication and the high counting speed of such counters, embodiments of the inventive robotic dispensary technology disclosed herein may seek to achieve gains in order fill rates in other ways. The following factors may receive additional descriptive treatment herein:

- eliminating the need to delay movement of the end effector 29 at the fill site (or at any point in a bottle reposition cycle) due to incomplete counts when an empty bottle arrives at the fill site, as discussed;
- reducing total end effector 29 travel time during a robotic dispensary order cluster 21 by dynamically repositioning counters based on anticipated (and likely known) frequency of bottle reposition cycles to that counter during that cluster; and
- using bottle fill "wait" times for the end effector 29 (during which an end effector 29 and a bottle held thereby are stationary), when positioned in a bottle fill site 9 and being filled with counted pills during a dispensing event, that are specific for a certain order/bottle/bottle reposition cycle.

One way in which processing speed (order fill rate) may be enhanced is system configuration so that, without delay during or between the bottle reposition cycles (of a dispensary order cluster), all of said certain number of pills for said bottle-associated pill order for each of the bottles are counted and reserved in the bottle-associated counted pill reserve container 32 when the bottle arrives, via robotic transport, at the bottle-associated fill site 65. Preferably, the end effector 29 will reposition an empty bottle associated with the bottle reposition cycle to the bottle-associated fill site only after all of the certain number of pills for the order associated with that bottle are counted and reserved in the appropriate bottle-associated counted pill reserve container 66, without requiring any robot idle at all (during or between cycles) to do so. In this manner, there is no need for the end effector 29 (which secures/holds the bottle in some manner) to wait idly (generally, to idle) at any time during a bottle reposition cycle (including while it is at the fill site) or between such cycles for the bottle it is securing to be filled with appropriate number of pills (robot/end effector 29 waiting at a bottle fill site 9 during a single dispensing event is not considered idling or delay, but waiting beyond that time, for additional fill events, is). Indeed, instead of waiting for any additional counting, all pills for an order are in the reserve container 32 and will dispense from that container into the bottle in one single pill dispensing event, e.g., in a single "pill-slide" (i.e., the order is counted ahead, or "pre-counted"). And an empty bottle will preferably be waiting for the robot 31 to pick it up without the robot having to wait before such pick-up (i.e., there is no delay during or between bottle reposition cycles, e.g., after dropping a filled bottle off at a bottle placement site 10, during which the robot must wait for an empty bottle to be present at the bottle pick-up site 8 so that it can pick that bottle up).

Of course, such bottle queuing is typically the result of intentional system configuration, including but perhaps not limited to a conveyor recirculation loop 12 that is configured to divert an empty bottle at (one of) at least one recirculation loop diversion site at an appropriate time so that each empty bottle, without any delay during or between any of the bottle reposition cycles (waiting for a single dispensing event (e.g., a single "pill-slide") is not considered delay), arrives at an appropriate bottle fill site 9 only after all pills for the associated order are counted. One way of achieving this may be diversion of an empty bottle from a recirculation loop that occurs only after a count for the order associated with that bottle is complete and waiting in the reserve container 32 for the counter 22 associated with that order and bottle. However, it may be that the diversion of a bottle occurs before all pills of an associated order are counted, but that the diversion occurs late enough such that, with no delay during or between any bottle reposition cycles, that diverted bottle arrives at the appropriate bottle fill site only after all pills for that order are counted.

Of course, for high processing speeds as desired it may also be important that counters 22 start a new count for a subsequent order for that counter's medication as soon as possible, or at least sufficiently soon after a prior dispensing event for a prior order filled by that counter. Note that there may be many different queues 46 that result in no (or acceptably low amounts, or minimal amounts of) robot idle time (i.e., there are different orders in which bottles can be filled to achieve acceptable processing times). Generally, such is one manner in which order fill per hour rates can be increased.

What also may be important in avoiding any robot delay/idle due to a need to wait idly for all pills required by an order to be dispensed into a bottle (and thus achieving a high order fill rate), is the use of an appropriately large counted pill reserve container. Indeed, if the volume occupied by an order's mandated number of pills of a certain type (i.e., of a certain medication), is larger than the internal volume of a reserve container, then delay, at a bottle fill site 9, associated with additional dispensing events for a single bottle/order will be unavoidable regardless of how much pre-planning, coordination and communication takes place. Even if a few orders are larger than the volume of a reserve container, the required delay while the end effector 29 is at the fill site may very well be unacceptable. Accordingly, the use of an appropriately large reserve container, i.e., one having "full capacity" (one with an appropriately large internal volume (between a door 52 to the reserve container 32 and the counter 22), e.g., so that all 100% of orders (e.g., of all anticipated dispensary order clusters) can be pre-counted and contained in a reserve container) may be important in achieving speed-related goals. Without such full capacity bottle there may be a required delay during a bottle reposition cycle (more particularly while a bottle is at a bottle fill site 9) in order to "wait" for the additional dispensing event(s), after the initial dispensing event (i.e., the initial pill slide), where the bulk of the pills would typically be dispensed. For example, if an order calls for 80 pills, and 60 of such pills fill the internal volume of a counted pill reserve container, after the initial "pill slide" in which 60 pills are dispensed into the bottle, then there will be a need to wait for at least one additional dispensing event for the additional 20 pills to be dispensed into the bottle to fulfill the order; regardless of how those additional 20 pills are counted and dispensed (typically that would be 20 different additional dispensing events), there will be a need for at least one additional dispensing event, which will take some amount of time, particularly when the counting time is included. In view of the volumetric size of orders that one can expect to meet during appropriate and beneficial use of a robotic dispensary 14 in accordance with particular embodiments of the inventive technology, a reserve container with at least a 200 cc internal volume may be preferred (i.e., an at least 200 cc counted pill reserve container as shown, e.g., in FIG. 9). And in the interest of conserving space and materials, a 200 cc reserve container 32 may be ideal. In a typical robotic configuration (e.g., LVD and/or mid-range volume dispensary, although a robotic dispensary could be used for any orders irrespective of volume), reserve containers 32 of 200 cc may be sufficient to achieve a 100% pre-count rate. Other embodiments may provide for an at least 120 cc reserve container, an at least 150 cc reserve container, an at least 180 cc reserve container, and at least 190 cc reserve container, and an at least 210 cc reserve container, to achieve an acceptably high precount rate (e.g., at least 95%, at least 98%, or 100%).

Figure 24:
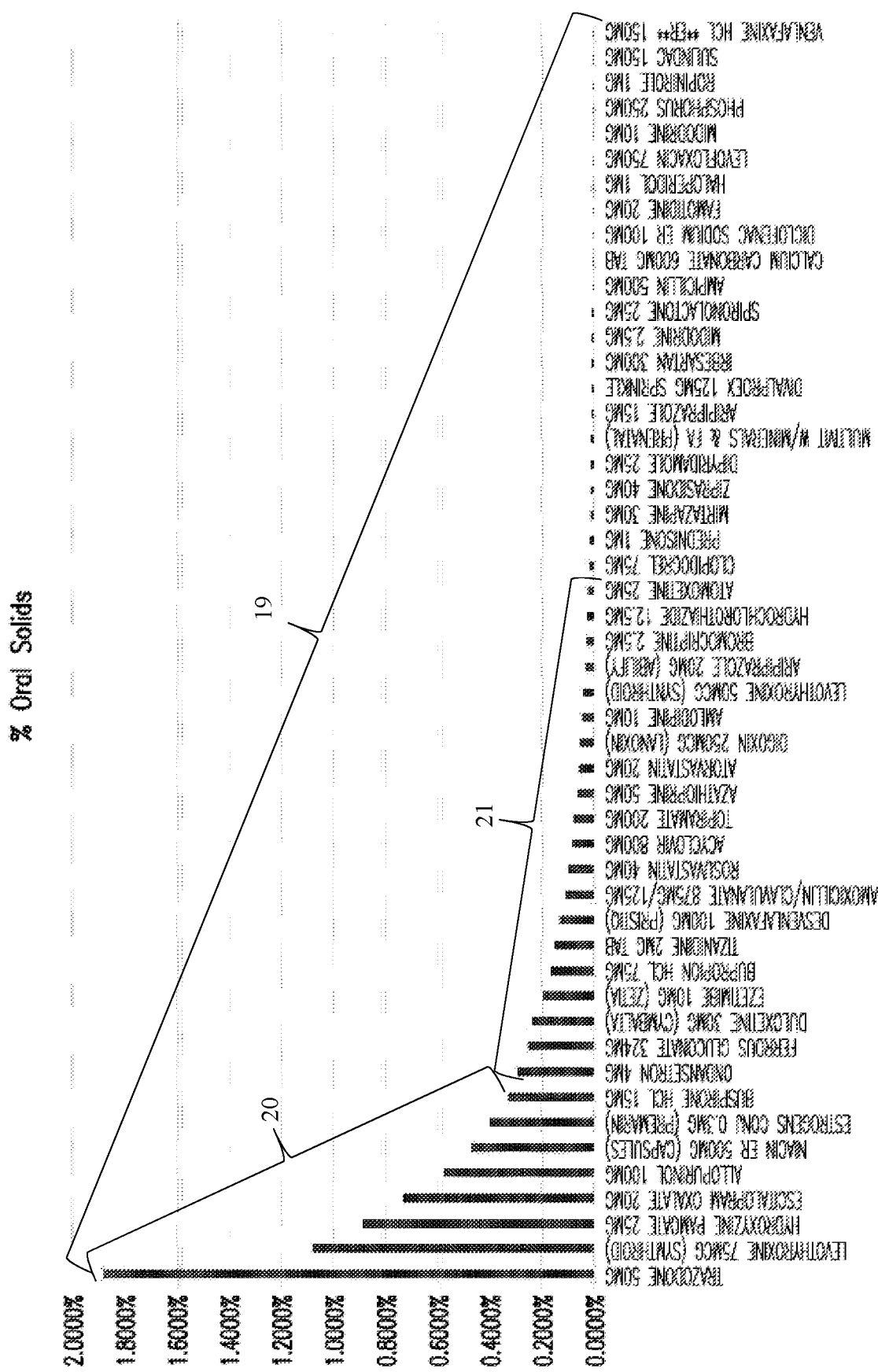
FIG. 24 shows a graph of frequency (anticipated number of orders (volume)) of a system wide order cluster 19 for approx. 450 medications; only 50 or so (e.g., every 9th or so medication) are named in the horizontal axis because of page size constraints.

Another way in which certain embodiments of the robotic dispensary 14 may achieve gains in order/bottle fill speeds is reducing total end effector 29 travel time during processing of a dispensary order cluster 21 by allowing for dynamic repositioning of counters 22 based on anticipated/known frequency of bottle reposition cycles to particular counters during that cluster; such may be based on medication volume (see, e.g., FIG. 24). The reason for such dynamic readjustment may stem from the fact that, for a particular dispensary order cluster, there may be different numbers of orders for different medications (e.g., there may be 120 orders for medication x (and thus 120 bottle reposition cycles for that medication's dedicated counter) but 20 orders for medication y). Note that each counter space 17 has associated with it a particular bottle reposition cycle time, which is the time elapsed during robotic repositioning of the end effector 29 from a bottle pick-up site 8 to the bottle fill site 9 associated with a counter located in that counter space, then to a bottle placement site 10, then back to the bottle pick-up site. Note that the "bottle reposition cycle time" or "average bottle reposition cycle time"—whether discussed with regard to a counter or counter space, a set of counters or counter spaces (e.g., a set of 7 counter spaces side by side on the same tier), a sector 57, which may be, e.g., one or a set 56 or sets of such counter spaces, or with regard to a sub-array 76 of counters—ignores variations in bottle fill wait times, and simply assumes an average time for such wait times. In order to reduce total robot end effector 29 travel time during the processing of that dispensary order cluster, the counter(s) for medication X will preferably be placed in a counter space(s) that has associated therewith bottle reposition cycle time(s) that are less than those associated with a space(s) in which the counter(s) for medication Y are located. But the next dispensary order cluster (whether to be processed on the same day for the previous dispensary order cluster or not) may present with a different medication frequency profile/landscape (perhaps presented as a graph), e.g., where there are fewer (possibly significantly fewer) orders for medication X than there are for medication Y.

Note that a cluster may be anticipated orders coming in; they may be handled substantially sequentially, often during one straight time period (e.g., in 0.5 hour, in an 8 hour "shift," the next 1000 orders, orders from ABC Insurance Co., as but a few examples); a system-wide order cluster 19 is a set of orders to be handled by a single automated pharmacy 1 while a robotic dispensary cluster 21 is a set of orders to be handled by robotic dispensary(ies) 14). That anticipation may be entirely accurate, as where it is based entirely on actual orders received (from, e.g., medical facility, insurance company, etc). It may be different (preferably only slightly so) from the set of orders actually processed, particularly where it is based, at least in part, on something other than exact orders received, e.g., where it is based at least in part on knowledge of order history of a customer, of a time of year (e.g. flu vaccine medications in winter), geographic location of ordering entity, etc. Similarly, the medication frequency profile for an order cluster (discussed further below) may be similarly anticipated (and may, at times, be at least in part based on, e.g., history, time of year, geographic location of ordering entity, etc.) Note that there need not be a pause in processing between sequential order clusters.

Re-determination of a cluster may be achieved at any appropriate frequency, e.g., every 10 minutes, every 40 minutes, every 2 hours, every 8 hours, every few days, every 1000 orders, every 2000 orders, etc., as may be beneficial. A cluster can be of any amount of orders (e.g., 800 orders, etc.). For example, looking at 20,000 orders continuously (without pause) handled by a dispensary, a first cluster may have been determined for the first 1000 orders at 0 hours, a second cluster as to the next 1000 orders may have been determined at 1.5 hours (during processing of the first cluster), etc. Note that clusters may, but certainly need not, overlap somewhat (e.g., a single order can be a "member" of more than one cluster). Clusters may be assessed in a rolling manner (e.g., every hour a new cluster can be determined). Redetermination of a cluster (e.g., robotic dispensary order cluster 21) presents an opportunity to change position of counters in a robotic dispensary array. Any changes (e.g., in position of counters) associated with, e.g., order frequency of a certain cluster, such as position of counters, can be made before orders associated with such change are handled/processed.

As mentioned, a determination of a robotic dispensary order cluster 21 presents an opportunity to achieve gains in fill rate. More particularly, if in such example, before that next dispensary order cluster is processed, the counter(s) 22 for medication y is moved so that it is in a counter space(s) 17 that has associated therewith a shorter bottle reposition cycle time (e.g., such that it is closer to the bottle pick-up and placement sites 8, 10) as compared to its location in the previous cluster, then the total travel time for the robot end effector 29 (for that dispensary order cluster) will be decreased as compared to what it would be without such repositioning (all other things being equal). Indeed, any number of counters (dedicated to any number of medications) can be moved before the next robotic dispensary order cluster 21 is processed in order to reduce end effector 29 travel time. While the inventive dynamic repositioning technology includes the case where even only one counter is repositioned to increase an order fill rate for a particular dispensary order cluster as based on frequency of orders for particular medications of that cluster, typically several—and at times all—counters are repositioned (typically between processing successively processed dispensary order clusters (i.e., a prior, e.g., immediately prior, and an upcoming, e.g., next, cluster)) in order to increase fill rate for such next order cluster.

Note also that counters may be repositioned while the robot 31 is still handling bottles for filling (e.g., while other counters are counting), and without requiring a pause in processing by the robotic dispensary 14. To achieve this, there may be a need for some coordination to assure that counters that are moved are not counting and discharging into reserve containers 32 when they are moved. The system would typically be configured to adapt to the new location of the counter(s) after they are moved so the dispensary can use that repositioned counter to fill orders.

A "heat map", as shown in FIG. 24, which shows an (anticipated) medication frequency profile of what could be a system-wide order cluster 19, may be helpful in determining in which sectors 57 to place counters 22 for particular medications. It may also be helpful in determining which medications are to be handled by a robotic dispensary 14, particularly where the pharmacy includes a robotic dispensary(ies) and a non-robotic dispensary(ies) (e.g., HVD's). In the case where the profile is of orders to be handled by a pharmacy with HVD's and LVD's, then associated orders may be split among such dispensary types in any manner; typically, the HVD's would handle orders for a certain number of the more frequently ordered medications, and the LVD's 15 would handle orders for the next highest volume medications (remaining least frequently ordered medications, such as those to the right of atomoxetine in FIG. 24, could be counted via direct, non-robotic counting via technician and counter, etc.; such remaining least frequent medications are still considered part of a system-wide order even though they many not be processed by a dispensary such as an HVD or LVD). For example: orders for the top 80 most frequently ordered medications could be handled by the HVD('s); orders for the next 252 most popular medications could be handled by the LVD('s)); and orders for any remaining lowest volume could be counted via technician and counter.

In the case where the pharmacy includes only a robotic dispensary, then orders for a certain number of the most frequently ordered medications (perhaps even for all medications) may be assigned to that robotic pharmacy, divided among them in any manner (e.g., one gets the top 252 highest volume while another gets the next 252 highest volume, or remaining portion of the medications; or medications are equally split among the dispensaries). Any remaining medications not assigned to a robotic pharmacy (e.g., the remaining least frequently ordered medications) may be counted in any of several other ways, e.g., a direct, non-robotic counting via counter and technician). These are exemplary only, and a determination as to which dispensary handles which could be made with the goal of fastest, most efficient processing of the entire system-wide order cluster 19. And any number and type of dispensary could be used to handle the entire order cluster (e.g., one robotic dispensary 14, or any combination of robotic dispensary and one or more non-robotic dispensary), with orders for some least ordered (lowest volume) medications perhaps being handled via technician and counter.

Regardless, at least a part of the volume profile (e.g., FIG. 24) may be associated with orders to be handled by a robotic dispensary(ies): perhaps the entire system-wide order cluster medication frequency profile, or at least a first portion of it (e.g., a left most portion of FIG. 24), is associated with orders to be handled by the robotic dispensary, as where the pharmacy includes only a robotic dispensary(ies)); perhaps, as where the pharmacy includes both non-robotic (e.g., HVD('s)) and robotic (e.g., LVD('s)) dispensaries, only a second portion (where a first portion, from the left, is handled by a non-robotic HVD('s)) of such system wide order medication frequency profile, is associated with orders to be handled by the robotic pharmacy(ies). Regardless, the part of the ordered medication frequency profile that is associated with a robotic pharmacy can be used to determine which counters (each dedicated to a particular medication in certain embodiments) should be placed in certain different sectors 57 in order to increase order fill rate for that dispensary order cluster 21.

Regardless of how a medication frequency profile manifests, a medication frequency profile, or portion thereof, may be reflective of order frequency for medications for a particular order cluster 21 for a robotic dispensary 14 (and thus frequency of bottle repositioning, during that order cluster, to particular counters 22 because typically counters are dedicated to a particular medication). Such profile (or profile portion) can be used to guide such dynamic repositioning of counters in a robotic pharmacy; indeed, the repositioned counters can be said to be positioned, at least in part, based on such medication volume profile or such medication frequency. Perhaps counters for medications within a certain highest frequency range of orders (within that profile or profile portion) can be placed in a first sector (perhaps located on both sides of the general area of the bottle pick-up and bottle placement sites 8, 10, and bisected thereby) that has a lowest average bottle reposition cycle time (if that sector has more than one counter, as is typically the case, then such time could be an average of all times for counter spaces 17 in that sector); counters for medication within a medium frequency (lower than the highest frequency, but higher than the lowest) range of orders can be placed in a second sector (intermediate bottle reposition cycle time that is higher than that of the first sector but lower than that of other sector(s)); and counters for medication within a lowest frequency (lower than the highest and medium frequencies) range of orders can be placed in a third sector that has associated therewith a larger bottle reposition cycle time (if it's the "last" or highest number sector, then that time would be the largest of all times). For example, if the first sector has 7 counter spaces, then the counters for the 7 most frequently ordered (highest volume) of medications to be handled by the robotic dispensary 14, could be placed (in any way, e.g., randomly) in those 7 counter spaces; if sector #2 has 14 spaces, then the counters associated with the 14 next highest volume counters could be placed in that sector. Of course, other numbers of ranges and sectors 57 can be used to dynamically reposition counters in view of anticipated medication order frequency. In such exemplary manner, for a single dispensary order cluster 21, the total time and/or total time for processing of all orders of that cluster may be reduced as compared to what would be observed if all counters were left in the same position for all dispensary order clusters for that dispensary, and there were no dynamic repositioning of counters between such clusters.

Figure 4:
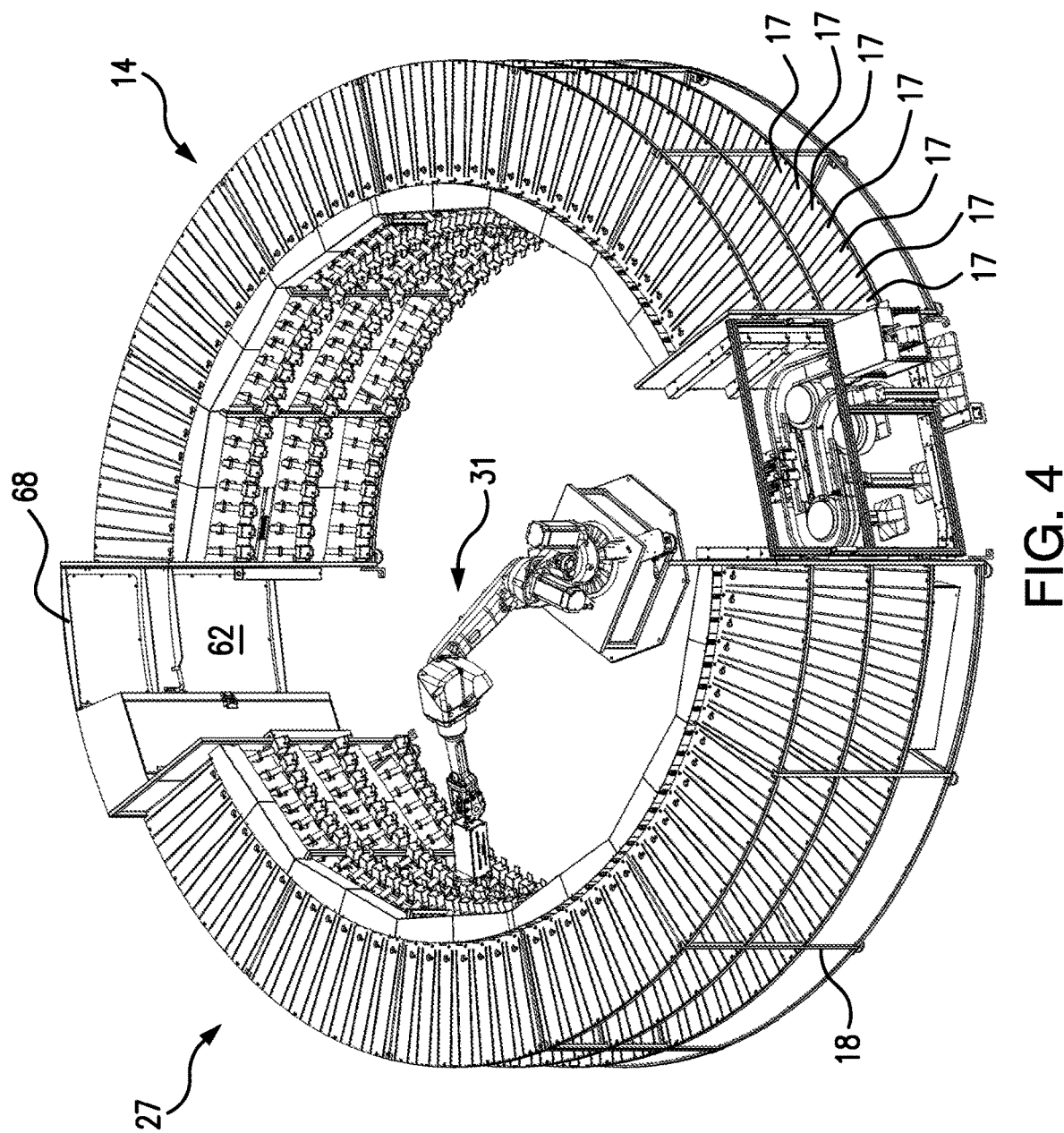
FIG. 4 shows a perspective view from above of a robotic pill dispensing system 27 (e.g., a LVD) as may appear in certain embodiments of the inventive technology. It shows a robot, with articulated arm, positioning its end effector substantially at a bottle fill site 9.
Figure 5:
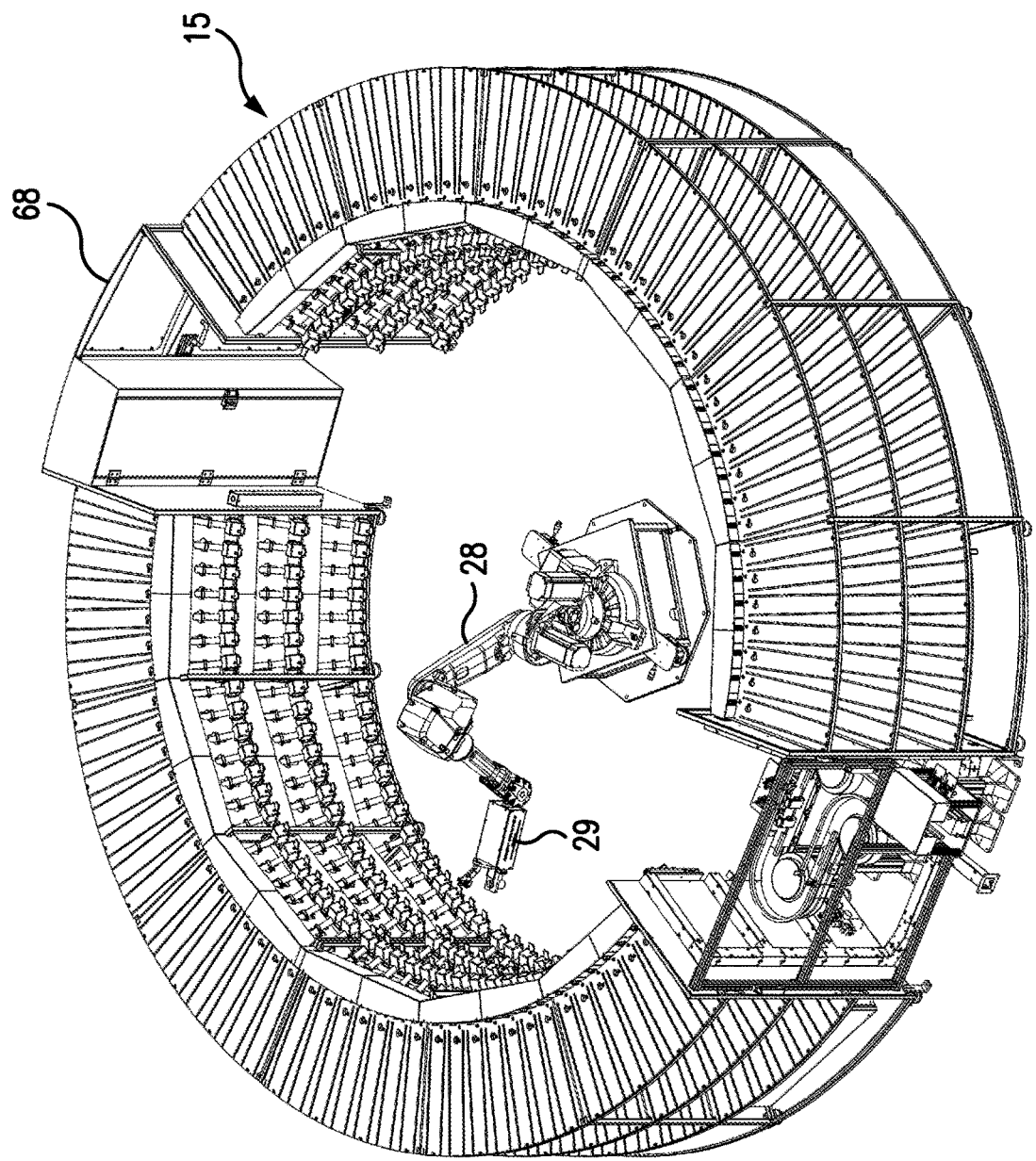
FIG. 5 shows a perspective view from above of a robotic pill dispensing system 27 as may appear in certain embodiments of the inventive technology. It shows a robot in an intermediate position between its (end effector's) position in FIG. 4 at a bottle fill site 9 and a bottle placement site 10.
Figure 6:
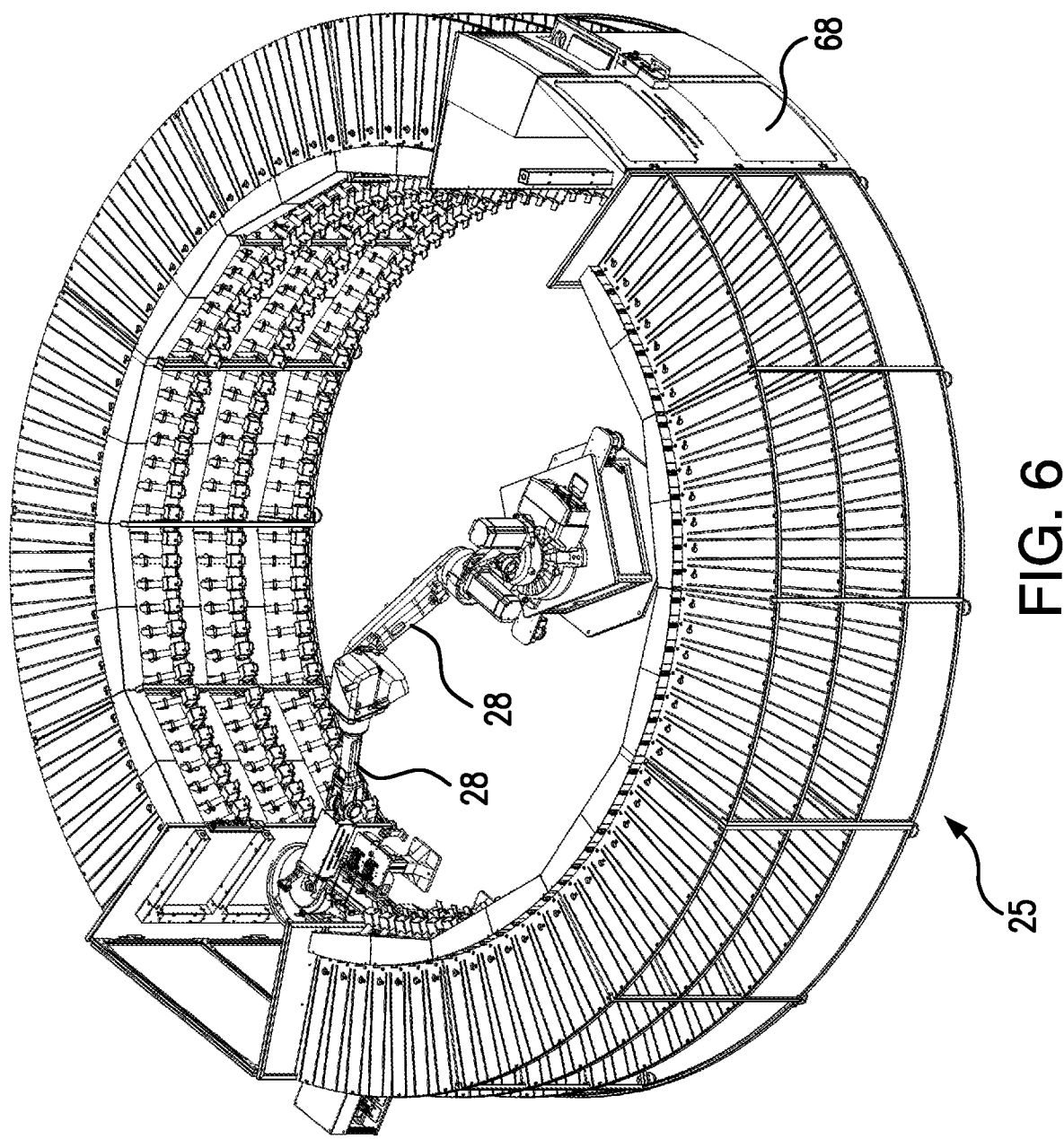
FIG. 6 shows a perspective view from above of a robotic pill dispensing system 27 as may appear in certain embodiments of the inventive technology. It shows a robot, with articulated arm, positioning its end effector substantially at a bottle fill site 9. After filled bottle placement and repositioning (of its end effector and the bottle it holds) to the (empty) bottle pick-up site 8 (here, shown immediately to the left of the bottle placement site 10), it will have completed a bottle repositioning cycle.
Figure 7:
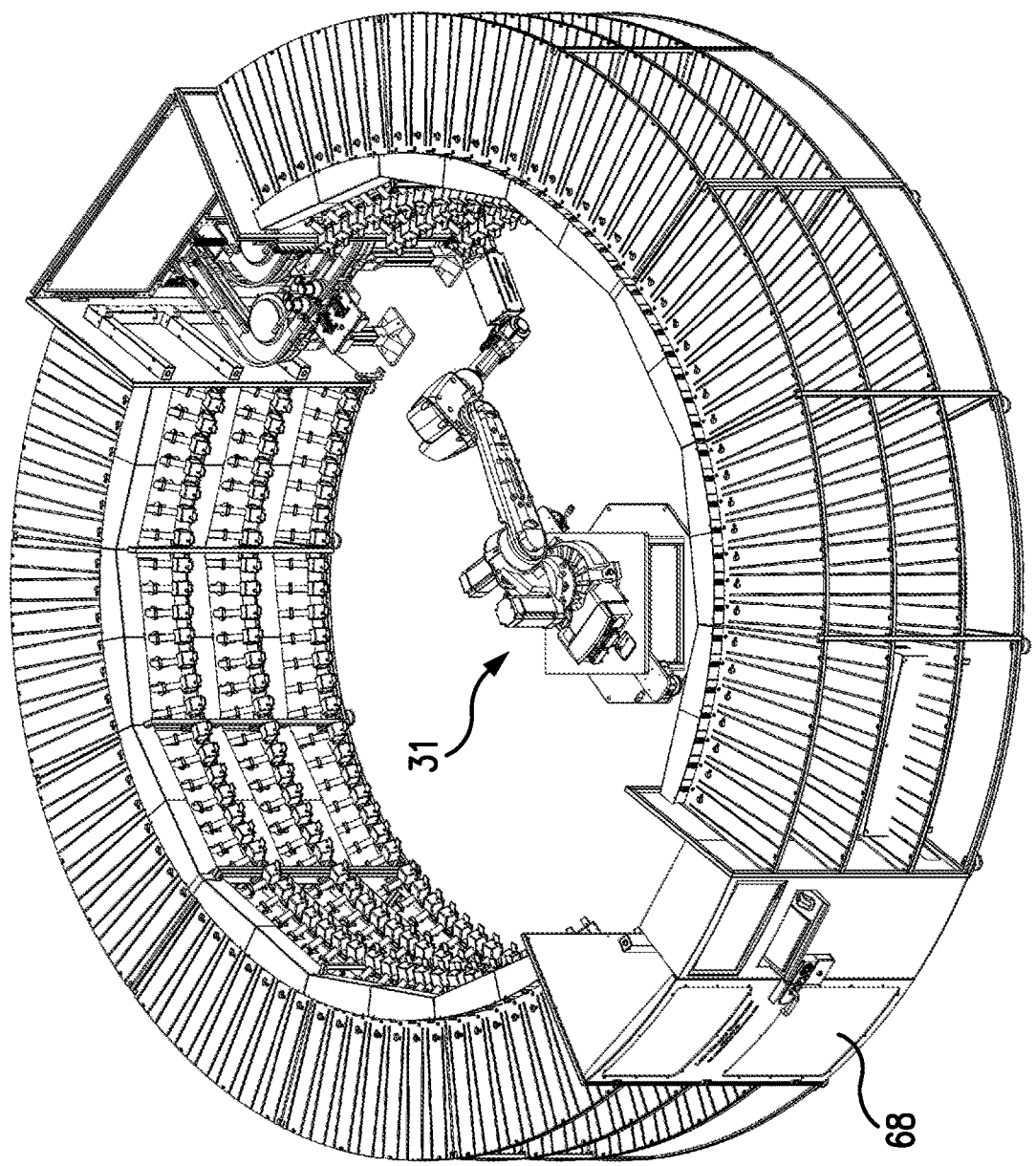
FIG. 7 shows a perspective view from above of a robotic pill dispensing system 27 as may appear in certain embodiments of the inventive technology. It shows a robot, with articulated arm, positioning its end effector substantially at a bottle fill site 9 that is different from that bottle fill site of FIG. 4.
Figure 8:
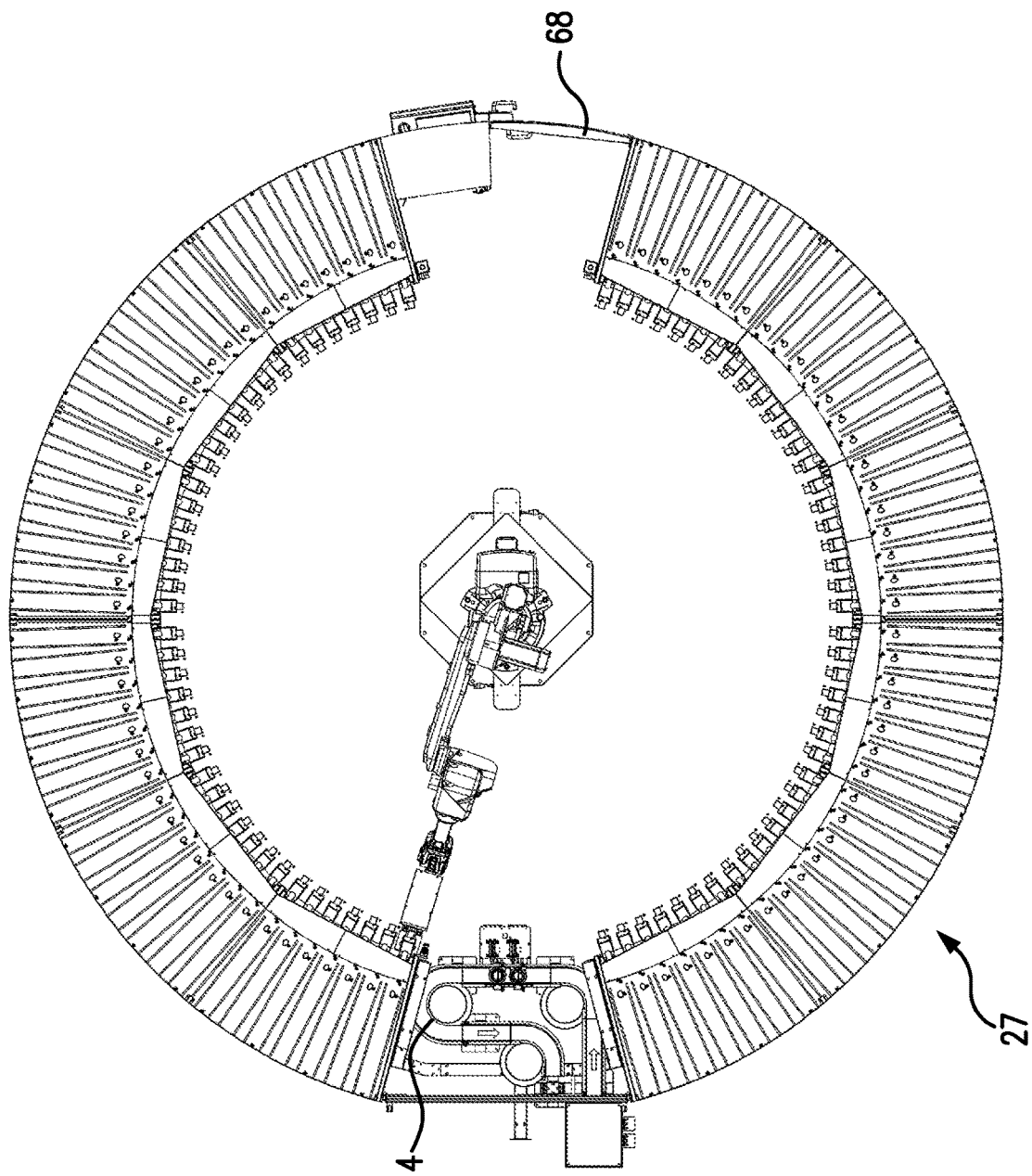
FIG. 8 shows a plan view of a robotic pill dispensing system 27 in the position shown in FIG. 7, as may appear in certain embodiments of the inventive technology.
Figure 9:
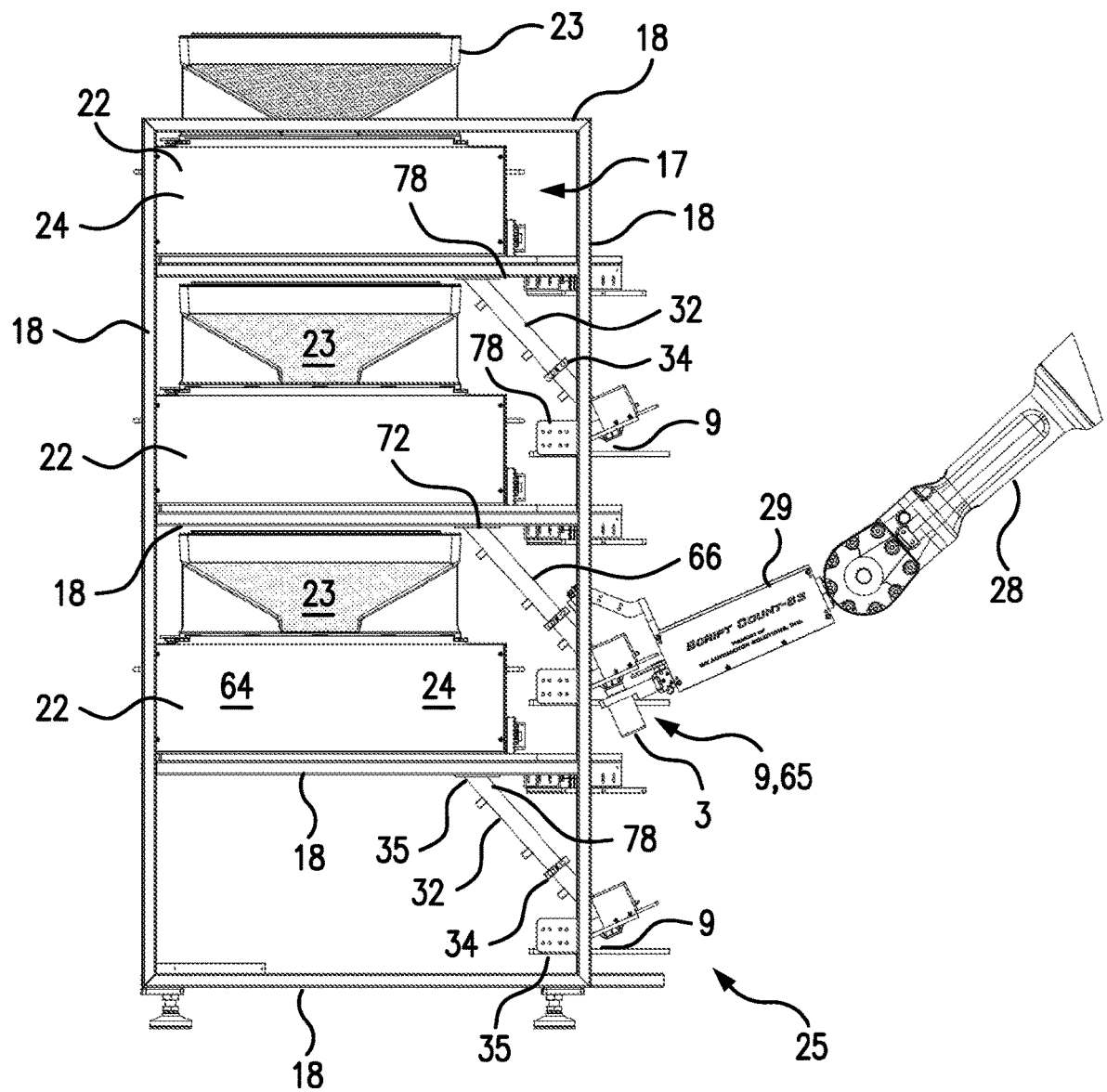
FIG. 9 shows a side view of a three-tiered robotic pill dispensing system 27 (of, e.g., FIGS. 4-8) as may appear in certain embodiments of the inventive technology. It shows three "stacked" counters, a frame on which such counters are stacked and that supports such counters, external hoppers slidingly attached atop and as part of such counters, counted pill reserve containers, and a robotic arm holding a bottle just before a dispensing event during which the bottle is filled with a certain number of pills in accordance with a pill order. It also shows a device of the end effector in position to apply lodged pill clearance forces directly to a collar around the counted pill reserve container.
Figure 10:
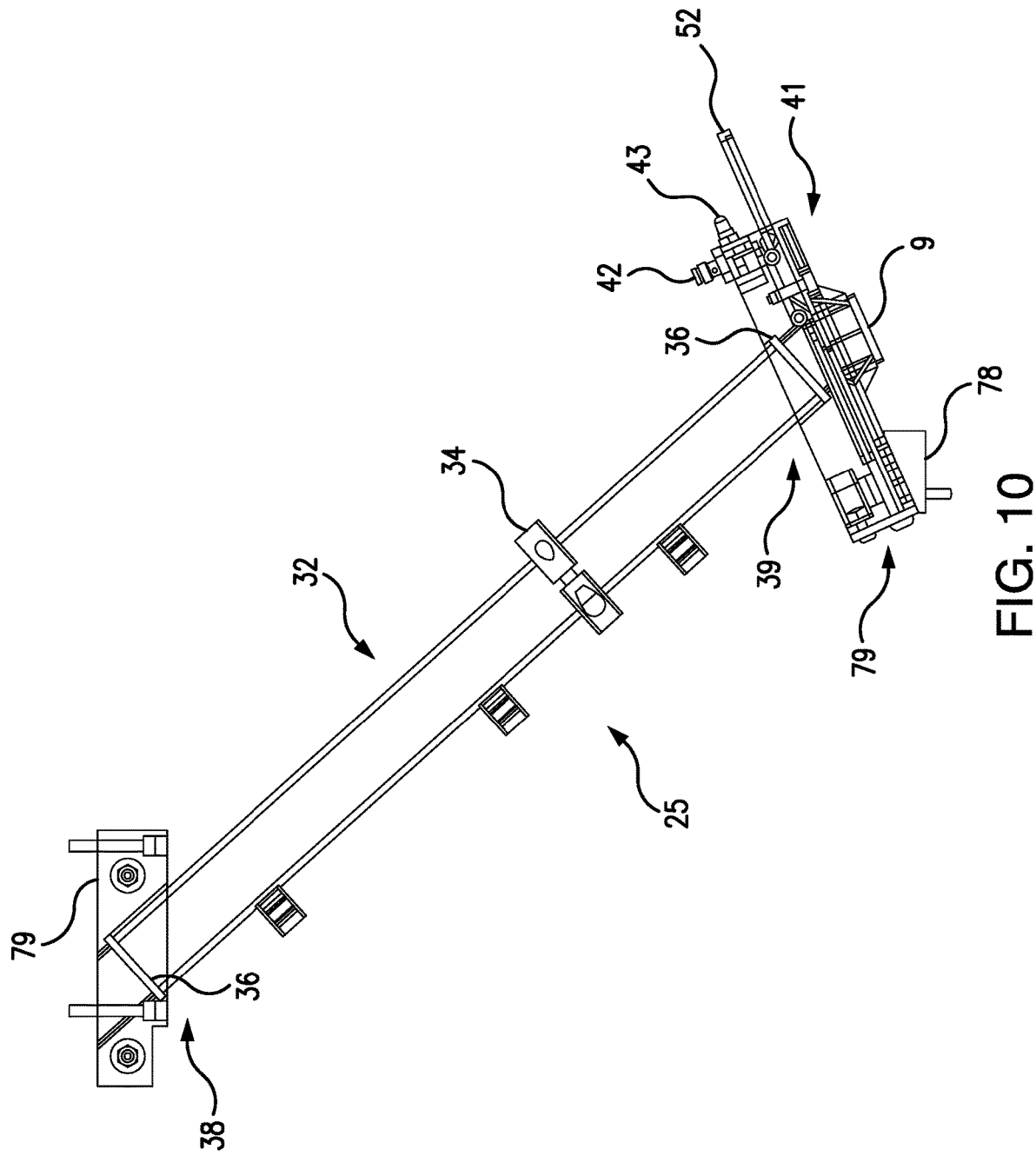
FIG. 10 shows a side transparent view of a counted pill reserve container as may appear in certain embodiments of the inventive technology. It shows attachment componentry, and an elastic component (an o-ring) at each the upper and lower ends of the counted pill reserve container. It also shows reserve container door componentry, a door proximity sensor to verify door closure, and a visual indicator (an LED) that is particularly helpful during manual mode to signal to a human operator where the next bottle fill site 9 is located.
Figure 11:
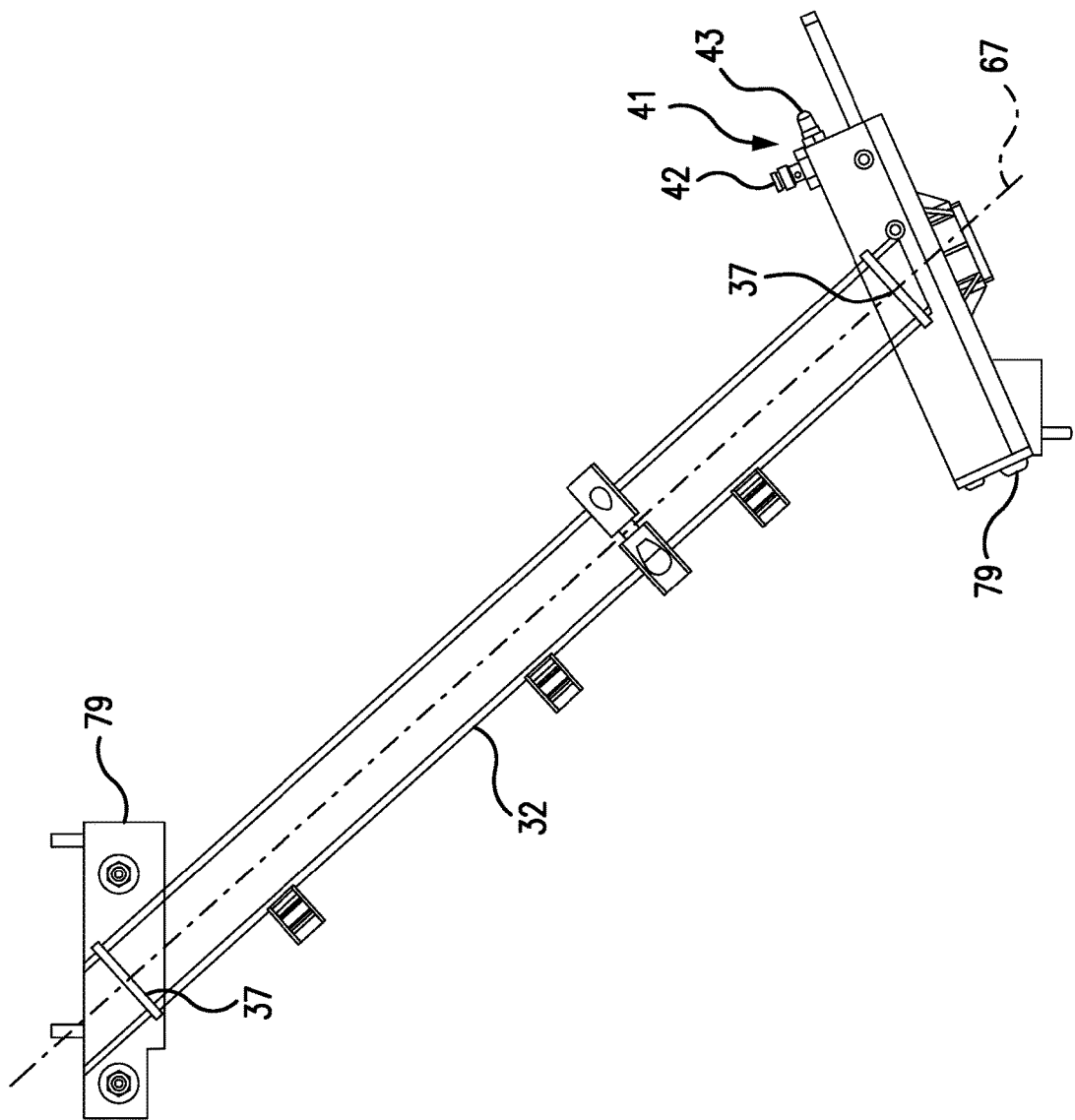
FIG. 11 shows a side transparent view of a counted pill reserve container as may appear in certain embodiments of the inventive technology. It shows componentry listed immediately above in the description for FIG. 10.
Figure 12:
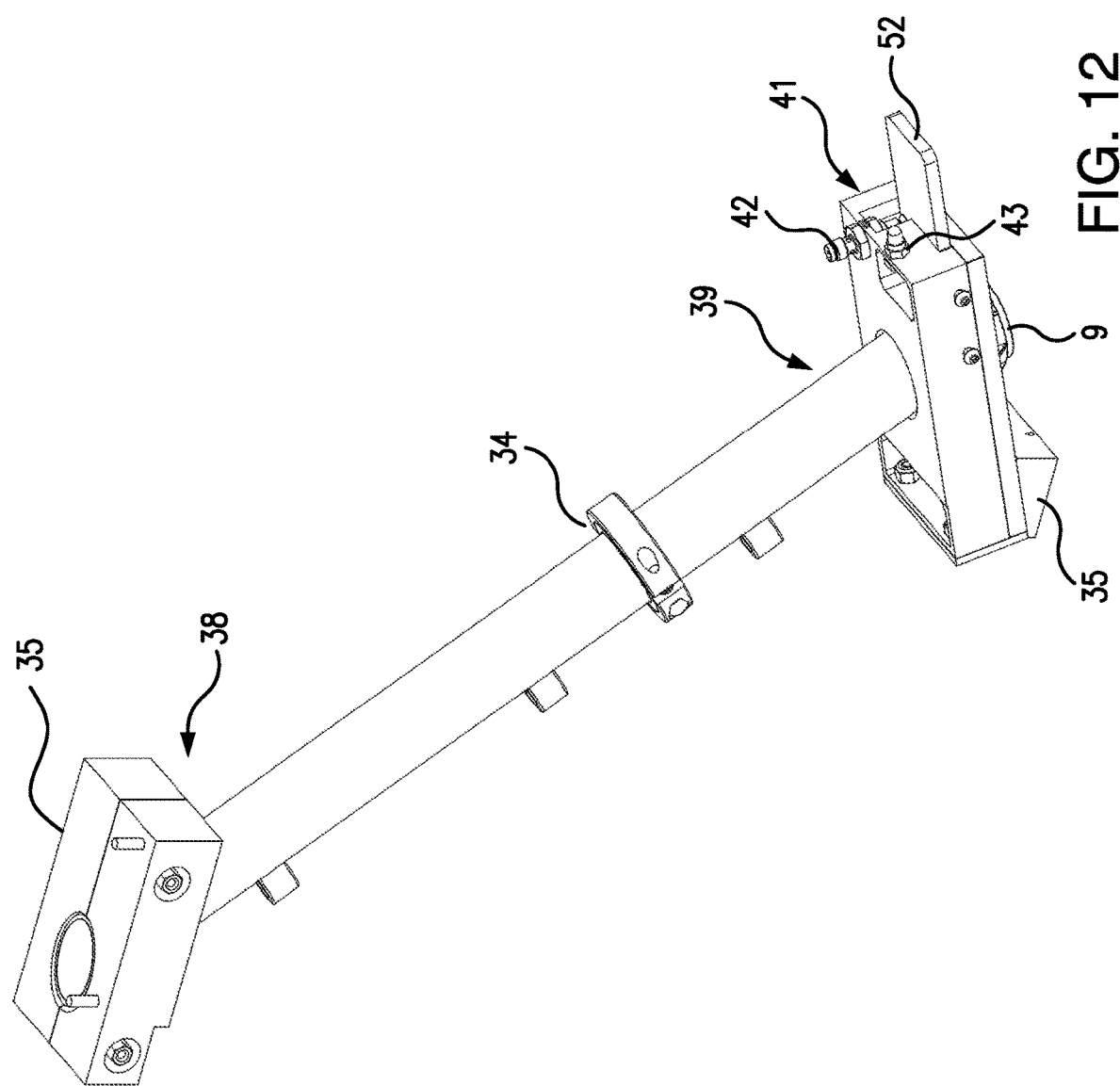
FIG. 12 shows a side view of a counted pill reserve container 32 as may appear in certain embodiments of the inventive technology.
Figure 13:
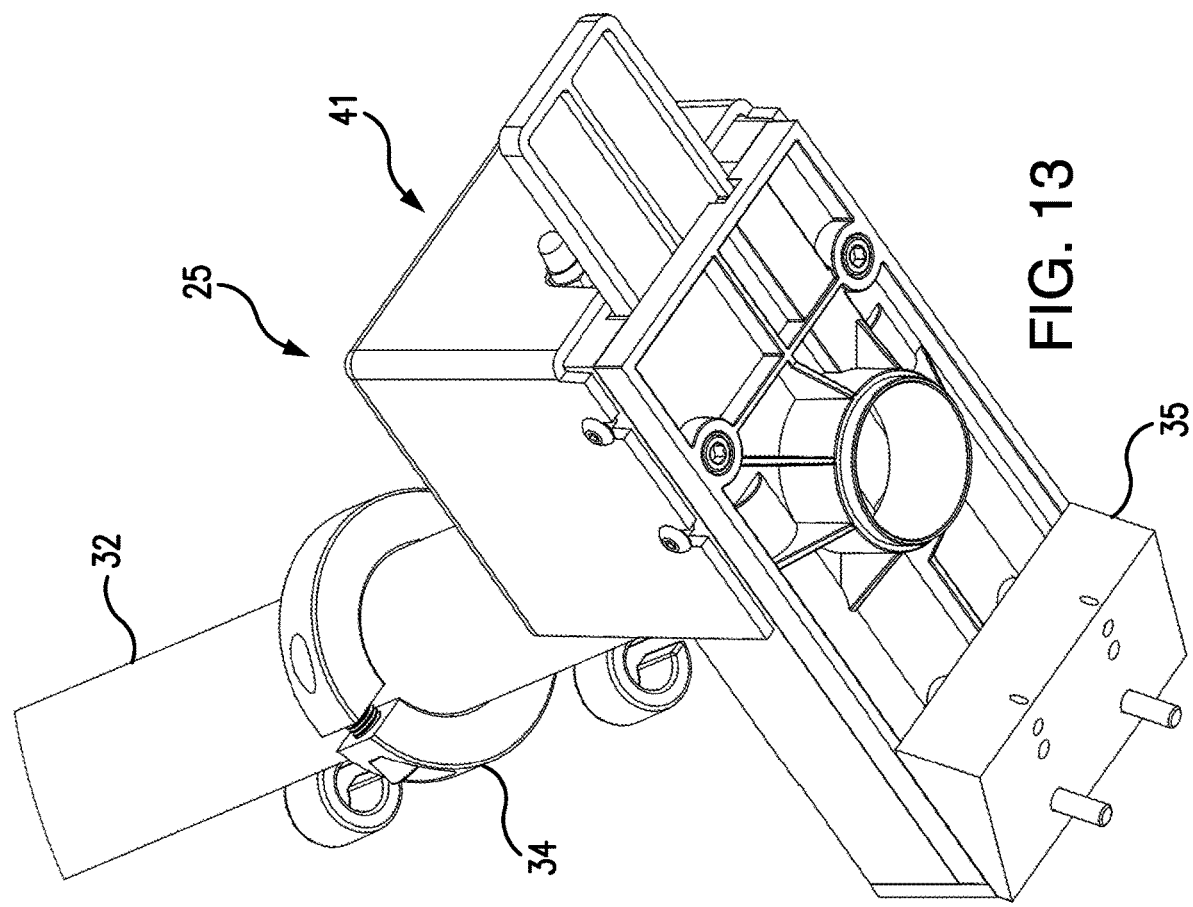
FIG. 13 shows a perspective view from below of the lower end of a reserve container 32, and door componentry established at that lower end.
Figure 14:
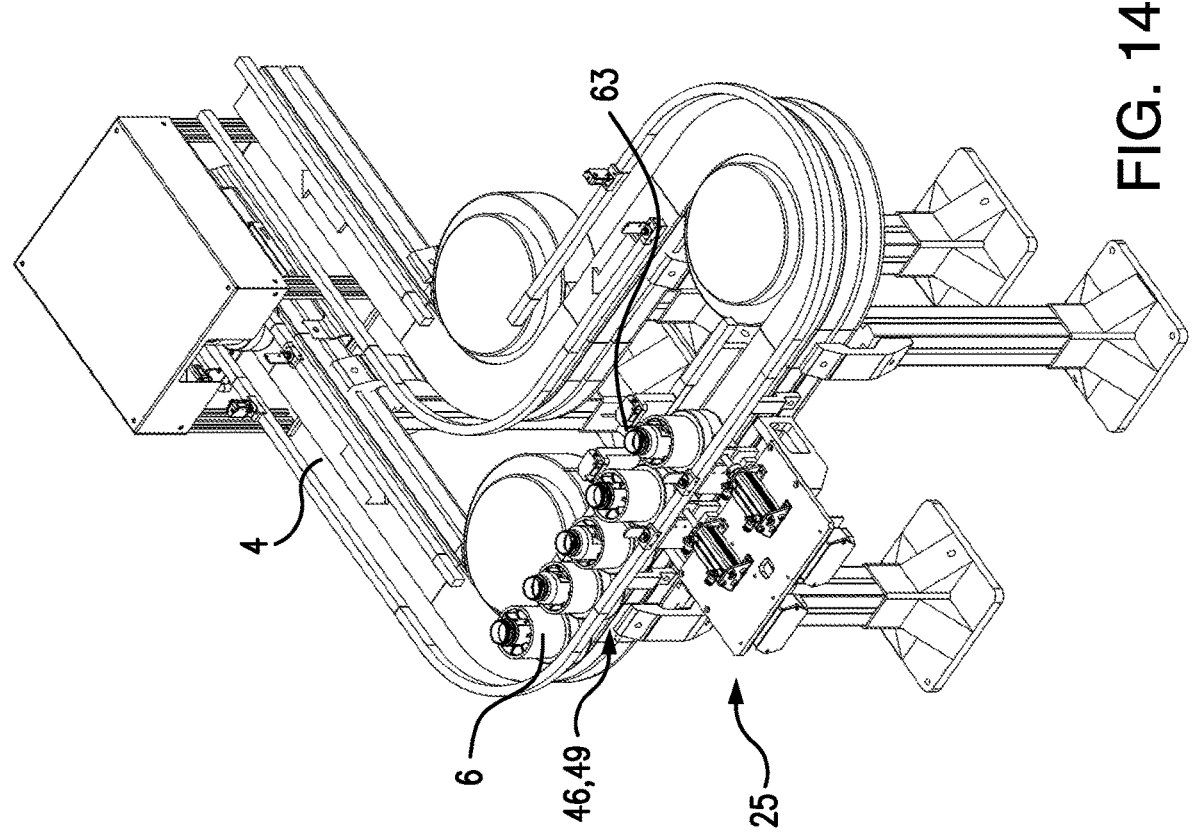
FIG. 14 shows a view of a (empty) bottle pick-up site 8 and a (filled) bottle placement site 10, a portion of the conveyor that leads to and from such sites, a first and second bottle obstructers 44, 45 (or portions thereof), and a queue 46 of bottles (and their associated pucks) as appears (here, in isolated manner) in particular embodiments of the inventive technology. This is an example of what may be seen immediately in a puck-based system after a filled bottle is dropped off into a puck at the bottle placement site, but before the robot has picked up an empty bottle at the bottle pick-up site.
Figure 15:
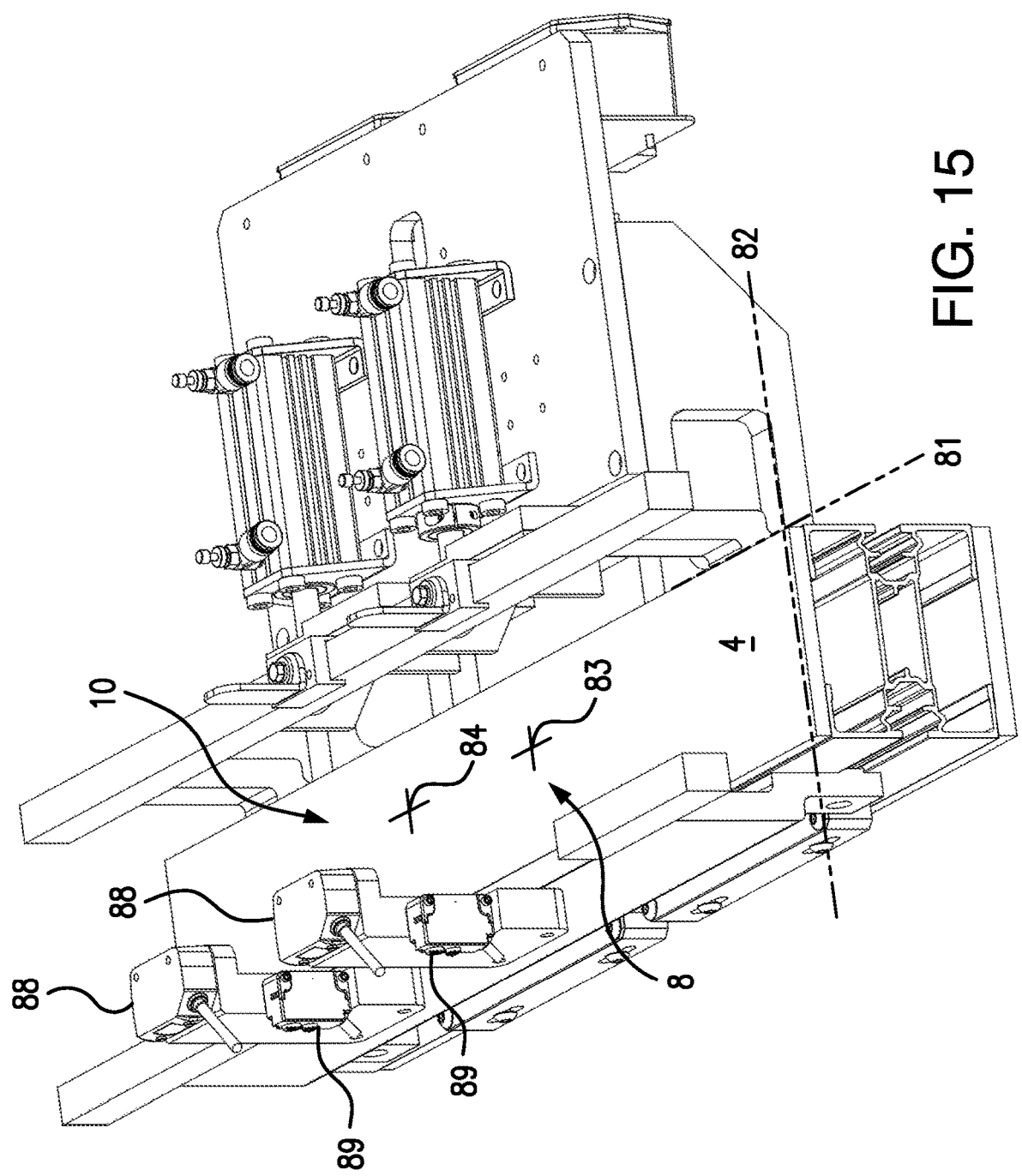
FIG. 15 shows a perspective view of a bottle pick and placement sites 8, 10, as isolated from other system components, as may appear in certain embodiments of the inventive technology. No bottles (or pucks) are shown, for clarity. This figure shows the first and second bottle obstructers in retracted configuration.
Figure 16:
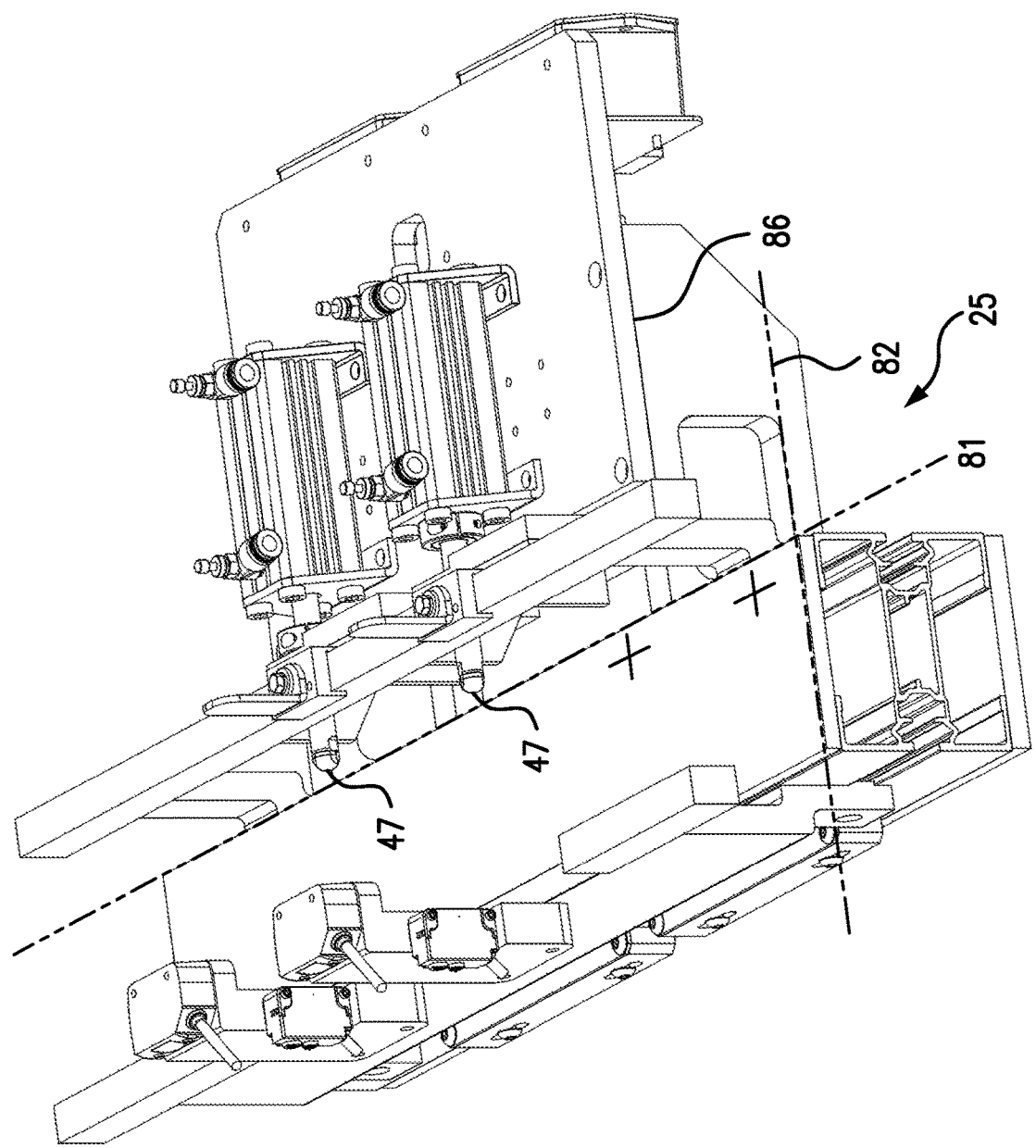
FIG. 16 shows a perspective view of a bottle pick and placement sites 8, 10, as isolated from other system components, as may appear in certain embodiments of the inventive technology. No married bottles (or pucks) are shown, for clarity. This figure shows the first and second bottle obstructers (which may actually contact only the puck in puck-based systems) with only part of the obstructers—pins—extended, but with wedges retracted.
Figure 17:
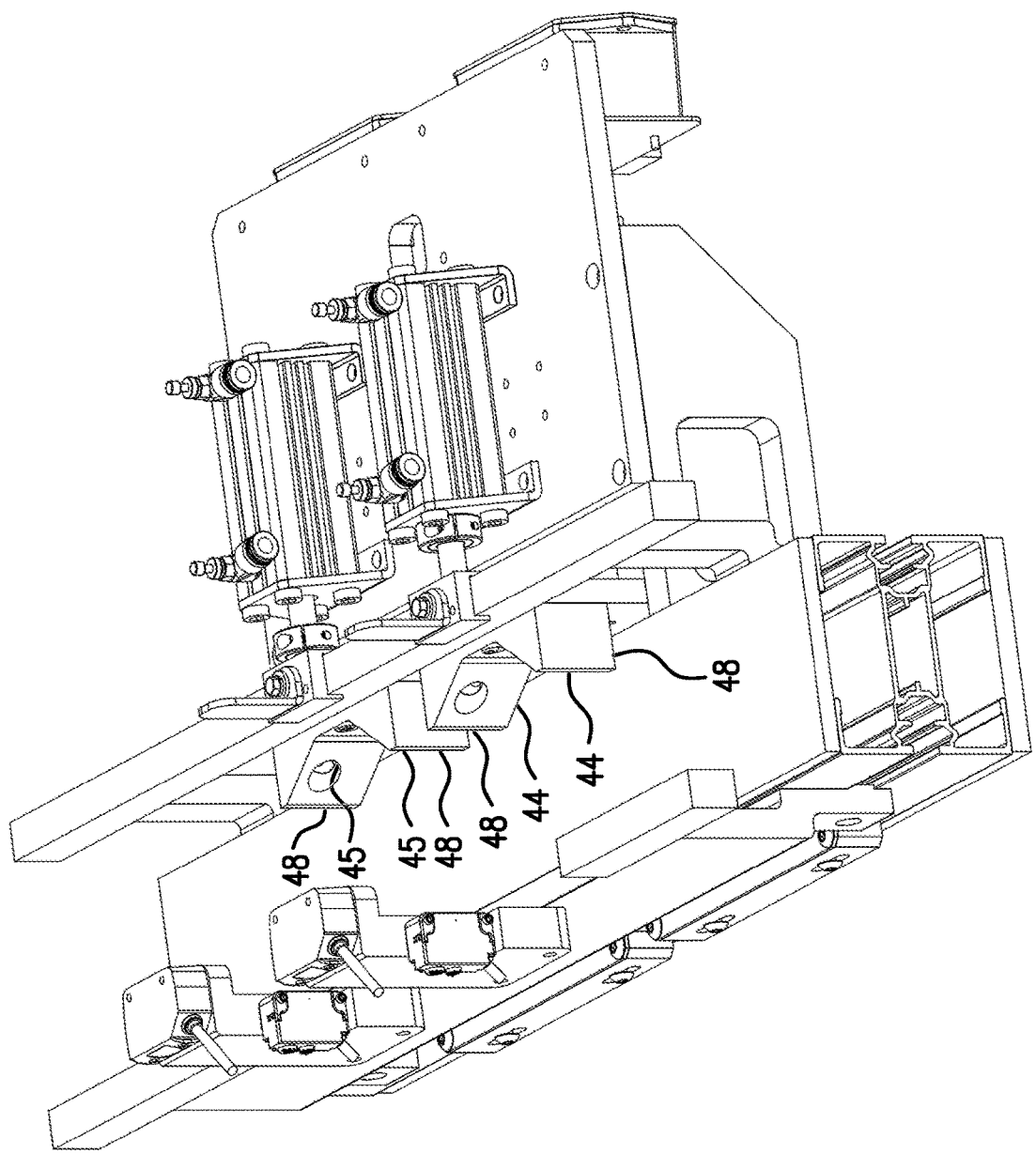
FIG. 17 shows a perspective view of a bottle pick and placement sites 8, 10, as isolated from other system components, as may appear in certain embodiments of the inventive technology. No married bottles (or pucks in puck-based systems) are shown, for clarity. This figure shows the first and second bottle obstructers with both pins and wedges extended.
Figure 18:
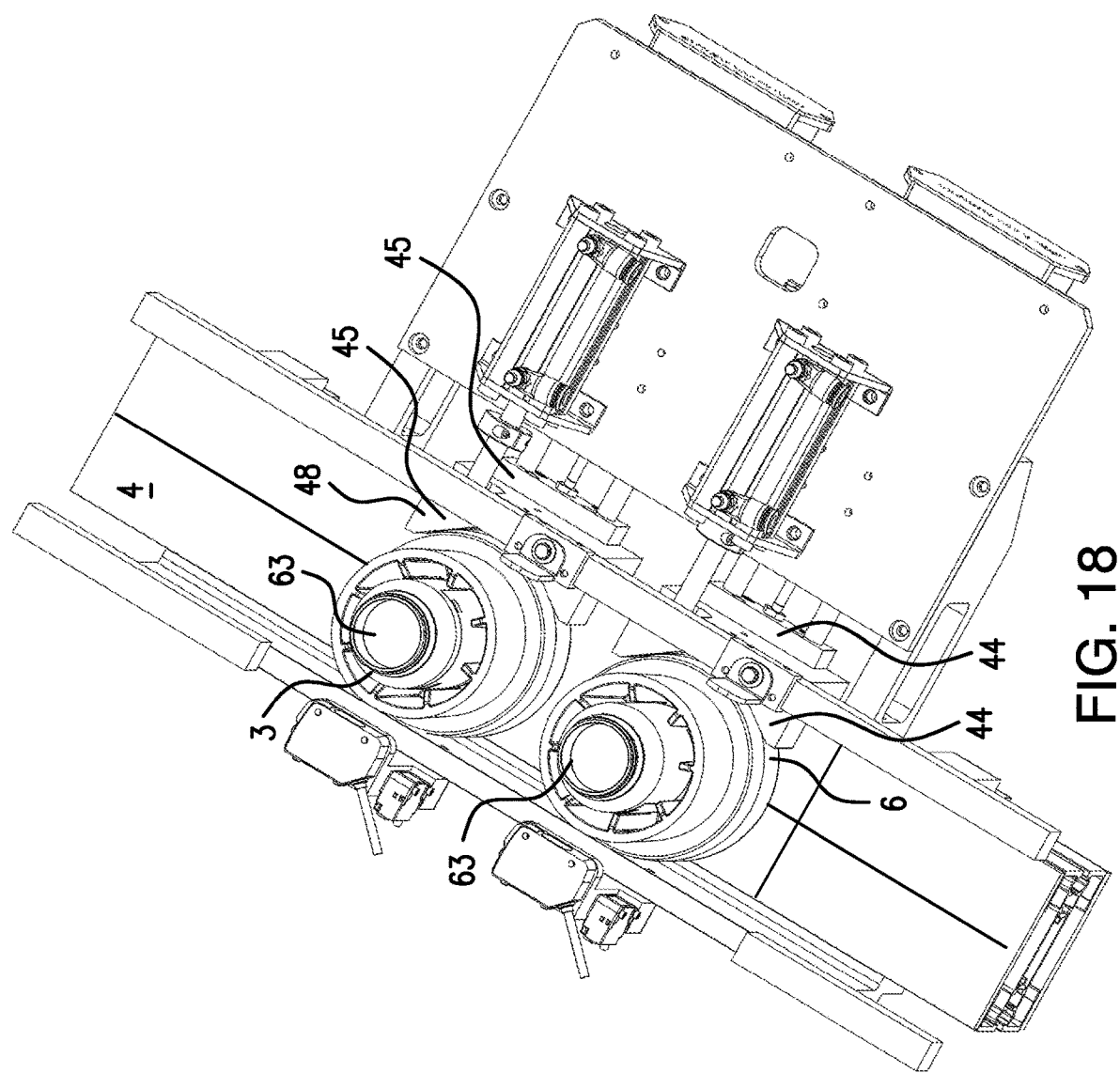
FIG. 18 shows a perspective view of a bottle pick and placement sites 8, 10, as isolated from other system components, as may appear in certain embodiments of the inventive technology; a married bottle and puck is shown at each site. This figure shows the first and second bottle obstructers with both pins and wedges extended.
Figure 21B:
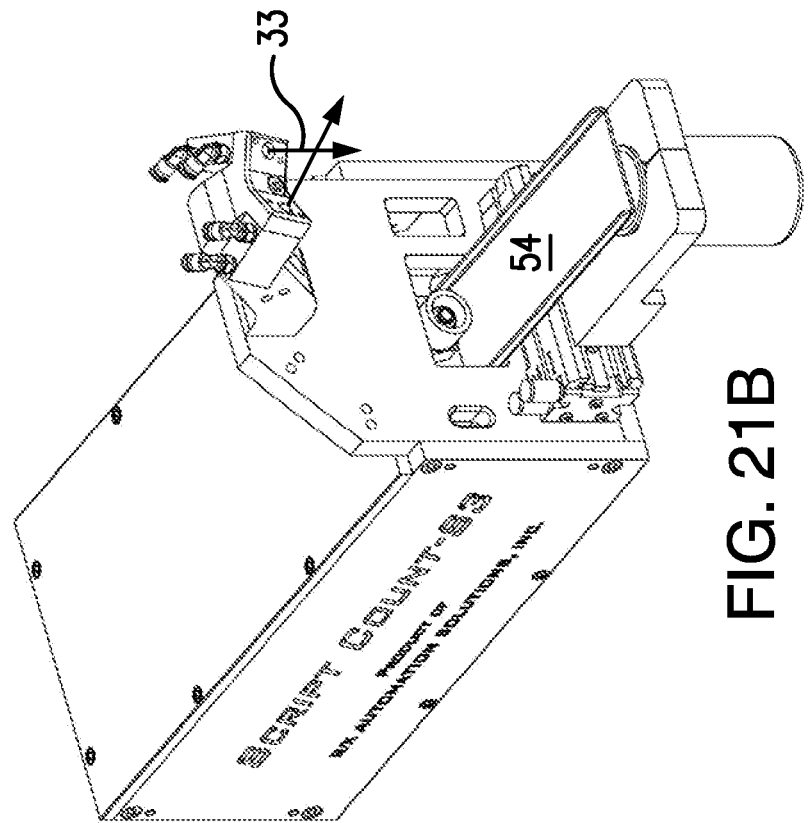
FIGS. 21A and 21B show a perspective view of an end effector (of the robot) as may appear in certain embodiments of the inventive technology, with an extendable rod in retracted mode and gripper closed around a bottle neck in order to hold that bottle.
Figure 21A:
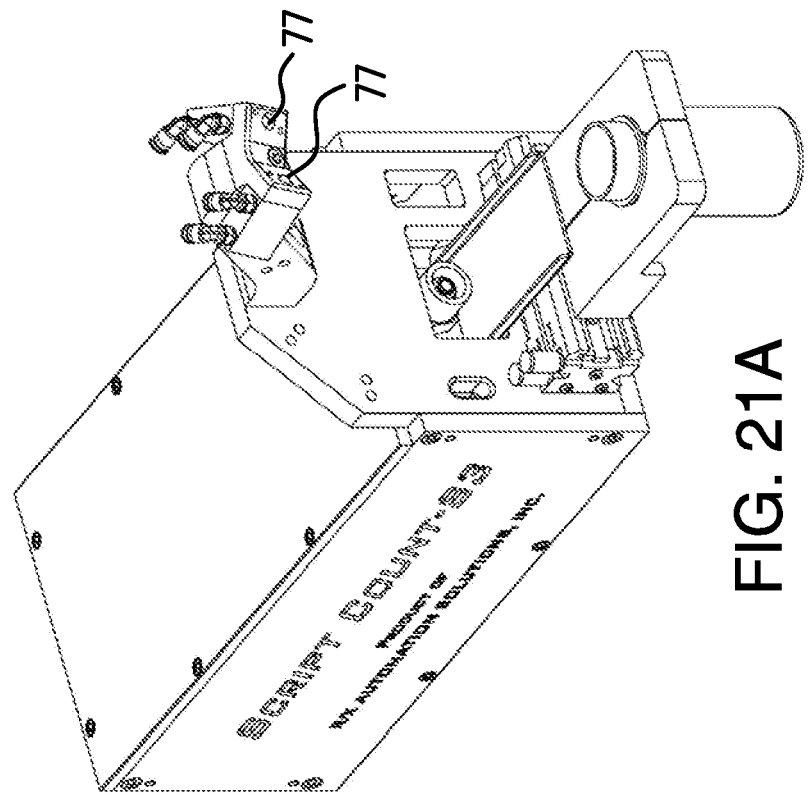
Figure 22:
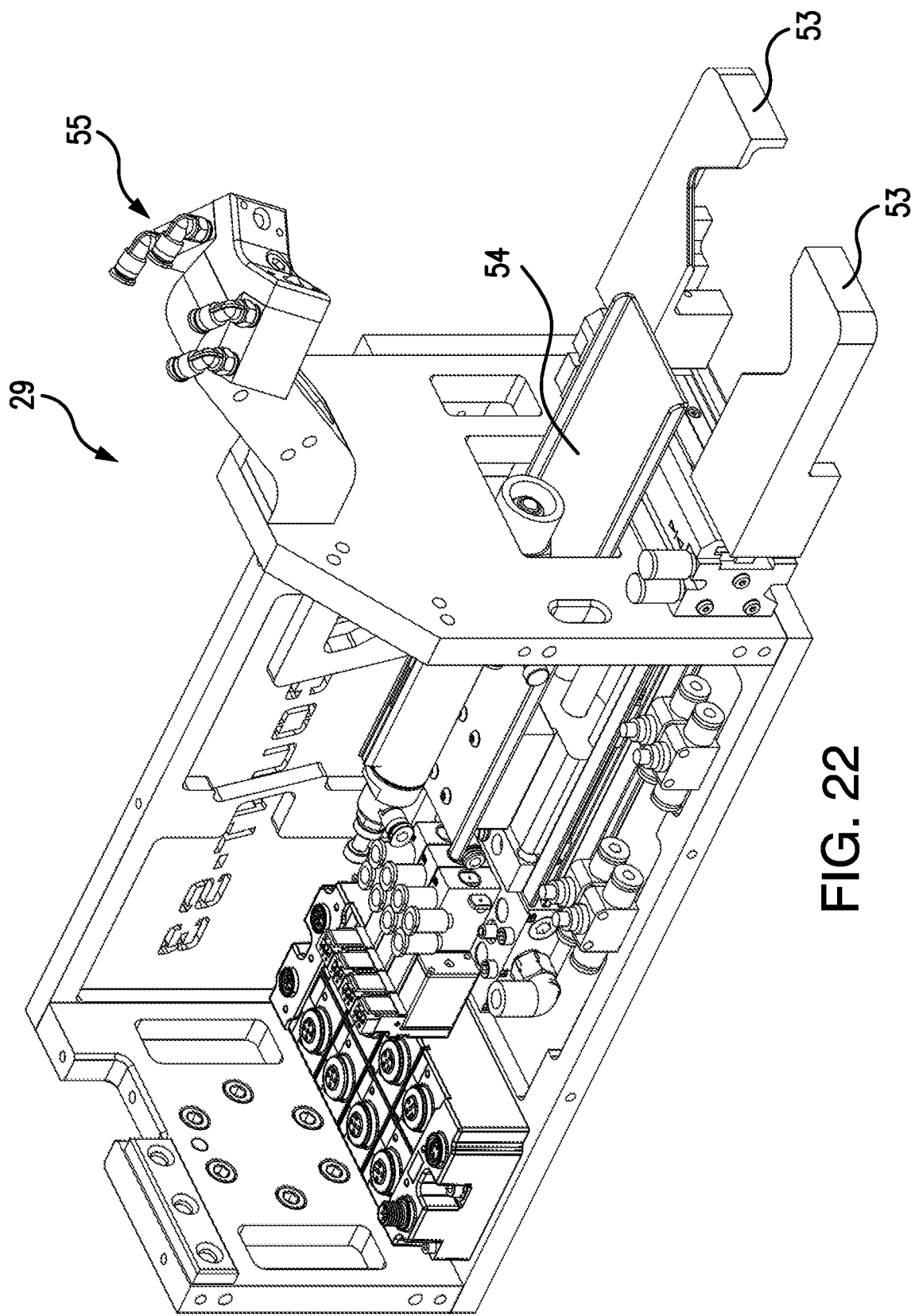
FIG. 22 shows a perspective view of the internal componentry of an end effector as may appear in certain embodiments of the inventive technology. It shows the gripper in fully open position, the bottle opening cover in deactivated (e.g., retracted) configuration, the extendable rod retracted, and a device to apply lodged pill clearance forces to a reserve container.
Figure 23:
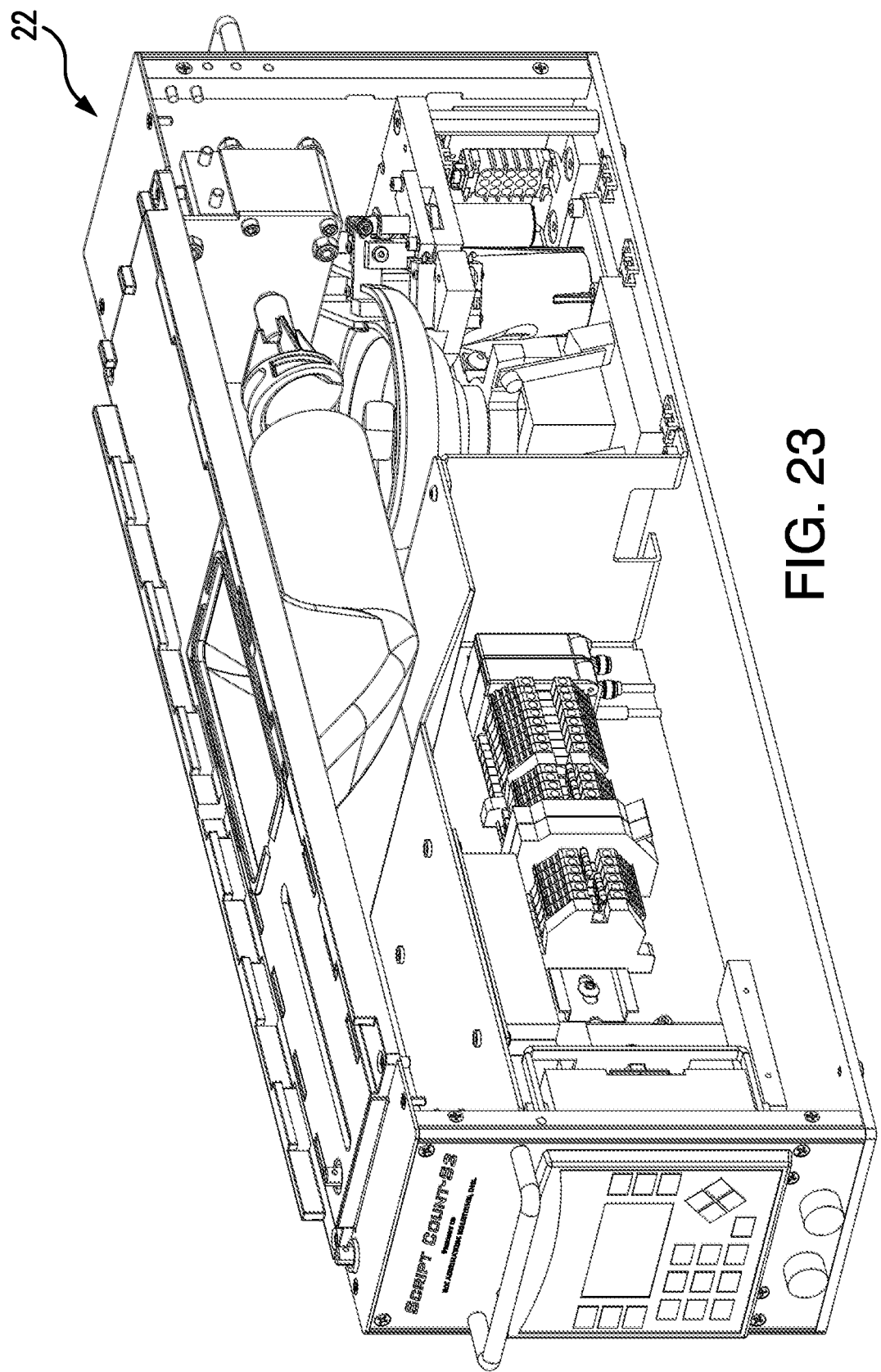
FIG. 23 shows internal components of a Script Count S3™ counter as may be used in certain embodiments of the inventive technology.

Counters 22 repositioned into sectors 57 may be said to be organized in sub-arrays 76 (i.e., a counter or counters in a particular sector), each such sub-array in a different sector (e.g., demarcated area). Just as a sector may be a set 56 or sets of counter spaces 17, a sub-array may be a set or sets of counters. A sector can even be one counter space; a sub-array can be one counter. A sub-array may include counters on different levels and at different distances from a bottle pick-up site 8. A sub-array (and its associated sector) may have an average bottle reposition cycle time that is different from that time of a different sub-array/sector. Note that even where only one counter is repositioned in response to information regarding a dispensary order cluster 21, a sub-array 76 is still said to be generated. Note that a figure such as FIG. 4 that shows reserve containers 32 extending from counters (front side) and the back side of spaces in which counters are located show counter spaces (but such spaces are occupied); FIG. 9 also shows counter spaces (it also shows them occupied by counters).

Sectors 57 can be delineated in several ways. One is simply by observing/recording the bottle reposition cycle time for each counter space 17 (the non-moving areas defined by the frame 18, that can each hold a counter 22), and then organizing (e.g., grouping) based on certain selected time ranges. Such grouping may be based on such times and time ranges (e.g., whichever spaces have times that are less than x time are sector 1, whichever spaces have times that are from and including x but less than x+0.2 seconds are sector 2, whichever spaces have times that are from and including x+0.2 seconds but less than x+0.2 seconds are sector 3, etc.). Note that time ranges need not be of equal "width", although they certainly may. Time ranges may be selected so as to create an appropriate number of sectors, e.g., at least 3, at least 5 at least 7, at least 10, at least 12, etc., and/or so that no single sector is so large that counters placed randomly therein will result in an unacceptably low increase in the order fill rate. Given that, in certain embodiments, a counter assigned a certain sector may be repositioned randomly (anywhere) in that sector, a small number of sectors (e.g., two), or even one sector that is too large in a delineation with what appears to be a sufficiently large number of sectors, will likely achieve only a portion of the processing speed gains that it might if more sectors were delineated.

Figure 25:
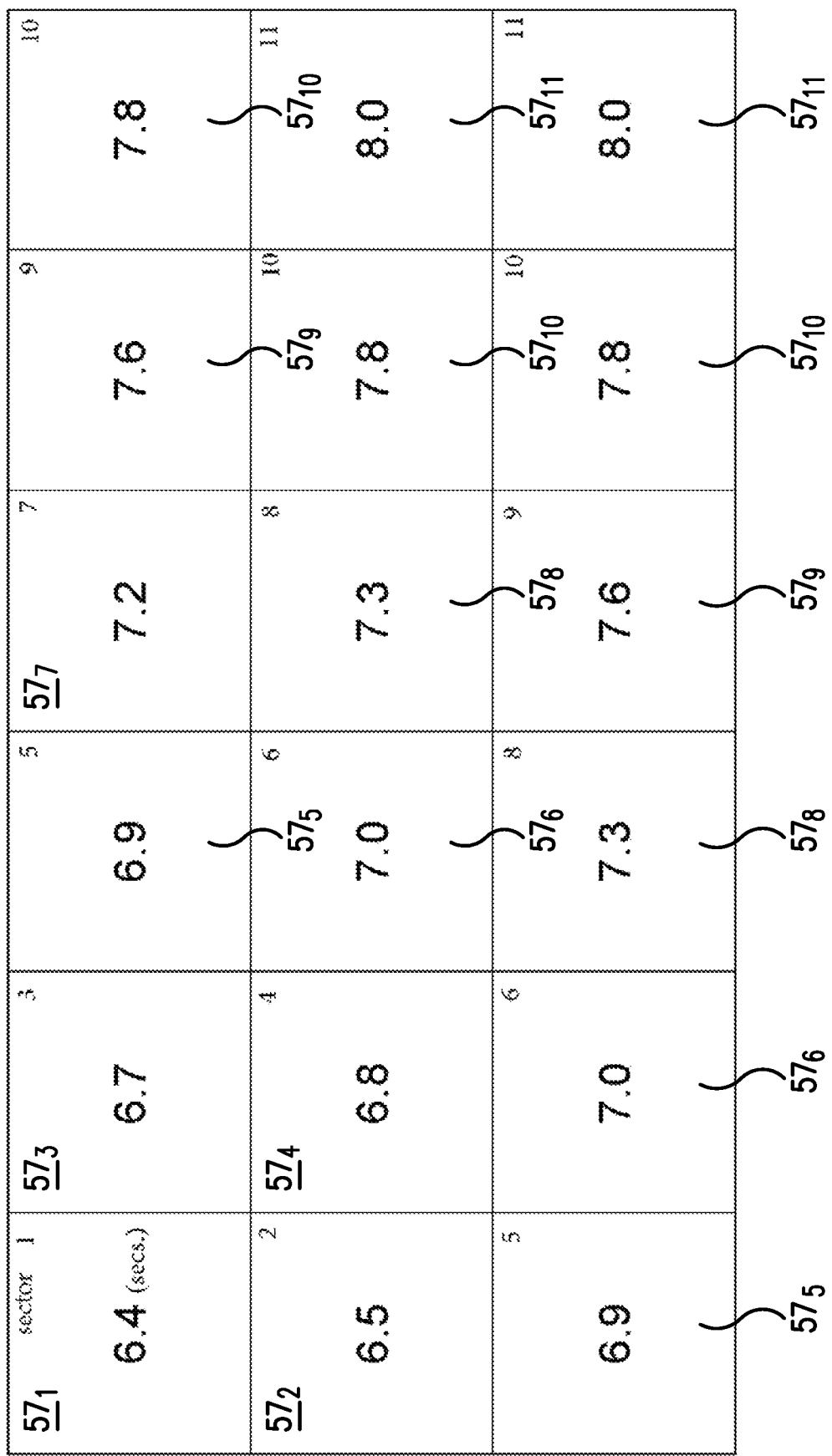
FIG. 25 shows a sector delineation (shown on a side view, from the perspective of the robot, of one half of a substantially circular robotic dispensary), and average bottle reposition cycle times (in seconds) associated with each set of 7 counter spaces (each 7 counter spaces on the same tier making up a single set), as may appear in embodiments of the inventive technology. The left side of the figure is closest to the bottle pick-up and placements sites 8, 10; as one moves right, the distance from such sites increases.
Figure 26:
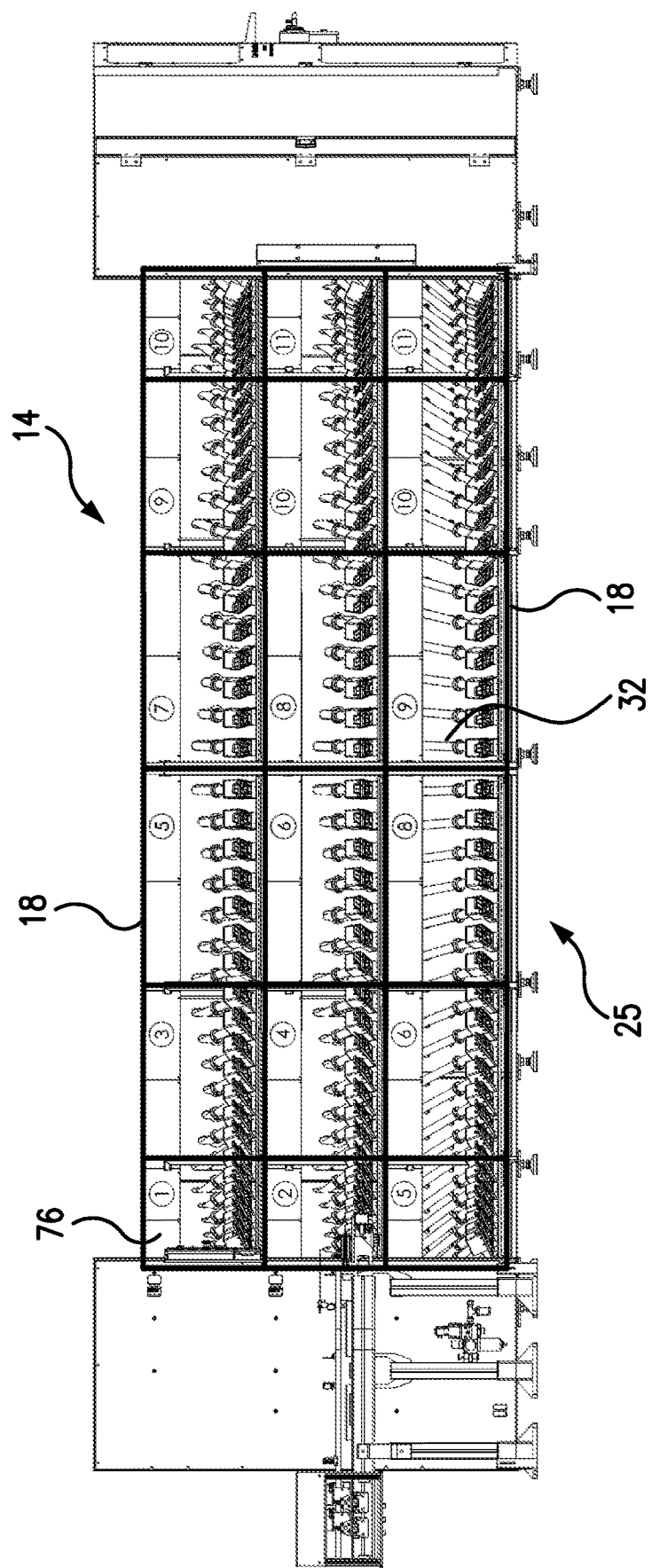
FIG. 26 shows eleven sub-arrays that are formed after counters are intentionally repositioned to the sectors delineated in FIG. 25 to achieve order fill rate gains (e.g., orders/hour), based on orders of a next dispensary order cluster, as may appear in embodiments of the inventive technology. Counters that are within "subframes" associated with the same sector (e.g., counters in the several "subframes" indicated with circled no. 10) are all of the same sub-array (accordingly, Sub-Array No. 10 has 21 (7×3) counters)). The circled numbers indicate the sub-array. Note that for clarity, only one of the 11 sub-arrays—sub-array 1—is called out, as $76_1$.
Figure 27:
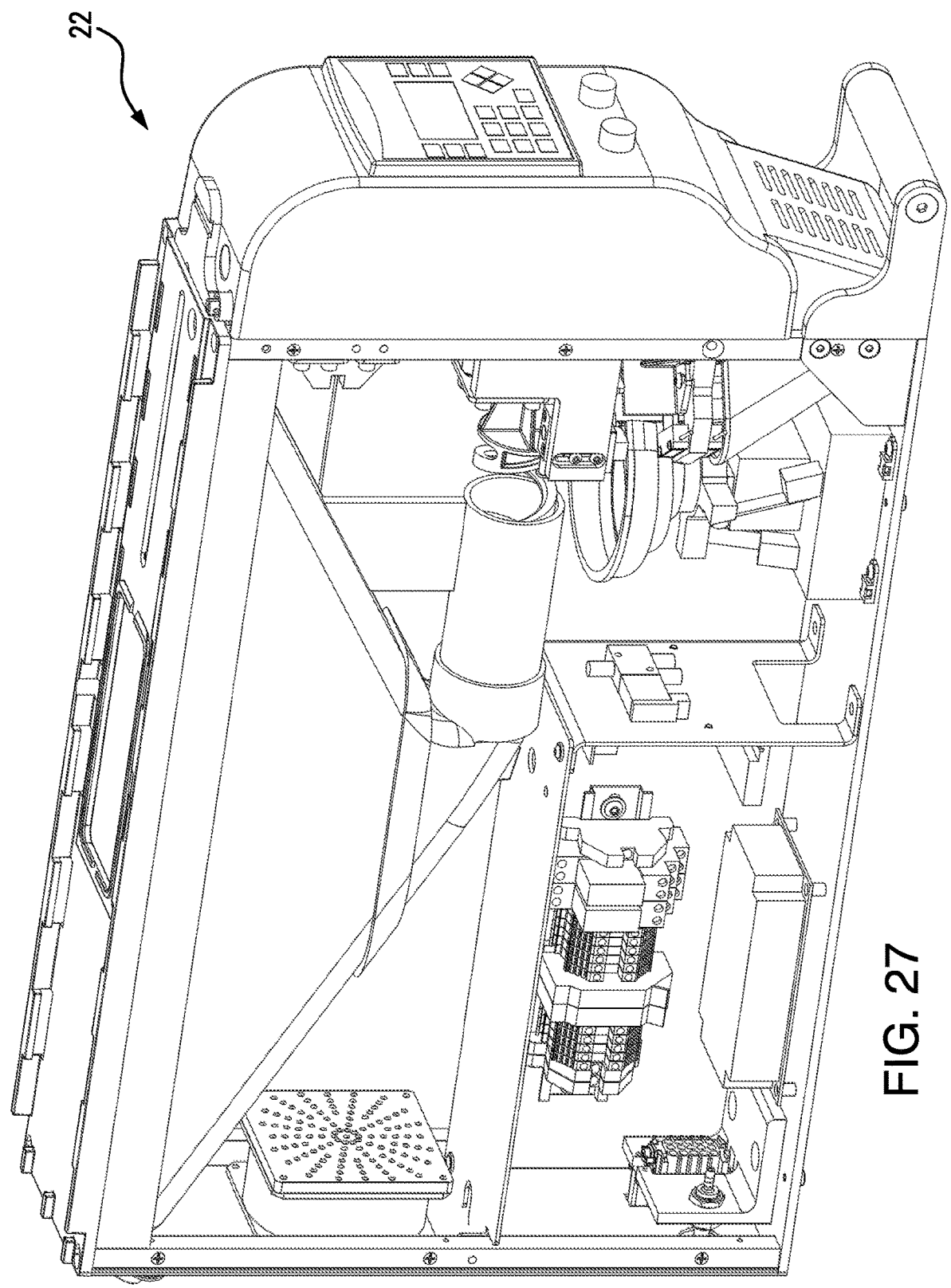
FIG. 27 shows internal components of a Script Count S4™ counter as may be used in certain embodiments of the inventive technology.
Figure 28B:
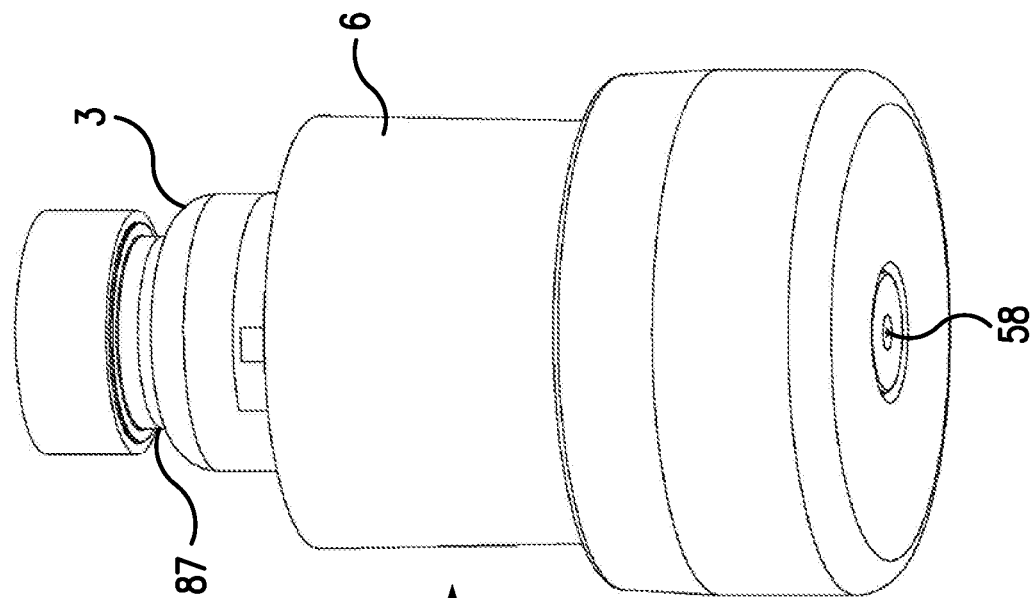
FIGS. 28A and 28B show a top and bottom perspective view, respectively, of a bottle married to a puck as may appear in certain embodiments of puck-based systems of the inventive technology.
Figure 28A:
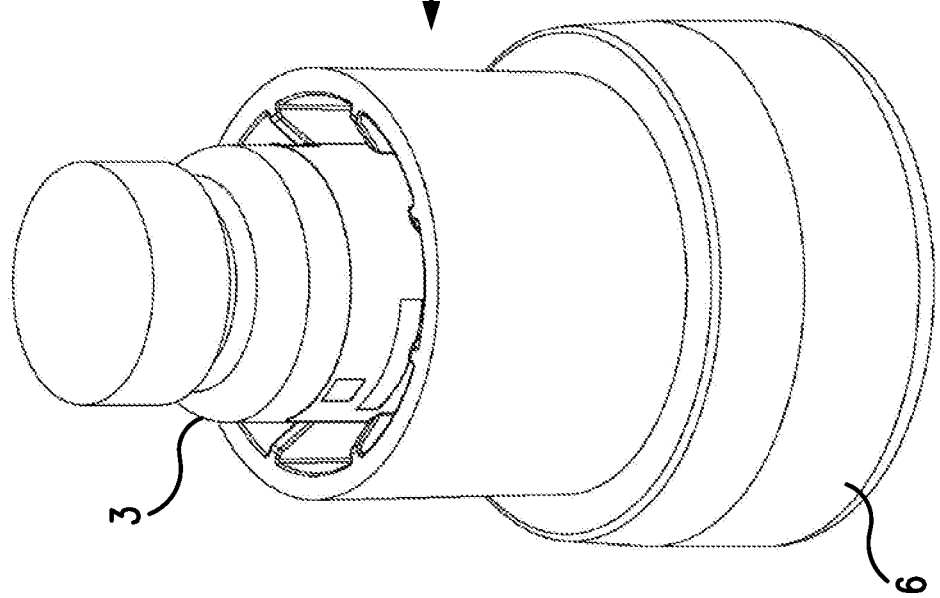
Figure 29:
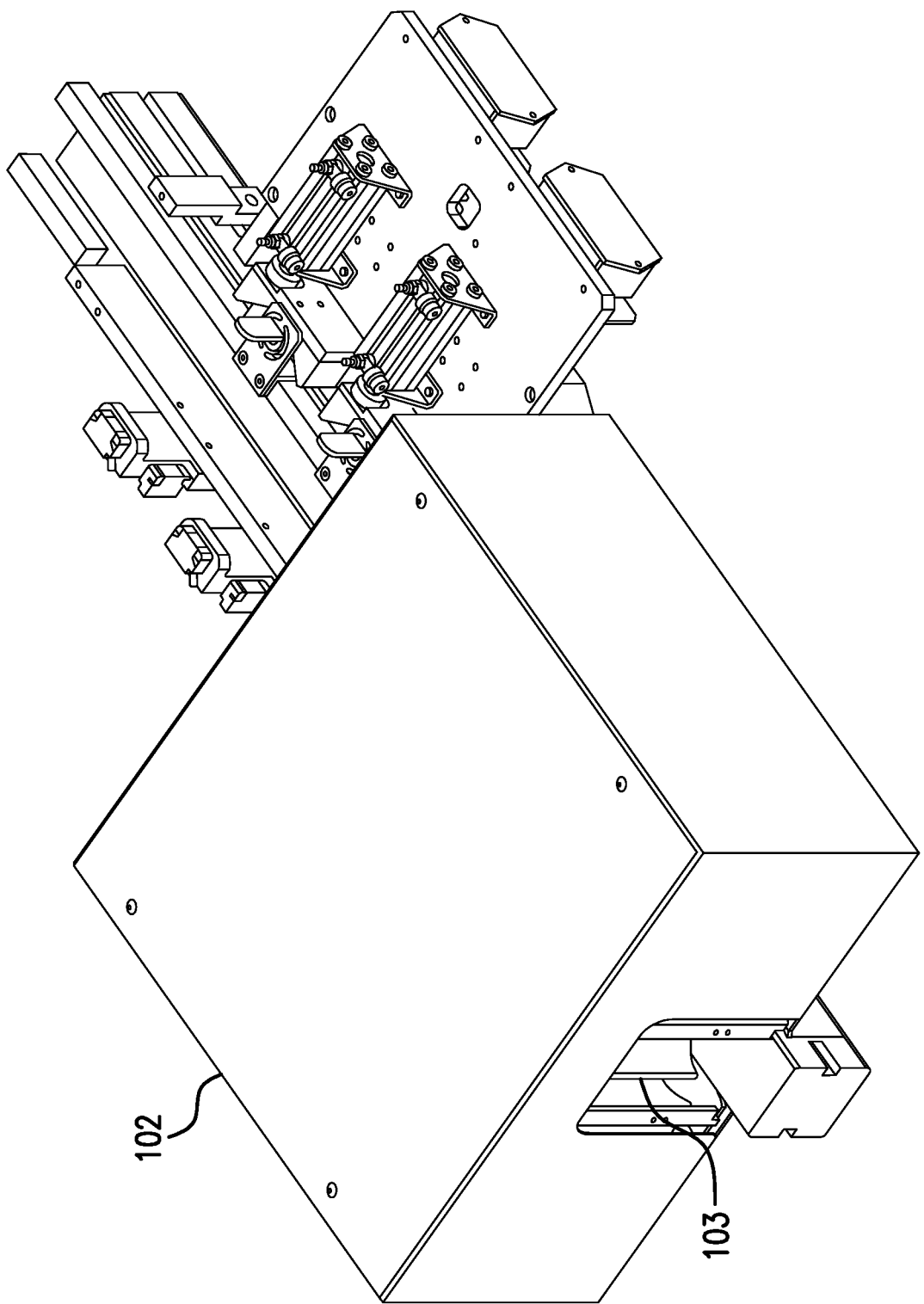
FIG. 29 shows a perspective view from an upflow side of a scanning box, and bottle pick-up and placement sites, as may appear in, e.g., certain puck-free embodiments of the inventive technology.
Figure 30:
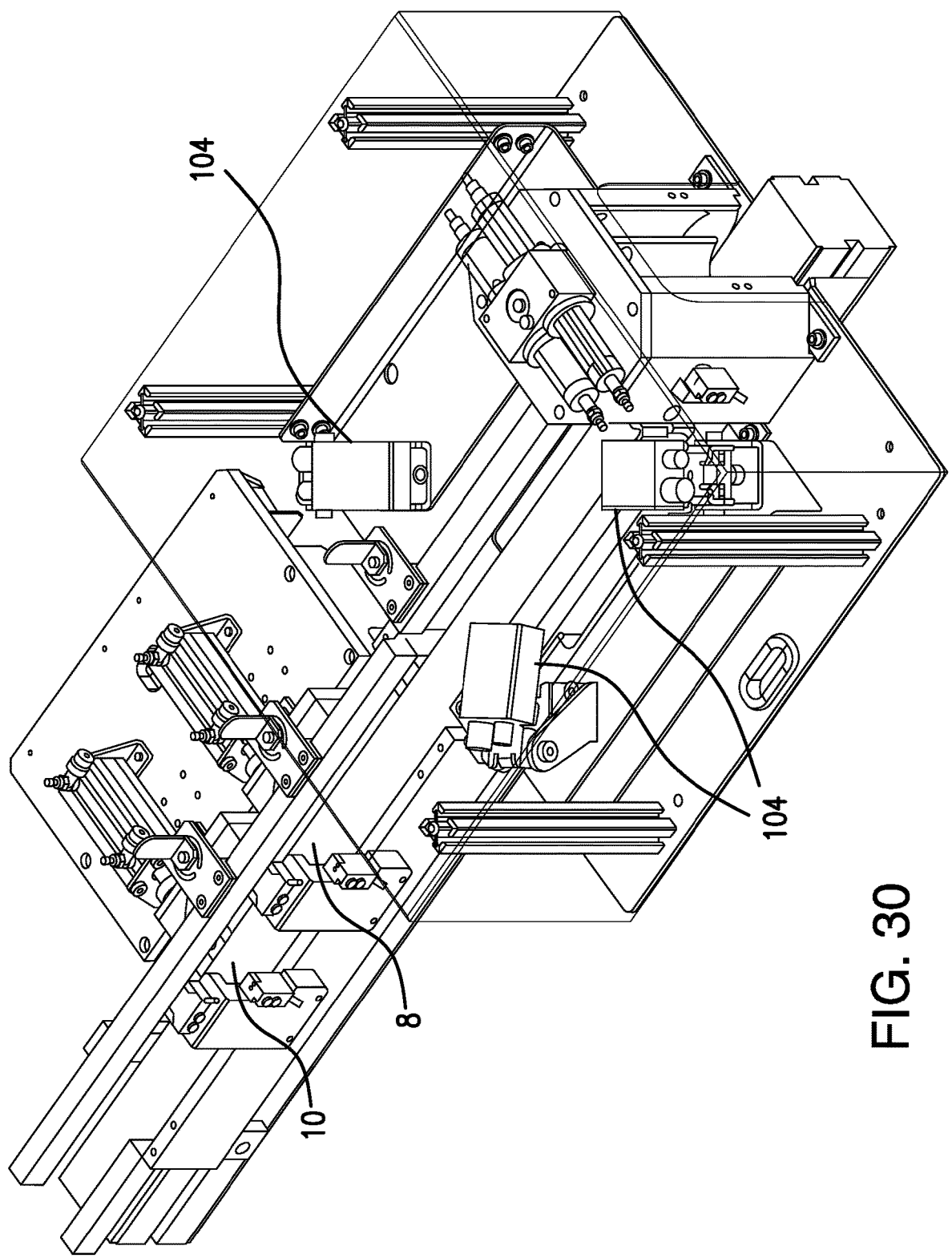
FIG. 30 shows a perspective view from an upflow side of a scanning box (shown transparently) and singulator, bottle scanners, and bottle pick-up and placement sites, as may appear in, e.g., certain puck-free embodiments of the inventive technology.
Figure 31:
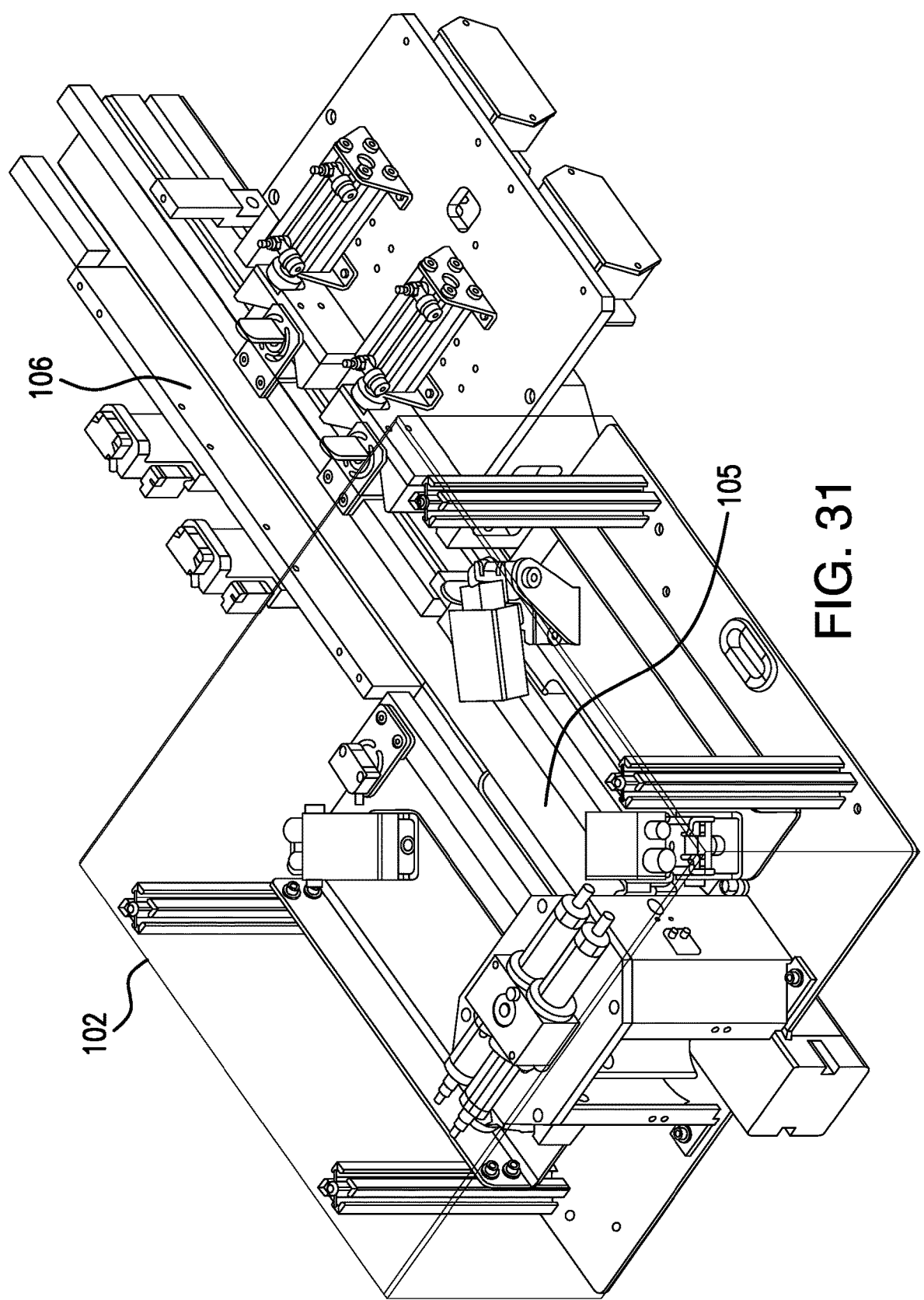
FIG. 31 shows a perspective view from an upflow side of a scanning box (shown transparently), singulator, bottle scanners, and bottle pick-up and placement sites, as may appear in, e.g., certain puck-free embodiments of the inventive technology.
Figure 32:
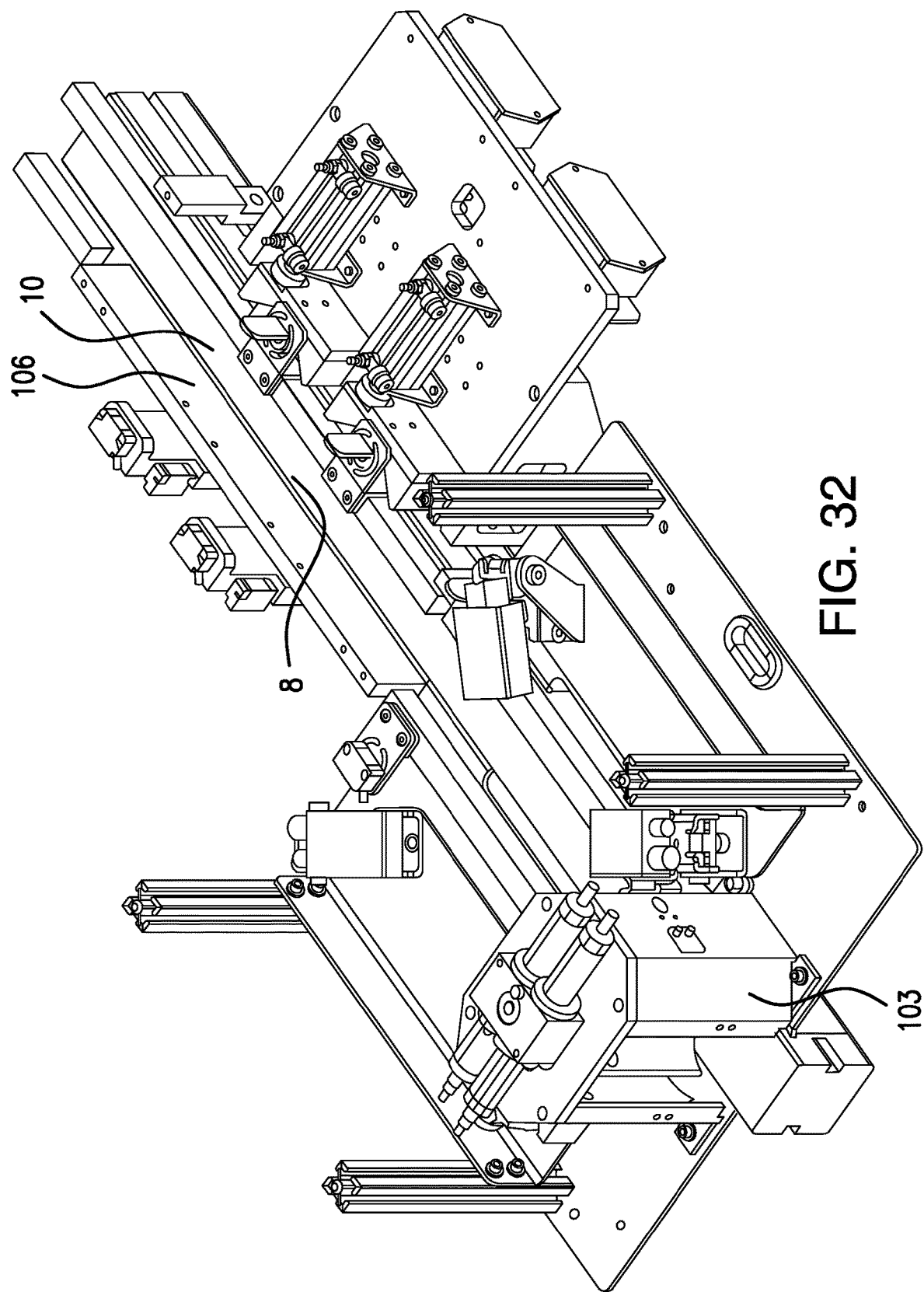
FIG. 32 shows a perspective view from an upflow side of singulator, scanners, and bottle pick-up and placement sites (box removed for clarity), as may appear in, e.g., certain puck-free embodiments of the inventive technology.
Figure 33:
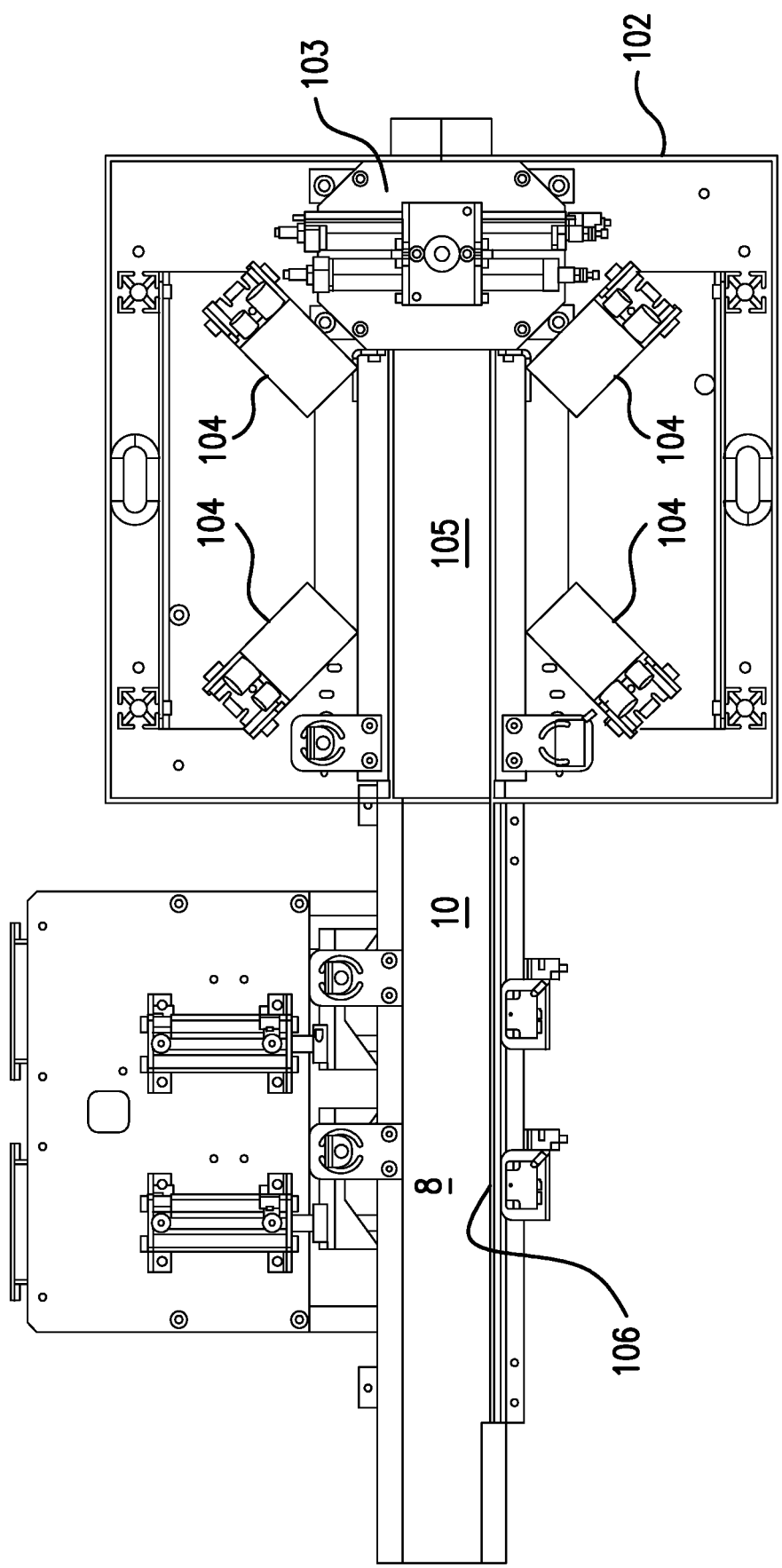
FIG. 33 shows a plan view from above of a scanning box (shown transparently), singulator, scanners and bottle pick-up and placement sites, as may appear in, e.g., certain puck-free embodiments of the inventive technology.

Another of the many ways in which sectors 57 can be delineated may include a pre-determination that each of at least the majority of the sectors is to consist of one or more of a set 56 of a certain equal number of counter spaces 17 (e.g., 7 spaces, in one embodiment), each on the same tier. Each single tier set of counter spaces will be in one sector (perhaps along with another set or sets of counters). After determining the average bottle reposition time for counter spaces in each such single tier sets of counters, they can then be organized into sectors by arranging, in ascending numerical order, all sets having a (rounded) average bottle reposition time that is, e.g., 6.4 seconds as Sector 1, 6.5 seconds as Sector 2, 6.7 seconds as Sector 3, etc., as shown in FIGS. 25 and 26 (where no such set had an average time of 6.6 seconds). Instead, such arrangement can be based on ranges of average bottle repositions cycle times (e.g., all set(s) having an average bottle reposition cycle time less than 6.5 seconds are Sector 1; all sets having an average time that is 6.5 or greater, but less than 6.8 seconds are Sector 2), etc. Ranges need not have equal width, although they certainly may; they may be selected appropriately to result in an effective number of sectors and/or where each is not so large that random placement of counters into such sector only achieves unacceptably small gains in order fill rate for a dispensary order cluster 21. Accordingly, each sector may have one or more sets of same tier counters in it (e.g., see Sector 10 of FIGS. 25 and 26). Of course, these are but a few of the many possible times (or time ranges) that could be used. Note that even when only looking at counters of a sector on one side of the bottle pick-up and placement sites 8, 10, a sector may include counters or sets thereof that are not even contiguous. See, e.g., counters of Sector 5 of FIG. 26.

Note that an average bottle reposition cycle time of counters 22 or counter spaces 17 (more particularly, with respect to the bottle fill sites 9 of counters in such spaces) can be determined in several ways: traditional averaging, using a mean (deemed an average), or using the time of a counters space that is centrally located in a particular set 56 of counter spaces. Regardless of the details of how sector delineation is achieved, the system could be configured to be programmed to accomplish it automatically, and then store sector delineation information for use in order to advise regarding counter repositioning for different/future dispensary order clusters. Perhaps the information regarding sectors 57 is already determined and stored for a customer; the system, via computer, may then provide information, given such sector delineation, regarding where counters of an upcoming dispensary order cluster should be located to achieve gains in order fill rate.

As mentioned, generally, the more sectors 57 used and/or the fewer number of counter spaces 17 in each sector, the greater the improvements in overall speed and the higher the order fill rate for that dispensary order cluster 21. In some applications, it may be that there can even only one counter space for each sector; such may help to maximize the order fill rate. It may be, however, that even though two different counter spaces have different times only when measured to, e.g., the hundredth place (e.g., 6.79 seconds vs. 6.72 seconds), such two counter spaces are deemed to be within the same sector because a choice is made to delineate a sector as including spaces with associated bottle reposition cycle times that are greater than 6.7 seconds to and including 6.8 seconds instead of delineating more than one sector in such range (e.g., 10 sectors with one being 6.70 seconds<cycle time<=6.71 seconds). Indeed, at some point the gains in time may be outweighed by the additional programming and/or labor associated with additional sectors and/or smaller sectors (e.g., manual repositioning of many counters).

It is also of note that sector delineation might not be directly related to distance of a fill site (associated with a counter 22 or counter space 17) from, e.g., a position between the bottle pick-up and placement sites 8, 10. For example, the robot 31 may be able to more quickly reach a higher tier counter space than a counter space that is two tiers below it (e.g., on a lowest tier) that is of the same (or even smaller!) lineal distance from a position between the bottle pick-up and placement sites 8, 10. This may be because of the articulation and folding (at robot arm "elbow") required by the robot components (e.g., arm, wrists, etc.) required to reach bottle fill sites 9 associated with lowest (or lower) tier counters.

The associated sub-arrays 76 would be counters 22 arranged in those sectors 57; each such sub-array could have a characteristic average bottle reposition cycle time. Note that instead of calculating the time for a bottle reposition cycle for each counter space 17, in an alternate manner of delineating sectors, it may suffice, for certain applications, to simply presume vertical demarcations among sectors (when the dispensary is viewed from the side), from highest to lowest tier, and divide the counter spaces into 2, 3, 4, 5, 6 or more sectors, each with a similar or identical number of counters, and each including a portion of all tiers of the counters. Accordingly, each sector may be shown as a ½, ⅓, ¼, ⅕, ⅙, etc., respectively, of the array's curve (when it presents with a curve) when viewed from above (a "pie slice" delineation). Other more "fine-tuned" or more highly resolved demarcations (e.g., based on recorded/observed bottle reposition cycle times for each counter space as explained above) may indeed result in greater improvements in order fulfillment speeds, but a simpler, equal "geographic," or "pie slice" apportionment may achieve sufficient speed gains for certain applications.

Regardless of the exact sector delineation process, sector delineation can be used for a single robotic dispensary 14, over a plurality of different dispensary order clusters (indeed, the bottle repositioning cycle associated with each counter space 17 might only change when, e.g., the robot base's location is changed, a new or updated robot 31 is installed, or the locations/positions of the counter spaces change due to a new frame design). The sub-arrays 76—which include the specific counters—will often change from order cluster to order cluster, particularly when the dynamic repositioning technology disclosed herein is employed.

Again, regardless of how the sectors 57 are delineated or how the profile associated with a robotic dispensary 14 manifests, after such delineation, decisions as to where counters 22 should be repositioned to achieve to improve order fill rate may be based on frequency (of, e.g., of orders for that counter's dedicated medication) and the number and size of sectors. For example, if the first sector (with the fastest/shortest average bottle reposition cycle time) has 7 counters, then the 7 counters dedicated to the 7 most frequently ordered medications of an upcoming dispensary order cluster 21 should be placed in that first sector (perhaps randomly placed therein); if the second sector has 14 counters, then the counters dedicated to the 14 second most frequently ordered medications of an upcoming dispensary order cluster should be placed in that sector (again, perhaps, but not necessarily randomly). These steps are repeated until all counters are assigned to a particular sector.

If instead there are, e.g., 4 sectors, each with an equal number of counters 22 (as may result from a purely equal geographic apportionment "pie slice" sector delineation), then the counters can be broken into the following: a first quarter that has the highest 25% of orders; a second quarter that has the second highest 25% of orders; the third quarter that has the third highest 25% number of orders; and a fourth quarter that has the lowest 25% of orders. Then, counters can be repositioned accordingly (e.g., the first quarter of counters (the counters associated with the "most popular" medications) would be placed in the first (1 of 4) sector; the second most popular quarter of counters would be placed in the second (2 of 4) sector, etc.).

A computer (e.g., via computer program such as an algorithm, etc.) may be used to inform which counters 22 should be moved and where (e.g., to which sector 57) they should be moved. Instead, such may be determined via simple determination/calculations in certain applications and/or with a plan or side view of a robotic dispensary 14 showing sector delineation. When a computer is used, it may be necessary (if not "hardwired" into the system, whether as part of a predetermined sector delineation or not) to input, e.g., how many sectors are desired, what the time ranges for each sector should be, inter alia. As mentioned, the more sectors, the greater the increase in order fill/hour speeds may be observed.

The system, aware of the position of all counters 22 for a first dispensary order cluster 21 (whether made aware via manual input, or sensed or determined electronically in some manner), and aware of the order frequency of different medications of an upcoming (such as, but not limited to, one that immediately follows) dispensary order cluster, whether made aware via manual input, or learned from particulars regarding a dispensary order cluster that are input into the system, or otherwise, may be configured to provide information as to optimal or merely better counter space 17 positioning for counters of the robotic dispensary 14 (resulting in higher bottle fill speeds). Such information can be used by a human operator to reposition counters in order to improve bottle fill speeds for that next cluster (thereby decreasing the total order fill time for that upcoming dispensary order cluster). After repositioning (which in most embodiments does not involve repositioning of any counted pill reserve containers), the counters' new positions may be, e.g., confirmed via, for example, sensing in any known manner and/or input manually into the system, thereby made available to the system so the robot 31 repositions empty bottles to the correct bottle fill site (for the order associated with that bottle, during that dispensary order cluster) based on individual orders of that cluster.

Counters 22 may be repositioned manually to achieve such dynamic repositioning; in certain embodiments, they may be easily removed from behind (e.g., outside of the dispensary) because in certain embodiments, counters are not secured or attached to either the frame 18 or to counted pill reserve containers. As mentioned, the frame for each counter's space may be configured, e.g., with physical stops, that position a counter slid into it so that, if slid far enough, will present and be oriented at the same precise position in space every time, and have a counted pill outlet 72 (port) that is directly above the inlet of a counted pill reserve container 32 (e.g., at its upper end 38) that may be associated with (even dedicated to) that counter space.

Note that formal delineation into sectors 57 may be not a required feature of the inventive dynamic counter repositioning technology. Sub-arrays 76 may exist where even a few counters are re-positioned to achieve gains in order filling speed without any formal conceptualization ahead of time relative to sub-arrays and sectors. Indeed, if at least one counter 22 is intentionally repositioned in response to information regarding the frequency of medication of orders of an upcoming cluster (whether a next cluster or otherwise) so that "more popular" (higher frequency, also known as higher volume) medications of that upcoming order cluster are dispensed by counters in counter spaces 17 having associated therewith bottle reposition cycle time(s) that are less than the times associated with the counter space in which such counters were located before repositioning, then such system falls within the ambit of the inventive technology disclosed herein.

Note that, while preferred embodiments of the inventive technology feature counters 22 that are each dedicated to a particular medication, even those robotic dispensaries 14 that, in whichever way, do not feature such dedication, may benefit from dynamic repositioning embodiments of the inventive technology. Simply, counters would be left in place and the hoppers 23 associated with (typically dedicated to) each of the counters 23 (and that contain a particular medication), would be moved to counters located in spaces that, as based on ordered medication frequency of a next dispensary order cluster 21, would improve order fill rate for that cluster.

As indicated, an array frame 18 may include framing for each counter space 17 that assures that a counter 22 placed therein will present in a precise position (e.g., so the counter can be readily positioned with respect to a waiting counted pill reserve container 32 so pills dispensed from the counter's dispensing outlet 72 always discharge into an upper end 38 of the reserve container). There may be no, or minimal connection of a counted pill reserve container 32 to a counter (e.g., at the counted pill outlet port 72 of the counter). Note that the system may also be configured (e.g., the reserve containers 32 may be attached to a counter array frame) so a counted pill outlet of the reserve container 32 (e.g., substantially their lower ends 39 (such as where door componentry 41 is established)) always is at the same location, even after a counter associated with a particular reserve container 32 for one dispensary order cluster 21 is moved to another location in the array for a subsequent cluster. In this way, when the robot 31 needs to reposition an end effector 29 to a bottle site for a particular counter located in a certain spot in the array, the robot can always (over several or even all dispensary order clusters) reposition its end effector 29 to the same bottle order fill site for that particular counter spot. Of course, this simplifies the robot repositioning process and programming, and increases the system's functional reliability and operational confidence.

Particular embodiments of the inventive technology may relate to the avoidance and/or disruption of any lodging of pills that may prevent the dispensing of all counted pills in the reserve container 32 in a single dispensing event (i.e., in one "pill-slide"). For example, instead of 20 pills dispensed in a single pill slide, 18 are dispensed in that slide. Whether pill bridging, stuck pills (e.g., gel cap(s) that is stuck to an internal side of the reserve container), or other lodged pill situation, one, some or even all of the counted pills that are held in a reserve container 32 may at times remain in that container even after the door 52 at the lower portion thereof is opened and sufficient time has elapsed for pills to normally (i.e., during a single pill dispensing event) empty from the reserve container. Normally, and ideally (i.e., when no pills are lodged), when the door is opened, gravity should cause all pills to slide out of the container during a single pill dispensing event into an awaiting pill bottle. Of course, unintentional pill retention can, inter alia, result in insufficient order fulfillment, where bottles are filled with fewer pills than are required by the order associated with a particular bottle; it may also cause fulfillment problems for subsequent orders.

Embodiments of the inventive technology may solve this problem by providing componentry in the form of a device 55 that applies forces—lodged pill clearance forces 33—that are sufficient to dislodge unintentionally retained pills. When such clearance forces are initiated by a device (as opposed to initiated manually by a person), they are referred to as regulated, meaning they are controlled so that they are not so large as to disrupt the proper operation of the counted pill reserve container 32 (e.g., by causing its detachment at its upper 38 or lower end 39, by causing problematic door operation, by causing pills that, when dispensed, do not fall into an awaiting bottle, by breaking pills, etc.) During backup "manual bottle reposition cycle operation," clearance forces may be initiated by an human; such human applied clearance forces are not considered regulated.

Note that the system may be configured such that lodged pill clearance forces 33 include cyclically applied forces—the first force of a cycle may be a regulated force applied by a device in a certain direction, and any subsequent force(s) may be applied by a device in any direction. A cycle may be viewed as the set of forces that are repeated (each set being a cycle); a plurality of cycles may be used for each dispensing event (e.g., for each "pill-slide"). The end of each cycle may, but certainly need not, leave the reserve container 32 in its pre-clearance force application configuration. However, after the last of all lodged pill clearance forces associated with the final lodged pill clearance force cycle for a particular dispensing event is completed, the reserve container 32 would typically be left in its pre-clearance force application configuration (position and shape). Note that such "return" may be effected by a device applied clearance force, and/or by more of an elastic restoration force (in response to a clearance force), whether applied by elastic attachment componentry and/or or a reserve container 32 made up of elastic material (discussed more below).

For each dispensing event (e.g., for each "pill-slide"), such lodge pill clearance force cycle may be repeated any number of times (at least that number of times that is deemed sufficient to clear all foreseeable lodged pill situations), preferably without causing any delay during bottle reposition cycles. In one embodiment capable of such repeated, cyclically applied lodged pill clearance forces 33, such may be applied, at least in part, via one or more small hammers 13 that repeatedly impact (e.g., tap) a reserve container. This may be done directly on the container or by tapping a part (e.g., a rigid collar 34 around a reserve container) that the reserve container 32 will move with when that part is displaced, so as shake/vibrate/agitate the reserve container 32 and dislodge any lodged pills. Lodged pill clearance forces may be applied before, or ideally all during, a pill dispensing event.

Lodged pill clearance force cycles may be initiated from outside of the reserve container 32 (i.e., they may be externally applied); may be applied for every bottle reposition cycle (i.e., for every bottle fill/pill dispensing event, when an empty bottle is at its associated bottle fill site; and/or may be applied so that they do not add to the time elapsed during a bottle reposition cycle (e.g., a sufficient number of cycles to clear any lodged pills is completed (i.e., a sufficient number of lodged pill clearance forces are applied) earlier than the longest expected time for all pills of an order to dispense in a single pill dispensing event, i.e., before a bottle is removed from its bottle fill site).

Particular embodiments may feature an intentional design whereby the counted pill reserve containers 32 are attached at their upper portion and/or their lower portion in a way that allows movement of the entire reserve container 32 relative to that stationary componentry 78 (e.g., the counters 22 and/or a frame 18 (for counter or counter array) in response to an applied pill dislodging force(s). Note that a counter is considered stationary during a single dispensary order cluster 21 even though it may be moved (from one counter space 17 to another) between clusters. Embodiments may feature attachment componentry 35 that attaches the reserve container to stationary componentry; such attachment componentry may be relative movement affording attachment 79 that intentionally allows movement of the reserve container 32 relative to stationary componentry 78 to which it is connected, directly or otherwise, in response to application of a clearance force(s) 33. Such embodiments may provide a "floating" counted pill reserve container 32 design. Such relative movement affording attachment 79 may: assure the applied dislodging (lodged pill clearing) force(s) is effective in relatively moving the reserve container 32 sufficiently (perhaps on the order of millimeters, or even less) to dislodge any lodged pills even though the reserve container 32 is attached at one or both ends to stationary componentry 78 (e.g., the counter array frame 18); and/or allow the use of force that each is less (in magnitude), together are fewer in number, and/or together are shorter (in duration), than they would need to be (in order to dislodge any "stuck" pills) as compared to the case where no relative movement affording attachment were used. "Relative movement affording" here simply implies the allowance of relative motion (in response to a lodged pill clearance force 33) of a part(s)/component(s) (with respect to stationary componentry 78 to which it is attached), in at least in one of: a direction that is perpendicular to any longitudinal axis 67 of the reserve container, and a direction that is aligned with such axis (such would be seen not only with forces aligned with such directions, but also with forces having a component(s) aligned with such direction(s)). Certain embodiments may provide a mounting plate (used at either or both of the ends of a reserve container) that, with some adjustability, allows for relative motion of a reserve container 32 in a direction that is aligned with (including parallel to or collinear with) a reserve container longitudinal axis 67.

As mentioned, the intentionally relative movement affording attachment 79 may include an elastic component 36 such as one or more o-ring(s) 37. Such elastic component 36 may accomplish one or more of the following: provision of an relative movement affording attachment that, while affording relative motion with respect to stationary componentry 78 to which an item (e.g., a reserve container) is connected, is still a secure attachment (a snug connection, e.g., not susceptible to unwanted disassembly upon long-term application of clearance forces 33); and return of the container, at least to an extent, to its undisplaced configuration (i.e., to its original position in space, or shape) upon disapplication of an applied lodged pill clearance force (for a single dispensing event). Of course, enough time must be allowed before the application of any subsequent device-applied force in a different direction for such restoration force to return the container to its pre-force configuration (at times, the restoration force, if allowed, will return a container to its pre-force configuration very quickly, e.g., milliseconds). Where such elastic restoration force induced motion is observed, the relative movement affording attachment 79 is considered as allowing such motion also.

Note that instead of or in addition to an elastic component 36 as part of the attachment component, the material used for the reserve container 32 may be selected so that one or more portions of a reserve container 32 can be displaced in response to a lodged pill clearance force(s) 33 so as to deform the container; after such deformation, at least in part because of elastic materials used for the container, the deformed container may elastically return to its pre-deformation position and shape (if indeed enough time elapses before the application of any subsequent clearance force). Such material need not be rubber or elastomeric (indeed they may, however), as certain clear vinyl, PVC tubing may suffice. For example, any material that, when used for a tube, and when one end is displaced with respect to the other end, reliably returns to its original position/shape, may suffice. Note that such design may find particular application in those embodiments where the lower end of the reserve container 32 is not attached to something that is stationary (e.g., such as where the lower end of the reserve container, and perhaps door componentry 41 established at such lower end, is unattached on all sides). Note that door componentry includes the door 52, and at least some of the componentry that operates it (via opening and closing it).

It is of note that device applied forces may be timed such that between one such force and the next (any of a cycle or plurality of cycles of device applied forces), an elastic force (whether effected by elastic attachment componentry and/or elastic materials that make up the reserve container 32 itself) can cause a restorative process whereby the reconfigured container (in shape and/or position) returns, at least partially, to its pre-device applied force configuration (in shape and/or position). However, this is not a required feature, and there may be so little time after each applied lodged pill clearance force 33 and/or chosen elastic materials may be so slow reacting, that there is no substantial restoration in position and/or shape before the next clearance force 33 associated with a dispensing event is applied (indeed, it may be successive lodged pill clearance force that returns the container to its earlier configuration). But where the last clearance force applied for a pill dispensing event leaves a reserve container 32 out of its undisturbed configuration (shape and/or position), elastic restoration, whether effected by elastic attachment componentry (such as o-rings 37 at the upper 38 and lower ends 39 of the reserve containers, and/or an elastic reserve container), may act to return it to its undisturbed configuration.

In particular embodiments, lodged pill clearance forces 33 may be applied by a device 55 that is moved by the robot. Such device may be established substantially at the end of the robot arm 28 (e.g., at and as part of the end effector). It may apply clearance forces cyclically where, e.g., each cycle uses one, or two or more hammers 13 to impact the container so that it is quickly moved, relative to stationary componentry 78, in at least two different directions. In particular embodiments, a first-acting hammer may first (percussively) tap a collar 34 around the reserve container 32 in a first direction, and a second-acting hammer may shortly thereafter (percussively) tap that collar in a second direction. It is not required that such impact be on a collar around the reserve container 32 instead of on the reserve container, although such may be preferred in certain embodiments. Each hammer may be cylinder based, and may have two air input elbows 90 that intake air for pressurization to drive a hammer motion. Each hammer may have an extended mode and a retracted mode.

Such hammers 13 may impact both sides of the collar 34 (or reserve container), e.g., one on one side and one on another, or two on one side and two on another, whether there be two hammers or more. Of course any arrangement of, e.g., hammers, direction of force at time of impact, and any time intervals between taps could be used. Further, a single hammer may tap once or more than once before the next hammer taps, and any number of taps could be used in a single cycle (where the device applies forces cyclically). Where forces are applied cyclically, each cycle may be repeated any number of times, but preferably at least that number of cycles sufficient to clear any lodged pills will have occurred before the expected completion time of a single dispensing event (e.g., a single "pill slide"). Note that hammers may, in certain embodiments, during impact, protrude through an interface that may be positioned, by the robot, against the collar 34 (or the reserve container 32 in those embodiments where impact is directly with the reserve container).

As discussed further below, robot wait time (during a dispensing event) may depend on, e.g., bottle size or number of pills to be dispensed, as may the duration of the application of lodged pill clearance forces 33. However, even where robot wait time is adjusted depending on bottle size (or number of pills), it may be that the duration of application of lodged pill clearance forces for a single bottle is equal for all bottles, regardless of bottle size (in such case, it would be completed before the end of the shortest dispensing event). And of course, where the same robot wait time is used for all bottle sizes/number of counted pills, the duration of application of lodged pill clearance forces can be the same for all orders.

Agitation of the reserve container 32 to clear any lodged pills may occur during the dispensing process. In certain embodiments, a device may apply 10-30 force cycles for each dispensing event (this is just one of many examples, however). Any method—sensor, robot position information/feedback triggering, automatic occurrence after a prior (e.g., immediately preceding) event (e.g., after reserve container door 52 opening), and/or microprocessor control, etc.—so the device applies forces at the correct time/within a proper time window can be used. Note that in certain embodiments, at least part of the clearance force application may occur before a dispensing event, although certain embodiments involve the application of all such forces during that event.

In dispensing pills during a dispensary order cluster 21, two general approaches can be used with respect to how much time the robot 31 holds the end effector 29 stationary during a pill dispensing event (e.g., during a single "pill-slide"): (1) the same waiting time is used for all bottles; or (2) one of a plurality of waiting times is used for each bottle. As to the second option, perhaps there is a different waiting time for each bottle size (in most clusters, orders are filled using bottles of different sizes; in each dispensary order cluster two or more different bottle sizes may be used (e.g., two or more of 60 cc, 100 cc, 150 cc, 200 cc, as but a few examples)). Alternatively, perhaps a robot wait time is based instead on the number of pills to be dispensed. Regardless, Option (2) indicated above may increase order fill rates (e.g., # bottles filled per hour) by avoiding the excessive robotic wait time associated with Option 1 for certain bottle fills (indeed, under Option (1), a robot wait time that is long enough for even the biggest orders (e.g., largest number of pills) would need to be used for even the smallest orders (e.g., fewest number of pills) resulting in perhaps significant wasted time. Accordingly, whether based on the bottle size (perhaps, e.g., sensed by the robot's end effector) or based on the number of pills in an order, each bottle may have associated with it an estimated maximum bottle fill time, the longest time that a bottle of a certain size would take to be filled (to its capacity), or the longest time a certain number of pills would take to be dispensed. Of course, larger bottles and orders for a greater number of pills have a longer such estimated fill time. The maximum time may be relevant because, e.g., within any given bottle size there may still be different numbers of pills, resulting in a slightly different actual time to dispense. Accordingly, the fill time used is the longest (i.e., a maximum) that would be required for that bottle size or that number of pills, for the most time consuming pill dispensing event (e.g., a bottle of a certain size that is filled to allowable capacity with pills) to complete. Note that where the estimated maximum fill time for a bottle is based on number of pills (required by the order associated with a particular bottle), pill numbers may be grouped in any manner (e.g., 1-30 pills has a first estimated maximum fill time; 31-50 pills has a second estimated maximum fill time; 51-80 has a third estimated maximum fill time, etc., as but one example). Where based on bottle size, each bottle size may have an estimated maximum fill time.

The LVD robot may be configured to coordinate an individual bottle fill wait time (i.e., the time the robot remains stationary while waiting for the bottle to fill, during a pill dispensing event) with the estimated maximum fill time for the order associated with it such that the robot waits, in stationary position, substantially only as long as the estimated maximum fill time, and no longer. This reduces a total bottle fill wait time (i.e., the total time the robot is spent waiting for all bottles of a dispensary order cluster 21 to fill) as compared to what it would be without such coordination (e.g., where only one fill time is used for all orders as indicated in Option (1) above). While each such coordination may amount to only less than 1 second, one second, slightly more than one second or only a few seconds in time savings for a single order (a single bottle fill), such time savings does indeed add up and could amount to several minutes in savings over an entire dispensary order cluster. It is of note that where, in whatever manner, the time the robot waits during a dispensing event to fill a bottle is selectively adjusted to be one of a plurality of different times, with the effect of increasing the rate at which orders are fulfilled, then the system is said to be configured to coordinate an individual bottle fill wait time with an estimated maximum fill time.

Size of a particular bottle is often already "known" by the system before its end effector 29 picks up that bottle; such information, in addition to other information associated with the bottle and its order, is accessible by the robot, and can be verified by the robot 31 (e.g., using sensor(s)). Indeed, in certain embodiments, the bottle's end effector 29 (e.g., which includes a gripper 53) may be able to sense the size of the bottle when it is grasping it (e.g., via known methods to sense a characteristic such as bottle width (at neck 87 or other part of bottle) sensing or weight sensing through use of a sensor that forms part of the end effector). Such may act as a check (a redundancy measure) to assure that a bottle in a certain location (e.g., bottle pick-up site 8) is of the same size as the size of a bottle that should be in that location. Such sensing, which may occur at the bottle pick-up site 8 immediately after pick-up, or at other time during grasping of the bottle by the end effector, may be considered a redundant check of sorts because there may have already been efforts to place a bottle of a certain size in that position in the queue 46 (and, in puck based systems, in a puck that is specifically sized for that bottle). If the bottle is sensed to be of a different size (as compared to the size that it should be), e.g., a bottle of size X is sensed where a bottle of size Y was expected to be, which may be observed in the event of a bottle queuing error, for example, then some sort of action—signaling to operator, automatic conveyance to an exception station 74, and/or temporary shutdown, as but a few examples—may be automatically taken.

As mentioned, a conveyor may transport a bottle (and a puck in puck-based systems, forming a puck and bottle combination 49 where the two are "married" to each other, at least for a time) to a bottle pick-up site 8, where a first bottle obstructer 44 may stop the bottle's conveyor-caused motion and may also position the bottle (or perhaps the puck in puck based systems) so that the bottle is positioned precisely at a specific, predetermined location at least in a two dimensional, horizontal plane. That location in that plane may be referred to as a first point 83, and identified by values in horizontal x and y axes, which are aligned with the direction of the conveyor and perpendicular to it, respectively. Such (horizontal) x axis 81 aligns with the movement direction of the conveyor at the bottle pick-up site 8 (e.g., an axis that is parallel with two side edges of the conveyor and/or aligns with one edge 85 of the conveyor); such (horizontal) y axis 82 is perpendicular to that direction (e.g., it is perpendicular to two side edges of the conveyor). That first point 83 may be defined by the intersection of lines defined by values in horizontal x and y planes); the line in the y plane may, but need not, be halfway between the two edges of the conveyor. The robot 31 can then repeatedly position the end effector 29 using the same robotic positioning motion (at least with respect to horizontal x and y axes) for every bottle so each can be reliably and confidently picked up (e.g., grasped) at the pick-up site 8 (the first point 83 defines center on which that pick-up site is generally located, perhaps also in addition to a height at which the bottle is grasped). Such proper positioning facilitates system operation, and eliminates the need for real-time sensing or other "customized" end effector 29 positioning that would be necessary in the event the bottle, when ready for pick-up, could be located at more than one point in a horizontal plane.

The bottle can be positioned by the first bottle obstructer in such manner when its center (and the center of the puck that supports it in puck-based systems) is positioned so its center aligns with a specific, first point 83 in a horizontal plane (i.e., at a certain point defined by values of the aforementioned x and y axes). Similarly, a second bottle obstructer 45 may shortly thereafter position the same bottle at a certain (different) second point 84 in a horizontal plane so that the robot 31 may, by repeatedly positioning the end effector 29 using the same robotic positioning motion (at least with respect to horizontal x and y axes) for every bottle, reliably and confidently place that bottle at the placement site 10 (and into the properly positioned, waiting puck in certain puck-based system embodiments). Note that the second point 84, perhaps in addition to a height at which the gripper 53 releases the bottle (again, into a puck in puck-based systems), defines that placement site, in manner analogous to how the first point 83 defines the pick-up site 8). In this manner, the bottle obstructers may provide an advantageously simpler design, by reducing the need for the robot's motion, for every bottle reposition cycle, to be customized, with respect to a horizontal plane, for that particular bottle/order.

Both puck-based and puck-free systems may include a first bottle obstructer that blocks a moving, empty bottle on said conveyor, preventing its further conveyance along said conveyor, and that positions said bottle so that its center aligns with a first point so that said empty bottle is properly positioned, at said bottle pick-up site, for pick-up by said end effector; and a second bottle obstructer established downflow of said first bottle obstructer.

In puck-based systems, a first bottle obstructer may block a moving puck on the conveyor, preventing its further conveyance along the conveyor. It may position the puck so that its center aligns with a first point so that an empty bottle supported by the puck is properly positioned, at the bottle pick-up site, for pick-up from the puck by the end effector. A second bottle obstructer may block a moving puck on a conveyor, preventing its further conveyance along the conveyor. It may position the puck so that its center aligns with a second point so that the puck is properly positioned, at the bottle placement site, for placement of a filled bottle into the puck by the end effector. In puck-free systems, a first bottle obstructer may block a moving bottle on the conveyor, preventing its further conveyance along said conveyor. It may position the bottle so that its center aligns with a first point so that the bottle is properly positioned, at the bottle pick-up site, for pick-up by said end effector. A second bottle obstructer may form a hard stop against which a bottle may be placed, so that, when placed at said hard stop, a bottle center aligns with a second point. Note that even though, in both puck-free and puck-based systems, the second bottle obstructer may appear to only briefly obstruct movement of a bottle (indeed, in puck-based systems, it appears to obstruct puck motion for a longer period of time), it is still termed a bottle obstructer.

Puck free systems may include a singulator that is located upflow of the bottle pickup site (and the first bottle obstructer). The singulator may accomplish initial steps in the following exemplary sequence:
1. Bottle's presence is sensed at the singulator (as used here, it is a mechanism that effectively inserts a space gap in between a first and a second bottle in a queue so that such first bottle can be accurately scanned (without interference posed by a bottle that is too close to it) by a scanner array (e.g. a quad scan);
2. Bottle is released to scanners by singulator 103;
3. A scan of the bottle is completed by the scanners 104 (e.g., bar code scanner, or other reader) at a bottle scan location 105 in a scan box 102 as it travels to the first bottle obstructer (at the bottle pick-up site). If scanning is unsuccessful (e.g., no scan), or wrong/bad barcode the robot will never pick the bottle and it will index through the bottle pick-up and placement sites;
4. At the bottle pick-up site, the bottle size can be obtained by sensors or upon read of the barcode;
5. The first obstructer grips bottle for pick-up by the robot;
6. Robot picks up and fills the bottle;
7. Next bottle advances to the pick-up site (like pucks do);
8. Robot finishes fill and places bottle at the placement site when pin second bottle obstructer are extended (note that in certain embodiments, only the pin is extended before and during bottle placement; the wedge(s) may be extended after bottle placement but before release by the robot to better stabilize/secure the bottle and assure a clean release);
9. Robot releases bottle;
10. Pin and wedge(s) of second bottle obstructer release bottle;
11. Sequence is repeated.

In step 1, that singulator may be, e.g., a rotate singulator (e.g., a rotate assembly) that rotates first-in-line bottle out of a queue so as to effectively insert a sufficiently large space between that bottle and a following bottle so the first-in-line bottle can then be moved to the scanning area alone (and accurately scanned without interference from another bottle(s) that is too close). In step 8, in either embodiment (particularly where the pin alone is extended before and during bottle placement), the pin may be extended such that before and during placement, the distance between the end of the pin and a wall 106 on the other side of the conveyor is slightly less than the diameter of the bottle (thereby preventing the bottle's conveyance downflow of that pin). Again, the pick-up and placement operations are often similar to what is seen in puck-based systems. The reason they may still be used in certain puck-free systems is, in the event we there is a failure to read a scan or a wrong bottle is read, such bottle must be passed through without the robot picking up that bad bottle.

Note that in puck-based systems, it may be important in certain embodiments to always use pucks having the same diameter (at least where the obstructers contact the pucks), and that have an internal diameter of the bottle contacting portion that is substantially the same as the outer diameter of the lower portion of the bottle.

In one conceptualization (with respect to both puck-free and puck-based systems), the 0 value of the x axis 81 (for both the first and second puck obstructers) is along an edge 85 of the conveyor that is closer to the robot 31 than is the other conveyor edge, while the 0 value of the y axis 82 coincides with the most upflow edge 86 of a table that supports at least part of the puck obstructers.

Note that at both bottle pick-up and bottle placement, differences in bottle size, including height, could result in necks 87 of bottles (or other convenient site for grasping by the gripper 53) that present, at each site, at various heights (larger capacity bottles may have a larger height, and thus may need to be grasped and dropped off at a higher height above the conveyor). In certain systems, including puck-free and puck based systems, a bottle height (e.g., neck height) may be sensed or known after identifying the bottle (or puck) from its identifier (e.g., bar code and/or RFID, as but two examples); such information regarding height can be used to position the height of the end effector (e.g., gripper) properly so the bottle can be picked up (and placed).

Note that in certain puck-based embodiments, the puck 6 may be bottle size specific, so pucks with an appropriately higher height (of the surface of the puck that contacts the bottle bottom) are used for shorter height bottles, and pucks with an appropriately lower height are used for taller bottles, such that all bottles are presented so that the part of the bottle (such as, but not limited to, the neck) that is grasped by the end effector 29 (e.g., gripper) is always at the same height, regardless of the size/height of the bottle. Such may simplify the bottle pick-up and placement operations, but may indeed add some complexity to the puck and bottle "marrying" process).

Such puck and bottle coordination with respect to height, in combination with obstructers that secure a puck in the same location (in horizontal plane) for the bottle pick-up and placement sites 8, 10, may result in all bottles presented in the same position in space (with respect to x, y and z (height) axes) for bottle pick-up and placement. In puck-based embodiments, where pucks heights may be coordinated with bottle height, it may be that the end effector, for every single bottle, with respect to the bottle pick-up and bottle placement operations, is repositioned not only to the same position (one position for pick-up, and a different for placement) with respect to a horizontal plane, but also the same height (so it is repositioned to the same location in a three dimensional plane). In puck-free systems (and in puck-based systems where there is no coordination with respect to height between puck and bottle), where bottles present with different, e.g., neck heights, obstructers may pick-up or place bottles in the same x-y position, but may need to adjust height during pick-up and placement (i.e., may need to adjust z position).

Note the gripper may exhibit action that closes until the bottle's width is contacted and sufficient pressure to pick it up is reached. More particularly as to operation of the gripper 53 in certain embodiments of the inventive technology that use a gripper of a robot end effector 29 to hold a bottle: a gripper may be pneumatic, solenoid controlled, etc., and may have its opening and closing operations triggered by, e.g., sensors, feedback regarding the position of the end effector 29 (e.g., when the end effector 29 is at the placement site 10, the gripper may be ready to open; when the end effector 29 is at the pick-up site 8, the gripper may be ready to close), or other manner. Open and close actions might only be taken after confirmation/verification of something, e.g., the presence of a bottle before closure of the gripper at a bottle pick-up site. A gripper might even have a single closure scheme—always approach a bottle with the same width between gripper components such as pincers (such as one that is large enough for the largest width bottle), and close until sufficient oppositional force/pressure in response to the closure is sensed. However, it may instead be controlled to close to a width that depends on bottle size, e.g. (note that a pressure sensor may be used to supplement such control to assure an appropriately tight grip). A gripper width sensor may also or instead be used to provide feedback regarding the exact state of the gripper—open, entirely closed, closed on a bottle, and perhaps even closed on a bottle of a certain (e.g., neck 87) width (where bottles are of different neck widths). It should be understood that gripper is a broad term, describing a number of devices that can act to pick up a bottle, hold (e.g., grasp) that bottle so that it can be controllably moved, and then release that bottle so that it is placed at an intended location.

Note that in particular embodiments, while such bottle is trapped (e.g., held stationary) by the first bottle obstructer 44, whether that bottle is "alone," first in a queue or further down a queue, the conveyor may slide under it (if it is a puck-based system, the conveyor slides directly under the puck (and under the bottle). Later, slightly "downflow" on the conveyor, by the second bottle obstructer, the conveyor may slide under the bottle (perhaps for a short time in puck-free systems); in puck-based systems, the conveyor may slide directly under the puck (and slide under the bottle) while the puck waits to receive a filled bottle, and then possibly also for perhaps a short time after the bottle is placed in it.

The bottle pick-up and placement sites 8, 10 are typically two different sites and may be side-by-side. Such side-by-side (serial) arrangement may be said to exist where, e.g., the first and second pick-up points, in a horizontal plane, are separated by at least the horizontal width (e.g., diameter) of a bottle (in puck-free systems) or a puck (or the largest puck width if pucks 6 have different widths, in puck-based systems), up to 400% such width. Such width would typically be along the direction of the conveyor. Other separation distances (outside of such range) are possible but may not be viewed as "side-by-side." It may be that such design (where the pick-up and placement sites are at two distinct, but preferably side-by-side, serial sites) contributes to higher order fill rates because in such design, the "next" bottle can be waiting in position at the bottle pick-up site 8 when the previous bottle is being dropped off (because by having two sites, the next bottle can be positioned at the bottle pick-up site during robotic transport and filling of the previous bottle). Such reduces robot idle and/or transport times, particularly when the bottle pick-up and fill sites are side-by-side (because of their close distance).

Note that certain embodiments of the inventive technology may have distinct bottle pick-up and placement sites, while others may have bottle pick-up and placement sites that are at the same location (the latter design may be a slower than the former due to the need for the robot to wait for a "new" (empty) bottle to be moved into position to replace the previous (filled) bottle that was just placed at that same site). The first and second bottle obstructers may take any of a variety of forms: a clamp of sorts, a forked trapping bar, pins 47 and/or wedges 48, as a few of many possible examples of obstructers that trap the moving bottle in the desired positions at the bottle pick-up and placement sites, whether via directly contacting the bottle (in puck-free systems) or via directly contacting the puck (in puck-based systems).

In certain puck-based systems, after the robot's end effector 29 picks up the bottle so that it can be moved to an appropriate bottle fill site (e.g., below the counted pill reserve container 32 for the counter 22 associated with that bottle), but preferably before the robot's end effector 29 is moved to the bottle placement site 10 to place the filled bottle there, the first bottle obstructer 44 is deactivated (e.g., retracted from its blocking position, reversed, pivoted and/or demagnetized, etc.), and the conveyor then moves the newly "freed" empty puck. Then, typically a short distance down the conveyor (e.g., at least a puck diameter, a few inches, etc.), a second bottle obstructer 45 traps the empty puck at, generally, the bottle placement site, and holds it in proper position so its center aligns with a second point 84, so that the bottle originally/earlier supported in that puck, now containing an ordered number of pills of a particular medication, can be reliably, accurately, and confidently placed in the puck by the robot 31 when it positions its end effector 29 in the same, correct position, at least with respect to a horizontal plane (of course the robot may need to orient/operate its end effector, e.g., its bottle gripper 53, etc., precisely also). Note that, as with the robotic placement of the end effector 29 during bottle pick-up, the robot may (in certain, but not all embodiments) need to move the end effector's gripper (a broad term that includes anything that can pick-up, hold and release the bottle) to one of a plurality of different heights that is appropriate for the size of the bottle (but again, coordination of pucks of different height with bottles depending on bottle size to present a bottle part, e.g., bottle necks 87, that is grasped by the gripper, at a same height regardless of bottle size may eliminate this need). Note that the deactivation of first and second bottle obstructer components such as pin/wedge (and activation thereof also) may be observed also in puck-free systems in order to, e.g., allow for pass-through of rejects or non-reads, or purge a queue, and, for the second bottle obstructer specifically, to provide a hard stop against which the bottle may be placed during bottle placement so the bottle does not tip over due to conveyor motion. In certain embodiments, perhaps the most obvious difference between obstructer in puck-based vs. puck-free systems is the absence of puck-in position sensors in puck-free systems.

Again, in certain puck-based systems, after such placement (of the filled bottle into its waiting, associated puck), the second puck obstructer 45 (which like the first, may include a clamp, a forked trapping bar, pins 47 and/or wedges 48, as but a few examples) may be deactivated (e.g., retracted, etc.) so that the conveyor can move the puck and (filled) bottle combination 49 to, e.g., a next processing station.

Note, as mentioned, that the bottle placement site 10 may be serially established ("side-by-side") next to the bottle pick-up site 8 on the same conveyor. Both sites may be on the conveyor; the conveyor may slide directly under the bottle while it is in each of its two trapped, stationary positions (during bottle pick-up and placement); in puck-based systems, it slides directly against the puck, while in puck-free systems it slides directly under the bottle. Further, the bottle obstructers, whether part of a puck-based or a puck-free system) are typically not part of the robot 31 or its end effector 29 (e.g., the obstructers include one or more bottle obstructer controller along the side of the conveyor in the area of the bottle pick-up and placement sites that activates (e.g., extends, magnetizes, etc.) the obstructers at appropriate time(s) to position the bottle in the desired position, and thereafter deactivates them at appropriate time(s) so that, at the pick-up site, any puck in puck-based systems (or possibly a rejected or misread bottle to be purged, in puck free systems) can be released so it can be conveyed by the conveyor), and at the bottle placement site, the bottle (and any puck) can be conveyed, e.g., to the next station/operation. It may be advantageous to pass through (and not to pickup for filling) any bottle (whether alone or part of a puck and bottle combination) any reject/misread, etc., bottle, whether in a puck-based or a puck-free system.

Activation and deactivation may be controlled and occur so that the robot never needs to delay—an empty bottle (whether supported by a puck or not) is preferably always waiting for the end effector 29 when it arrives (without any delay during a bottle reposition cycle or between cycles) at the bottle pick-up site 8. In puck-based systems, that puck, free of its bottle, is preferably always later waiting for that same bottle, filled, when the end effector 29 arrives (also without any such delay) at the bottle placement site. The controllers may be, e.g., cylinder based, pneumatic, servo-motor, etc.

The bottle positioning obstructers include but are not limited to those shown in the figures, which show pins 47 that extend first, blocking motion in a direction along the conveyor, and then wedges 48 that shortly thereafter extend to block motion in that same ("x") direction, and to block motion in a direction that is perpendicular to that direction (i.e., in a "y" direction across the conveyor). Note that, while such a two component obstructer may provide optimal control (in either a puck-free or puck-based system), it may suffice to have only a single moving component system (e.g., only a pin or only a wedge, or other "trapping/positioning" component).

"Bottle-in" position sensors 88, e.g., photo-eyes, whether laser based or otherwise, may be used to determine whether a bottle is in position at a bottle pick-up site 8 and/or a bottle placement site 10. "Puck-in" position sensors 89 (in puck-based systems) may be used to determine whether a puck is in position at a bottle pick-up site and/or a bottle placement site. Information as to the presence or absence of a bottle or a puck can be used to trigger an action (e.g., in a puck-based system, extension of the first puck obstructer 44 may occur when the puck-in position sensor 89 at the bottle pick-up site indicates presence of a "new" puck 6; release of the first puck obstructer 44 may occur after the bottle-in position sensor 88 at the bottle pick-up site indicates the absence of a bottle; extension of the second puck obstructer 45 may occur when the puck-in position sensor 89 at the bottle placement site indicates presence of a "new" puck; release of the second puck obstructer 45 may occur after the bottle-in position sensor 88 at the bottle placement site indicates the presence of a bottle). In particular embodiments, RFID tag readers (or other type reader) at the bottle pick-up site and/or bottle placement site (or shortly upflow thereof) may be used to read RFID (or other) tags or identifiers that may be placed on pucks 6, perhaps to read an identifying information such as a SKU and confirm that the "correct" puck, as expected, is at a certain position or site. Indeed, RFID tags 58 on, e.g., pucks, and RFID tag readers can be used throughout the system to verify proper system functionality and perhaps also to trigger system events. Alternatively, or in addition, bar codes, image bar codes, QR codes, etc., could be used on bottles and/or pucks to provide identifying information (regarding bottles and/or pucks); in particular puck-based system embodiments, RFID chips are used on pucks while bar codes (2D) are used on bottles.

Particular embodiments of the inventive technology may prevent any undesired spillage of pills from bottles during transport of recently filled bottles. Such transport, in the LVD 15, occurs via a robot 31 and is from a bottle fill site to a bottle placement site 10. Force-related effects, e.g., inertial effects, during such transport, due to robot end effector 29 speed and the path followed by the end effector 29 during such transport (which may involve rising and falling), may result in spillage of pills if the opening of the bottle is not covered in some manner. If the robot is moved sufficiently slowly, such spillage can be avoided, but order fill rates are important, and slow robot speeds compromise order fill rates and are thus undesirable. Covering the opening of bottles during robotic transport while they are full (of the pills required by an order), and more particularly between at least some portion of robotic transport of a (filled) bottle from a bottle fill site to a bottle placement site, may allow higher robot speeds than could otherwise be used. The cover 54 may be part of and controlled by a device located substantially at and as part of the robot end effector; it may be, as but one example, a sliding rigid cover 54 (e.g., a plate) that is slid from a position that is not over a bottle opening (deactivated position) to an activated position that is over (and covering) the bottle opening (enough to prevent pill spillage). Such change from deactivated to activated position may occur after a dispensing event but before the robot's motion might cause pill spillage (e.g., the plate may be slid over the bottle opening when the robot starts to move the bottle from the bottle fill site). The cover 54 may be moved (e.g., slid, pivoted, etc.) back off of the bottle opening (to its deactivated position) at any time after that part of the robot's motion that might cause spillage is over, but at any time before the start of the pill dispensing event of the next bottle reposition cycle (often, the cover is slid off of the bottle opening substantially when the filled bottle arrives at the bottle placement site). As with several of the many actions in the systems used in an automated dispensary, activation and deactivation may be triggered by, e.g., sensors (proximity to a bottle placement site), time (here activation may occur at a certain time, e.g., ¼ second, after motion from a bottle fill site occurs), speed, information/feedback regarding robot position (e.g., deactivation of a cover when a robot reaches a certain yaw (with respect to its base) position), etc.

Another aspect of the inventive technology, in particular embodiments, involves the ability of a robot-based dispensary (again, a term that includes but is not limited to a LVD) to continue to operate even where the robot 31 is offline for whatever reason (robot malfunction, repair, power issues, robot replacement, robot software update, etc.). Such backup capability can be implemented by assuring the robot is offline (for safety reasons), perhaps also folding the robot to occupy a smallest footprint possible, and then having a person replace the robot (at least to an extent), by entering into the general area occupied by the robot (e.g., a central area), having a person then manually move (serially and cyclically) bottles from the bottle pick-up site 8 to the appropriate bottle fill site, causing a reserve container door 52 to open, waiting for the dispensing event to start and complete, closing that door, then moving that filled bottle to the bottle placement site 10 (then picking up the next empty bottle waiting at the bottle pick-up site, and repeating the process for that next bottle). Typically, the robot would be left in place, perhaps with its arm 28 retracted and/or moved away from the bottle pick-up and placement sites so as to be out of the way of the human operator and to occupy minimal footprint.

What may, at least in part, enable such backup, manual mode operation in certain puck-based systems, may be a design where, at least in manual mode, the movement of the puck (associated with a bottle) from the bottle pick-up site 8 to the bottle placement site 10, and conveyance of a "new" bottle to the pick-up site (as caused by release of the puck resulting from, e.g., retraction of a first puck obstructer) is triggered by removal of the bottle from that puck when it is in the bottle pick-up site (e.g., where such release occurs immediately after bottle removal or even a few seconds after bottle removal), and where, at least in manual mode, movement of the filled bottle from the bottle placement site so that it travels along the conveyor to a downstream station (as caused by release of the puck resulting from, e.g., retraction of a second puck obstructer), is triggered by placement of the bottle into its associated puck at the bottle placement site. And in puck-free systems, activation/deactivation of the obstructers may similarly be triggered by removal of a bottle and/or placement of a bottle. Accordingly, a human operator who, for whatever reason, takes longer than he/she should during a bottle repositioning cycle, will not cause a problematic backup in the system; system processing speed, at least downflow of the LVD, will depend on the speed of the human operator (it certainly may be worse with a human operator).

One feature that may help to reduce the time a human operator would otherwise take to reposition bottles as appropriate would be a visual indicator 43 (e.g., a light on a counter 22 or a counted pill reserve container, including door componentry 41) that indicates to which bottle fill site an empty bottle is to be repositioned for correct filling. In one embodiment, such light may be illuminated immediately after an empty bottle is picked up and de-illuminated after a dispensing operation at the illuminated fill site is started or completed, but this is only one of many possible illumination schemes (e.g., in certain embodiments, illumination may start shortly after the completion of a dispensing event for an immediately prior bottle). Accordingly, a human operator can readily and efficiently (without error) transport (manually carry) an empty bottle he/she picked up from the bottle pick-up site 8 to the correct bottle fill site (e.g., in front of and below the counter with the correct medication for the order associated with that bottle, and at the lower end 39 of a counted pill reserve container); after filling, he/she can then transport that filled bottle to the bottle placement site 10, and then pick-up the next (empty) bottle to then bring it to the correct (and illuminated) bottle fill site for that counter.

The provision of such backup, manual operation, despite the slower transport speeds (and slower bottle repositioning cycle times) observed when a human is transporting the bottles (as compared to robotic, automated mode), may still be considered a system advantage because it allows system functionality, albeit perhaps slower and more costly, where a central component—the robot 31—is offline. More expensive and slower functionality is better than no functionality at all. Additional expense of the backup, manual mode may be incurred primarily due to increased labor costs. In addition to the cost of the human who acts to replace the robot, backup, manual mode, unlike robot-assisted mode (perhaps referred to as fully automated mode) may bring with it the disadvantage of requiring Pharmacist Verification 2 during backup operation; PV2 is a quality/safety/security check whereby a pharmacist checks to assure that a filled bottle actually does include the medication that the order with which that bottle is associated requires. Robot-assisted mode (i.e., robotic operation, when the robot is online and functioning) typically does not require such a labor intensive, and thus expensive, security measure because of computerized control of robot position and/or redundant "checks" performed by the robot (including by its end effector) to assure positioning of the end effector 29 at the correct bottle fill site (associated with the correct counter 22, for the correct medication). Indeed, elimination of PV2 is a significant advantage of the more secure (perhaps even "fully secure") robotic dispensary 14.

Further, in manual mode, the individual who is replacing the robot 31 may also need to agitate the counted pill reserve container 32 during a dispensing operation in order to clear (dislodge) any lodged pills, particularly where the device applying the lodged pill clearing force(s) is established at the end of the robot arm 28 on the end effector. This may be done ritually for every pill dispensing, or instead may be done only when a lodged pill(s) is noticed (e.g., which may be possible where reserve containers 32 are clear). Note also that counted pill reserve container door 52 operation may be triggered in some fashion (via sensing, mechanical triggering, etc.), or perhaps even manually opened by the human operator by, e.g., pushing it open. A biased door (biased towards closed mode or in closed direction) may be beneficial in assuring that a human operator does not forget to close the door during backup, manual mode (however, a proximity sensor 42 may be used, in either manual or backup mode, to assure that a door is closed after a dispensing event, whether manually or robotically, alerting if a door is not closed). The "semi-automated" manual mode capability may still be viewed as an advantage because it allows for system operation, albeit slower, more expensive, and/or less secure operation, even where a central component of the fully automated system—the robot—is offline. Note that a system, when the robot is online and functioning (rendering PV2 unnecessary), may be termed fully secure and fully automated even though PV1 may still be required during such operation (and during backup operation also). PV1 is a pharmacist verification check whereby an individual (e.g., a pharmacist) checks to assure that the proper medication is placed in the counter to which it is dedicated (it may include checks to assure that the medication of a particular external hopper 23 attached to and atop a counter is in fact attached to and atop (as part of) the counter dedication to that medication).

In certain embodiments, there may be an external hopper 23 positioned at the top of and as part of the counter 22. It may typically be removably attached thereto, and may be of a size that is intentionally selected to reduce labor (to replenish hoppers, i.e., by removing empty hoppers, refilling them with the proper medication, and then replacing refilled hoppers onto the proper counter). External hoppers 23 of the following sizes (internal capacity)—greater than 1 L (liter), greater than 5 L, greater than 7 L, 5.7 L, 7.5 L, and 8 L—may each present advantages relative to labor costs. For example, use of an external hopper with a 5.7 L capacity, as compared to a hopper with 1 L capacity, may result in labor savings of 84%. Labor cost savings here may be amplified because each refilling/replenishment operation may require a PV1 check, in addition to requiring the labor of manually removing, refilling, and replacing a hopper.

Note that, as used herein, the term "configured" means designed, programmed, set up, arranged, sized, established, powered, controlled, selected from available options, and/or positioned, etc., as disclosed herein and/or as would be within the ability of one of ordinary skill in the art, in order to achieve the indicated feature, ability, function, goal, etc. The term "configuring" has a closely related meaning, and simply means designing, programming, etc. as disclosed herein and/or as would be within the ability of one of ordinary skill in the art, in order to achieve the indicated feature, ability, function, goal, etc. For example, the step of "configuring a robot 31 as part of said system to controllably reposition a robot end effector 29 and bottles held thereby through a plurality of bottle reposition cycles during each of which a different one of said bottles is moved by said robot" may involve the step of positioning the robot in a position with respect to other system components (e.g., an array of counters) that allows it to move its end effector 29 through a plurality of such cycles, and likely also programming or otherwise electronically instructing the robot to move in such manner. The term "established" (and "establishing") as used herein may involve more of a physical positioning of the referenced item to achieve the indicated feature, ability, function, goal, etc., than programming through software or otherwise (although a component established in a certain manner can certainly also be programmed). Substantially, where applicable, may mean within a 20% window centered on an exact match (e.g., 90 and 110 are each (barely) substantially the same as 100).

The inventive technology also includes methods that relate to automated pill dispensing systems. A system may be any apparatus, assembly or device, etc., that can be used to meet any of the needs or achieve any of the functions of embodiments of a dispensary (e.g., even the bottle opening cover 54 and its control componentry, can be a system). Methods may be as described herein, including in the claims; at times they may track or correlate to systems/apparatus described above.

As can be easily understood from the foregoing, the basic concepts of the present invention may be embodied in a variety of ways. It involves both automated dispensing techniques as well as devices to accomplish the appropriate dispensing. In this application, the automated dispensing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "cover" should be understood to encompass disclosure of the act of "covering"—whether explicitly discussed or not—and, conversely, were there effectively disclosure of the act of "covering", such a disclosure should be understood to encompass disclosure of a "cover" and even a "means for covering." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, document, exhibit, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional patent application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the dispensing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

In addition and as to computer aspects and each aspect amenable to programming or other electronic automation, it should be understood that in characterizing these and all other aspects of the invention—whether characterized as a device, a capability, an element, or otherwise, because all of these can be implemented via software, hardware, or even firmware structures as set up for a general purpose computer, a programmed chip or chipset, an ASIC, application specific controller, subroutine, or other known programmable or circuit specific structure—it should be understood that all such aspects are at least defined by structures including, as person of ordinary skill in the art would well recognize: hardware circuitry, firmware, programmed application specific components, and even a general purpose computer programmed to accomplish the identified aspect. For such items implemented by programmable features, the applicant(s) should be understood to have support to claim and make a statement of invention to at least: xv) processes performed with the aid of or on a computer, machine, or computing machine as described throughout the above discussion, xvi) a programmable apparatus as described throughout the above discussion, xvii) a computer readable memory encoded with data to direct a computer comprising means or elements which function as described throughout the above discussion, xviii) a computer, machine, or computing machine configured as herein disclosed and described, xix) individual or combined subroutines and programs as herein disclosed and described, xx) a carrier medium carrying computer readable code for control of a computer to carry out separately each and every individual and combined method described herein or in any claim, xxi) a computer program to perform separately each and every individual and combined method disclosed, xxii) a computer program containing all and each combination of means for performing each and every individual and combined step disclosed, xxiii) a storage medium storing each computer program disclosed, xxiv) a signal carrying a computer program disclosed, xxv) a processor executing instructions that act to achieve the steps and activities detailed, xxvi) circuitry configurations (including configurations of transistors, gates, and the like) that act to sequence and/or cause actions as detailed, xxvii) computer readable medium(s) storing instructions to execute the steps and cause activities detailed, xxviii) the related methods disclosed and described, xxix) similar, equivalent, and even implicit variations of each of these systems and methods, xxx) those alternative designs which accomplish each of the functions shown as are disclosed and described, xxxi) those alternative designs and methods which accomplish each of the functions shown as are implicit to accomplish that which is disclosed and described, xxxii) each feature, component, and step shown as separate and independent inventions, and xxxiii) the various combinations of each of the above and of any aspect, all without limiting other aspects in addition.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A system comprising:
   a conveyor configured to move a plurality of bottles along a path;
   a robot, wherein the robot comprises:
     a robotic arm that is rotatable about a vertical axis; and
     an end effector coupled to the robotic arm,
     wherein the robot is configured to reposition the end effector and at least one bottle of the plurality of bottles held thereby through a bottle reposition cycle during each of which the end effector moves a different bottle of the plurality of bottles to at least one of an empty bottle pick-up site, a bottle fill site, or a filled bottle placement site;
   a plurality of pill counters, wherein each pill counter of the plurality of pill counters is configured to count pills of a particular medication, wherein the plurality of pill counters are arranged to define an interior space, wherein the robot is received within the interior space;
   a plurality of counted pill reserve containers, wherein each counted pill reserve container of the plurality of counted pill reserve containers is configured to receive at least one pill from a pill counter of the plurality of pill counters, and dispense the at least one pill in a bottle at the bottle fill site; and
   one or more computing devices, in communication with the robot, the plurality of pill counters, and the plurality of counted pill reserve containers, wherein the one or more computing devices are configured to:
     receive a plurality of orders for a number of pills of a plurality of medications;
     determine, based on the plurality of orders, an order cluster, wherein the order cluster indicates a sequence of a plurality of bottle reposition cycles associated with the plurality of orders that decreases a time to complete the plurality of bottle reposition cycles compared to a time to complete the plurality of bottle reposition cycles without the order cluster, wherein, during the sequence of the plurality of bottle reposition cycles of the order cluster:
       the robot moves, by the end effector, filled bottles of the plurality of bottles from the bottle fill site to the filled bottle placement site; and
       after each filled bottle of the plurality of bottles is moved from the bottle fill site to the filled bottle placement site, the robot moves, by the end effector, an immediately subsequently processed bottle of the plurality of bottles from the empty bottle pick-up site to the bottle fill site so that each empty bottle is positioned at the bottle fill site only after the respective counted pill reserve container has therein a respective quantity of pills associated with an order of the plurality of orders;

cause, based on the order cluster, the plurality of pill counters to count a respective quantity of pills of a medication of the plurality of medications and dispense the respective quantity of pills into respective counted pill reserve containers of the plurality of counted pill reserve containers; and cause, based on the order cluster, the robot to continuously move, by the end effector, each bottle of the plurality of bottles through a respective bottle reposition cycle of the plurality of bottle reposition cycles to receive the respective quantity of pills from the respective counted pill reserve containers of the plurality of counted pill reserve containers.

2. The system of claim 1, further comprising:
a first bottle obstructer configured to:
prevent an empty bottle from being conveyed along the conveyor, and
position the empty bottle at the bottle pick-up site.

3. The system of claim 1, further comprising:
a first bottle obstructer configured to:
prevent a puck from being conveyed along the conveyor, wherein the puck is configured to support an empty bottle, and
position the puck at the bottle pick-up site.

4. The system of claim 3, further comprising:
a second bottle obstructer positioned downstream of the first bottle obstructer, wherein the second bottle obstructer is configured to:
prevent the puck from being conveyed along the conveyor, wherein the puck is configured to support a filled bottle, and
position the puck at the bottle placement site.

5. The system of claim 1, wherein the one or more computing devices are configured to receive the plurality of orders for the number of pills of the plurality of medications by receiving the plurality of orders as an unordered list; and
wherein the one or more computing devices are configured to determine, based on the plurality of orders, the order cluster by ordering the unordered list of prescriptions in an order in which the plurality of orders is to be processed,
wherein each order is associated with a respective bottle reposition cycle of the plurality of bottle reposition cycles.

6. The system of claim 1, wherein each order of the plurality of orders is associated with an estimated maximum fill time, and wherein the one or more computing devices are configured to determine the order cluster based on the estimated maximum fill times.

7. The system of claim 1, further comprising a sensor configured to determine a size of each bottle of the plurality of bottles during the bottle reposition cycle associated with each bottle of the plurality of bottles.

8. The system of claim 1, further comprising a device configured to move a cover from a de-activated position that is off of an opening of a bottle to an activated position that is over the opening.

9. The system of claim 1, wherein the one or more computing devices are further configured to cause, based on the order cluster, the plurality of pill counters to count a next respective quantity of pills of a respective medication of the plurality of medications after dispensing a previous respective quantity of pills into the respective counted pill reserve containers of the plurality of counted pill reserve containers.

10. The system of claim 1, wherein the plurality of pill counters are circularly positioned around a central area.

11. The system of claim 10, wherein the robot is positioned in the central area.

12. The system of claim 1, wherein the one or more computing devices are configured to cause, based on the order cluster, the robot to continuously move each bottle of the plurality of bottles through the respective bottle reposition cycle of the plurality of bottle reposition cycles to receive the respective quantity of pills from the respective counted pill reserve containers of the plurality of counted pill reserve containers by queueing the at least one bottle of the plurality of bottles before the empty bottle pick-up site so that without delay during the bottle reposition cycle, the robot is configured to reposition the at least one bottle to the bottle fill site only after the respective number of pills associated with the at least one bottle are counted and reserved in a respective counted pill reserve container associated with the bottle fill site.

13. The system of claim 1, wherein the plurality of counted pill reserve containers are configured to store at least 180 cc of pills.

14. The system of claim 1, wherein the plurality of counted pill reserve containers are configured to store at least 200 cc of pills.

15. The system of claim 1, further comprising:
a conveyor recirculation loop configured to divert, at a recirculation loop diversion site, at least one empty bottle; and
wherein the one or more computing devices are further configured to cause, based on a status of at least one pill counter of the plurality of pill counters, the conveyor recirculation loop to divert the at least one empty bottle.

16. The system of claim 15, wherein the status of the at least one pill counter of the plurality of pill counters is one of: the respective quantity of pills of the medication of the plurality of medications associated with the at least one empty bottle are counted, the respective quantity of pills of the medication of the plurality of medications associated with the at least one empty bottle are being counted, or the respective quantity of pills of the medication of the plurality of medications associated with the at least one empty bottle are not yet counted.

17. The system of claim 1, further comprising:
a conveyor recirculation loop configured to divert, at a recirculation loop diversion site, at least one empty bottle; and
wherein the one or more computing devices are further configured to cause, based on a status of at least one counted pill reserve container of the plurality of plurality of counted pill reserve containers, the conveyor recirculation loop to divert the at least one empty bottle.

18. The system of claim 17, wherein the status of the at least one counted pill reserve container of the plurality of counted pill reserve containers is one of:
the respective quantity of pills of the medication of the plurality of medications associated with the at least one empty bottle are contained in the at least one counted pill reserve container or the respective quantity of pills of the medication of the plurality of medications associated with the at least one empty bottle are not contained in the at least one counted pill reserve container.

19. The system of claim 1, wherein the one or more computing devices are further configured to:
determine, based on the order cluster, a pill counter positioning arrangement to reduce travel time of the end effector to fulfill the plurality of orders in the order cluster as compared to a travel time to fulfill the plurality of orders without the order cluster, wherein the pill counter positioning arrangement comprises a respective location at which each pill counter of the plurality of pill counters is to be positioned.

20. The system of claim 1, wherein the plurality of pill counters are arranged in a substantially circular arrangement.

* * * * *